(12) United States Patent
Hu et al.

(10) Patent No.: US 11,701,357 B2
(45) Date of Patent: Jul. 18, 2023

(54) TREATMENT OF B CELL CANCERS USING A COMBINATION COMPRISING BTK INHIBITORS

(71) Applicant: BeiGene Switzerland Gmbh, Basel (CH)

(72) Inventors: Nan Hu, Beijing (CN); Lai Wang, Beijing (CN); Jing Song, Beijing (CN); Tong Zhang, Beijing (CN); Kang Li, Beijing (CN); Lusong Luo, Beijing (CN); Min Wei, Beijing (CN); Zhiwei Wang, Beijing (CN); Yunhang Guo, Beijing (CN)

(73) Assignee: BEIGENE SWITZERLAND GMBH, Basel (CH)

( * ) Notice: Subject to any disclaimer, the term of this patent is extended or adjusted under 35 U.S.C. 154(b) by 292 days.

(21) Appl. No.: 16/326,467

(22) PCT Filed: Aug. 18, 2017

(86) PCT No.: PCT/CN2017/098023
§ 371 (c)(1),
(2) Date: Feb. 19, 2019

(87) PCT Pub. No.: WO2018/033135
PCT Pub. Date: Feb. 22, 2018

(65) Prior Publication Data
US 2021/0275530 A1 Sep. 9, 2021

(30) Foreign Application Priority Data
Aug. 19, 2016 (WO) ................ PCT/CN2016/096082

(51) Int. Cl.
*A61K 31/519* (2006.01)
*A61P 35/00* (2006.01)
*A61K 39/395* (2006.01)
*A61K 39/00* (2006.01)

(52) U.S. Cl.
CPC ........ *A61K 31/519* (2013.01); *A61K 39/3955* (2013.01); *A61P 35/00* (2018.01); *A61K 2039/505* (2013.01)

(58) Field of Classification Search
CPC .......... C07K 16/2887; A61K 39/39558; A61K 31/519
See application file for complete search history.

(56) References Cited

U.S. PATENT DOCUMENTS

| | | | |
|---|---|---|---|
| 5,624,821 A | 4/1997 | Winter et al. |
| 5,629,204 A | 5/1997 | Honjo et al. |
| 5,648,260 A | 7/1997 | Winter et al. |
| 5,698,520 A | 12/1997 | Honjo et al. |
| 5,994,514 A | 11/1999 | Jardieu et al. |
| 6,165,745 A | 12/2000 | Ward et al. |
| 6,194,551 B1 | 2/2001 | Idusogie et al. |
| 6,528,624 B1 | 3/2003 | Idusogie et al. |
| 6,632,927 B2 | 10/2003 | Adair et al. |
| 6,737,056 B1 | 5/2004 | Presta |
| 6,808,710 B1 | 10/2004 | Wood et al. |
| 6,936,704 B1 | 8/2005 | Freeman et al. |
| 7,029,674 B2 | 4/2006 | Carreno et al. |
| 7,038,013 B2 | 5/2006 | Freeman et al. |
| 7,101,550 B2 | 9/2006 | Wood et al. |
| 7,122,637 B2 | 10/2006 | Presta |
| 7,297,775 B2 | 11/2007 | Idusogie et al. |
| 7,317,091 B2 | 1/2008 | Lazar et al. |
| 7,332,581 B2 | 2/2008 | Presta |
| 7,335,742 B2 | 2/2008 | Presta |
| 7,355,008 B2 | 4/2008 | Stavenhagen et al. |
| 7,364,731 B2 | 4/2008 | Idusogie et al. |
| 7,371,826 B2 | 5/2008 | Presta |
| 7,393,848 B2 | 7/2008 | Currie et al. |
| 7,414,171 B2 | 8/2008 | Honjo et al. |
| 7,416,726 B2 | 8/2008 | Ravetch |
| 7,488,802 B2 | 2/2009 | Collins et al. |

(Continued)

FOREIGN PATENT DOCUMENTS

| CN | 1753912 A | 3/2006 |
|---|---|---|
| CN | 1771231 A | 5/2006 |

(Continued)

OTHER PUBLICATIONS

Li Na et al. BGB-3111 is a novel and highly selective Bruton's tyrosine kinase (BTK) inhibitor. Cancer Research, vol. 75, Supp. 1, Abstract No. 2597. 106th Annual Meeting of the American Association for Cancer Research, AACR 2015. Philadelphia, PA, United States. Apr. 18, 2015-Apr. 22, 2015. (Year: 2015).*
Anonymous, MedChemExpress for BGB-3111 (Zanubrutinib) (retrieved from www.MedChemExpress.com on Aug. 17, 2021). (Year: 2021).*
Kourtzelis et al.—The dual role of complement in cancer and its implication in anti-tumor therapy. Ann Transl Med 4, 265, 2016. (Year: 2016).*
Extended European Search Report for European Application No. 14787642.9, dated Jan. 26, 2016, 5 pages.

(Continued)

*Primary Examiner* — Elly-Gerald Stoica
(74) *Attorney, Agent, or Firm* — Cooley LLP

(57) ABSTRACT

Disclosed herein is a method for the prevention, delay of progression or treatment of cancer in a subject, comprising administering to the subject in need thereof a Btk inhibitor, particularly, (S)-7-(1-acryloylpiperidin-4-yl)-2-(4-phenoxyphenyl)-4,5,6,7-tetra-hydropyrazolo[1,5-a]pyrimidine-3-carboxamide or a pharmaceutically acceptable salt thereof, in combination with an immune checkpoint inhibitor or a targeted therapy agent. Also, disclosed a pharmaceutical combination comprising a Btk inhibitor, particularly, (S)-7-(1-acryloylpiperidin-4-yl)-2-(4-phenoxyphenyl)-4,5,6,7-tetra-hydropyrazolo[1,5-a]pyrimidine-3-carboxamide or a pharmaceutically acceptable salt thereof, in combination with an immune checkpoint inhibitor, or a targeted therapy agent and the use thereof.

19 Claims, 7 Drawing Sheets
Specification includes a Sequence Listing.

(56) References Cited

U.S. PATENT DOCUMENTS

| | | |
|---|---|---|
| 7,514,444 B2 | 4/2009 | Honigberg et al. |
| 7,563,869 B2 | 7/2009 | Honjo et al. |
| 7,595,048 B2 | 9/2009 | Honjo et al. |
| 7,597,889 B1 | 10/2009 | Armour et al. |
| 7,608,429 B2 | 10/2009 | Reilly et al. |
| 7,635,757 B2 | 12/2009 | Freeman et al. |
| 7,638,492 B2 | 12/2009 | Wood et al. |
| 7,655,783 B2 | 2/2010 | Reilly et al. |
| 7,670,600 B2 | 3/2010 | Dall'Acqua et al. |
| 7,718,662 B1 | 5/2010 | Chen et al. |
| 7,741,072 B2 | 6/2010 | Idusogie et al. |
| 7,790,858 B2 | 9/2010 | Presta |
| 7,851,598 B2 | 12/2010 | Davis |
| 7,863,419 B2 | 1/2011 | Taylor et al. |
| 7,943,743 B2 | 5/2011 | Korman et al. |
| 7,998,479 B2 | 8/2011 | Honjo et al. |
| 8,008,449 B2 | 8/2011 | Korman et al. |
| 8,084,620 B2 | 12/2011 | Liu et al. |
| 8,088,905 B2 | 1/2012 | Collins et al. |
| 8,168,179 B2 | 5/2012 | Honjo et al. |
| 8,168,757 B2 | 5/2012 | Finnefrock et al. |
| 8,217,149 B2 | 7/2012 | Irving et al. |
| 8,246,955 B2 | 8/2012 | Honjo et al. |
| 8,354,509 B2 | 1/2013 | Carven et al. |
| 8,552,154 B2 | 10/2013 | Freeman et al. |
| 8,617,546 B2 | 12/2013 | Kang et al. |
| 8,728,474 B2 | 5/2014 | Honjo et al. |
| 8,735,553 B1 * | 5/2014 | Li .................... A61P 25/00 530/388.22 |
| 8,779,105 B2 | 7/2014 | Korman et al. |
| 8,911,726 B2 | 12/2014 | Takahashi et al. |
| 8,945,561 B2 | 2/2015 | Davis |
| 9,067,999 B1 | 6/2015 | Honjo et al. |
| 9,073,994 B2 | 7/2015 | Honjo et al. |
| 9,084,776 B2 | 7/2015 | Korman et al. |
| 9,139,653 B1 | 9/2015 | Campbell et al. |
| 9,175,082 B2 | 11/2015 | Zhou et al. |
| 9,217,034 B2 | 12/2015 | Li et al. |
| 9,447,106 B2 | 9/2016 | Wang et al. |
| 9,492,540 B2 | 11/2016 | Korman et al. |
| 9,556,188 B2 | 1/2017 | Wang et al. |
| 9,624,298 B2 | 4/2017 | Nastri et al. |
| 9,834,606 B2 | 12/2017 | Li et al. |
| 9,920,123 B2 | 3/2018 | Irving et al. |
| 9,988,450 B2 | 6/2018 | Li et al. |
| 10,005,782 B2 | 6/2018 | Wang et al. |
| 10,058,609 B2 | 8/2018 | Zhou et al. |
| 10,487,147 B2 | 11/2019 | Nastri et al. |
| 10,519,235 B2 | 12/2019 | Li et al. |
| 10,544,225 B2 | 1/2020 | Li et al. |
| 10,550,185 B2 | 2/2020 | Bernett et al. |
| 10,570,139 B2 | 2/2020 | Wang et al. |
| 10,793,632 B2 | 10/2020 | Bernett et al. |
| 10,858,435 B2 | 12/2020 | Finlay |
| 10,864,203 B2 | 12/2020 | Song et al. |
| 10,927,117 B2 | 2/2021 | Wang et al. |
| 11,142,528 B2 | 10/2021 | Wang et al. |
| 11,186,637 B2 | 11/2021 | Li et al. |
| 11,202,782 B2 | 12/2021 | Wang et al. |
| 11,203,637 B2 | 12/2021 | Zhang et al. |
| 11,377,449 B2 | 7/2022 | Wang et al. |
| 11,512,132 B2 | 11/2022 | Li et al. |
| 11,555,038 B2 | 1/2023 | Guo et al. |
| 2002/0094989 A1 | 7/2002 | Hale et al. |
| 2004/0038339 A1 | 2/2004 | Kufer et al. |
| 2005/0064514 A1 | 3/2005 | Stavenhagen et al. |
| 2005/0202028 A1 | 9/2005 | Ledbetter et al. |
| 2006/0121032 A1 | 6/2006 | Dahiyat et al. |
| 2006/0134105 A1 | 6/2006 | Lazar et al. |
| 2006/0178367 A1 | 8/2006 | Currie et al. |
| 2006/0183746 A1 | 8/2006 | Currie et al. |
| 2006/0263856 A1 | 11/2006 | Gillies et al. |
| 2007/0160597 A1 | 7/2007 | Lazar et al. |
| 2008/0076921 A1 | 3/2008 | Honigberg et al. |
| 2008/0139582 A1 | 6/2008 | Honigberg et al. |
| 2009/0068175 A1 | 3/2009 | Lazar et al. |
| 2009/0105209 A1 | 4/2009 | Dewdney et al. |
| 2009/0155256 A1 | 6/2009 | Black et al. |
| 2009/0217401 A1 | 8/2009 | Korman et al. |
| 2009/0318441 A1 | 12/2009 | Brain et al. |
| 2010/0004231 A1 | 1/2010 | Dewdney et al. |
| 2010/0016296 A1 | 1/2010 | Singh et al. |
| 2010/0016301 A1 | 1/2010 | Dewdney et al. |
| 2010/0029610 A1 | 2/2010 | Singh et al. |
| 2010/0035841 A1 | 2/2010 | Jankowski et al. |
| 2010/0087464 A1 | 4/2010 | Mi et al. |
| 2010/0105676 A1 | 4/2010 | Liu et al. |
| 2010/0144705 A1 | 6/2010 | Miller |
| 2010/0151492 A1 | 6/2010 | Ahmed et al. |
| 2010/0160292 A1 | 6/2010 | Whitney et al. |
| 2010/0160303 A1 | 6/2010 | Liu et al. |
| 2010/0197924 A1 | 8/2010 | Gould et al. |
| 2010/0222325 A1 | 9/2010 | Berthel et al. |
| 2010/0249092 A1 | 9/2010 | Singh et al. |
| 2010/0254905 A1 | 10/2010 | Honigberg et al. |
| 2010/0317834 A1 | 12/2010 | Lazar et al. |
| 2011/0008369 A1 | 1/2011 | Finnefrock et al. |
| 2011/0052584 A1 | 3/2011 | Ravetch |
| 2011/0054151 A1 | 3/2011 | Lazar et al. |
| 2011/0118233 A1 | 5/2011 | Blomgren et al. |
| 2011/0124640 A1 | 5/2011 | Liu et al. |
| 2011/0159023 A1 | 6/2011 | Langermann |
| 2011/0171215 A1 | 7/2011 | Davis et al. |
| 2011/0171220 A1 | 7/2011 | Davis |
| 2011/0177088 A1 | 7/2011 | Olive et al. |
| 2011/0195068 A1 | 8/2011 | Langermann et al. |
| 2011/0224235 A1 | 9/2011 | Honigberg et al. |
| 2011/0271358 A1 | 11/2011 | Freeman et al. |
| 2011/0287032 A1 | 11/2011 | Lazar et al. |
| 2011/0301145 A1 | 12/2011 | Barbosa, Jr. et al. |
| 2012/0028981 A1 | 2/2012 | Miller |
| 2012/0040961 A1 | 2/2012 | Gray et al. |
| 2012/0053189 A1 | 3/2012 | Loury |
| 2012/0058996 A1 | 3/2012 | Liu et al. |
| 2012/0076726 A1 | 3/2012 | Gellerfors et al. |
| 2012/0077832 A1 | 3/2012 | Witowski et al. |
| 2012/0082702 A1 | 4/2012 | DeLucca et al. |
| 2012/0129852 A1 | 5/2012 | Duan et al. |
| 2012/0157442 A1 | 6/2012 | Bui et al. |
| 2012/0157443 A1 | 6/2012 | Bui et al. |
| 2012/0232054 A1 | 9/2012 | Moriarty et al. |
| 2012/0237522 A1 | 9/2012 | Kang et al. |
| 2012/0251531 A1 | 10/2012 | Baehner et al. |
| 2013/0004514 A1 | 1/2013 | Zahn et al. |
| 2013/0079327 A1 | 3/2013 | Yamamoto et al. |
| 2013/0089541 A1 | 4/2013 | D'Angelo et al. |
| 2013/0096118 A1 | 4/2013 | Liu et al. |
| 2013/0116213 A1 | 5/2013 | Cha et al. |
| 2013/0259868 A1 | 10/2013 | Roschke et al. |
| 2013/0261103 A1 | 10/2013 | Currie et al. |
| 2013/0281432 A1 | 10/2013 | Currie et al. |
| 2013/0309250 A1 | 11/2013 | Cogswell et al. |
| 2014/0044738 A1 | 2/2014 | Langermann et al. |
| 2014/0045833 A1 | 2/2014 | Laurent et al. |
| 2014/0094459 A1 | 4/2014 | Goldstein et al. |
| 2014/0107151 A1 | 4/2014 | Goldstein et al. |
| 2014/0162316 A1 | 6/2014 | O'Neil et al. |
| 2014/0162983 A1 | 6/2014 | Hodous et al. |
| 2014/0221398 A1 | 8/2014 | Goldstein et al. |
| 2014/0243306 A1 | 8/2014 | Heng et al. |
| 2014/0243504 A1 | 8/2014 | Davis et al. |
| 2014/0245468 A1 | 8/2014 | McWhirter et al. |
| 2014/0271642 A1 | 9/2014 | Murphy et al. |
| 2014/0314714 A1 | 10/2014 | Honjo et al. |
| 2014/0341902 A1 | 11/2014 | Maecker et al. |
| 2014/0356322 A1 | 12/2014 | Crews et al. |
| 2014/0356363 A1 | 12/2014 | Zhou et al. |
| 2014/0377269 A1 | 12/2014 | Mabry et al. |
| 2015/0044231 A1 | 2/2015 | Kjaergaard et al. |
| 2015/0079109 A1 | 3/2015 | Li et al. |
| 2015/0118222 A1 | 4/2015 | Levy et al. |
| 2015/0125444 A1 | 5/2015 | Tsui et al. |
| 2015/0210763 A1 | 7/2015 | Kuramochi et al. |
| 2015/0259354 A1 | 9/2015 | Wang et al. |

(56) References Cited

U.S. PATENT DOCUMENTS

| | | |
|---|---|---|
| 2015/0315274 A1 | 11/2015 | Li et al. |
| 2015/0337053 A1 | 11/2015 | McCarthy et al. |
| 2015/0353631 A1 | 12/2015 | Buttini et al. |
| 2016/0045607 A1 | 2/2016 | Crew et al. |
| 2016/0083392 A1 | 3/2016 | Wang et al. |
| 2016/0272639 A1 | 9/2016 | Crew et al. |
| 2017/0008904 A1 | 1/2017 | Crew et al. |
| 2017/0044260 A1 | 2/2017 | Baruah et al. |
| 2017/0073349 A1 | 3/2017 | Wang et al. |
| 2018/0037655 A1 | 2/2018 | Hegde et al. |
| 2018/0050021 A1 | 2/2018 | Ciulli et al. |
| 2018/0072711 A1 | 3/2018 | Crew et al. |
| 2018/0200273 A1 | 7/2018 | Nguyen et al. |
| 2018/0215825 A1 | 8/2018 | Li et al. |
| 2018/0251466 A1 | 9/2018 | Wang et al. |
| 2018/0251551 A1 | 9/2018 | Li et al. |
| 2019/0111142 A1 | 4/2019 | Nguyen et al. |
| 2019/0127359 A1 | 5/2019 | Crews et al. |
| 2019/0169201 A1 | 6/2019 | Wang et al. |
| 2019/0183913 A1 | 6/2019 | Nguyen et al. |
| 2020/0030339 A1 | 1/2020 | Wang et al. |
| 2020/0069666 A1 | 3/2020 | Song et al. |
| 2020/0148690 A1 | 5/2020 | Wang et al. |
| 2020/0181150 A1 | 6/2020 | Wang et al. |
| 2020/0216535 A1 | 7/2020 | Li et al. |
| 2020/0283527 A1 | 9/2020 | Li et al. |
| 2020/0368237 A1 | 11/2020 | Hilger et al. |
| 2020/0392131 A1 | 12/2020 | Crew et al. |
| 2021/0040213 A1 | 2/2021 | Song et al. |
| 2021/0130363 A1 | 5/2021 | Wang et al. |
| 2021/0147543 A1 | 5/2021 | Wang et al. |
| 2021/0161921 A1 | 6/2021 | Nguyen et al. |
| 2021/0228553 A1 | 7/2021 | Song et al. |
| 2021/0230274 A1 | 7/2021 | Li et al. |
| 2021/0332049 A1 | 10/2021 | Guo et al. |
| 2022/0119524 A1 | 4/2022 | Li et al. |
| 2022/0135675 A1 | 5/2022 | Zhang et al. |
| 2022/0241285 A1 | 8/2022 | Wang et al. |
| 2022/0249491 A1 | 8/2022 | Qiu et al. |
| 2022/0274994 A1 | 9/2022 | Wang et al. |
| 2022/0281876 A1 | 9/2022 | Wang et al. |
| 2022/0281881 A1 | 9/2022 | Wang et al. |
| 2022/0298163 A1 | 9/2022 | Wang et al. |
| 2022/0340583 A1 | 10/2022 | Wang et al. |
| 2022/0340584 A1 | 10/2022 | Wang et al. |
| 2023/0013862 A1 | 1/2023 | Wang et al. |

FOREIGN PATENT DOCUMENTS

| | | |
|---|---|---|
| CN | 101104640 A | 1/2008 |
| CN | 101213297 A | 7/2008 |
| CN | 101355965 A | 1/2009 |
| CN | 101899114 A | 12/2010 |
| CN | 102245640 A | 11/2011 |
| CN | 102264762 A | 11/2011 |
| CN | 102656173 A | 9/2012 |
| CN | 104736569 A | 6/2015 |
| CN | 104884458 A | 9/2015 |
| CN | 105531288 A | 4/2016 |
| CN | 106103485 A | 11/2016 |
| CN | 107011441 A | 8/2017 |
| CN | 107090041 A | 8/2017 |
| CN | 108136044 A | 6/2018 |
| CN | 108601764 A | 9/2018 |
| CN | 109475567 A | 3/2019 |
| GB | 1412017 A | 10/1975 |
| JP | H07278148 A | 10/1995 |
| JP | 2006510582 A | 3/2006 |
| JP | 2008544755 A | 12/2008 |
| JP | 2009155338 A | 7/2009 |
| JP | 2010528993 A | 8/2010 |
| JP | 2012511329 A | 5/2012 |
| JP | 2012254092 A | 12/2012 |
| KR | 20080011428 A | 2/2008 |
| KR | 20100054780 A | 5/2010 |
| WO | WO-9429351 A2 | 12/1994 |
| WO | WO 2001/019829 A2 | 3/2001 |
| WO | WO-0116138 A1 | 3/2001 |
| WO | WO-0220740 A2 | 3/2002 |
| WO | WO 2002/050071 A1 | 6/2002 |
| WO | WO-02072576 A1 | 9/2002 |
| WO | WO 2003/004497 A1 | 1/2003 |
| WO | WO 2004/017908 A3 | 3/2004 |
| WO | WO 2005/005429 A1 | 1/2005 |
| WO | WO 2005/011597 A2 | 2/2005 |
| WO | WO 2005/014599 A1 | 2/2005 |
| WO | WO 2005/047290 A2 | 5/2005 |
| WO | WO-2005077981 A2 | 8/2005 |
| WO | WO 2006/053121 A2 | 5/2006 |
| WO | WO 2006/065946 A1 | 6/2006 |
| WO | WO-2006084015 A2 | 8/2006 |
| WO | WO 2006/099075 A2 | 9/2006 |
| WO | WO-2006121168 A1 | 11/2006 |
| WO | WO-2006133396 A2 | 12/2006 |
| WO | WO-2007005874 A2 | 1/2007 |
| WO | WO 2007/026720 A1 | 3/2007 |
| WO | WO 2007/027594 A1 | 3/2007 |
| WO | WO 2007/027729 A1 | 3/2007 |
| WO | WO-2007026950 A1 | 3/2007 |
| WO | WO-2007067444 A1 | 6/2007 |
| WO | WO 2007/087068 A2 | 8/2007 |
| WO | WO 2007/136790 A2 | 11/2007 |
| WO | WO-2007136572 A2 | 11/2007 |
| WO | WO 2008/033834 A1 | 3/2008 |
| WO | WO 2008/033854 A1 | 3/2008 |
| WO | WO 2008/033857 A2 | 3/2008 |
| WO | WO-2008039218 A2 | 4/2008 |
| WO | WO 2008/054827 A2 | 5/2008 |
| WO | WO 2008/144253 A1 | 11/2008 |
| WO | WO-2008145142 A1 | 12/2008 |
| WO | WO-2008156712 A1 | 12/2008 |
| WO | WO 2009/039397 A2 | 3/2009 |
| WO | WO 2009/051822 A1 | 4/2009 |
| WO | WO 2009/077334 A1 | 6/2009 |
| WO | WO 2009/098144 A1 | 8/2009 |
| WO | WO-2009100309 A2 | 8/2009 |
| WO | WO 2009/158571 A1 | 12/2009 |
| WO | WO 2010/000633 A1 | 1/2010 |
| WO | WO 2010/006947 A1 | 1/2010 |
| WO | WO 2010/006970 A1 | 1/2010 |
| WO | WO 2010/028236 A1 | 3/2010 |
| WO | WO-2010051549 A1 | 5/2010 |
| WO | WO 2010/065898 A2 | 6/2010 |
| WO | WO 2010/068788 A1 | 6/2010 |
| WO | WO 2010/068806 A1 | 6/2010 |
| WO | WO 2010/068810 A2 | 6/2010 |
| WO | WO-2010077634 A1 | 7/2010 |
| WO | WO-2010089411 A2 | 8/2010 |
| WO | WO 2010/122038 A1 | 10/2010 |
| WO | WO-2011006074 A1 | 1/2011 |
| WO | WO 2011/140488 A1 | 11/2011 |
| WO | WO 2011/153514 A2 | 12/2011 |
| WO | WO 2012/020008 A1 | 2/2012 |
| WO | WO-2012083370 A1 | 6/2012 |
| WO | WO 2012/135801 A1 | 10/2012 |
| WO | WO 2012/143522 A1 | 10/2012 |
| WO | WO-2012130831 A1 | 10/2012 |
| WO | WO-2012135408 A1 | 10/2012 |
| WO | WO-2012145493 A1 | 10/2012 |
| WO | WO 2012/156334 A1 | 11/2012 |
| WO | WO 2012/158795 A1 | 11/2012 |
| WO | WO-2012175692 A1 | 12/2012 |
| WO | WO-2013079174 A1 | 6/2013 |
| WO | WO-2013106643 A2 | 7/2013 |
| WO | WO-2013173223 A1 | 11/2013 |
| WO | WO-2013181634 A2 | 12/2013 |
| WO | WO-2014055897 A2 | 4/2014 |
| WO | WO-2014100079 A1 | 6/2014 |
| WO | WO-2014108452 A1 | 7/2014 |
| WO | WO 2014/173289 A1 | 10/2014 |
| WO | WO-2015035606 A1 | 3/2015 |
| WO | WO 2015/061752 A1 | 4/2015 |
| WO | WO-2015112900 A1 | 7/2015 |
| WO | WO-2016000619 A1 | 1/2016 |

(56) References Cited

FOREIGN PATENT DOCUMENTS

| | | |
|---|---|---|
| WO | WO-2016008411 A1 | 1/2016 |
| WO | WO2016024228 * | 2/2016 ............. A61K 31/00 |
| WO | WO-2016025720 A1 | 2/2016 |
| WO | WO-2016064649 A1 | 4/2016 |
| WO | WO 2016/087994 A1 | 6/2016 |
| WO | WO 2016/100914 A1 | 6/2016 |
| WO | WO 2016/105582 A1 | 6/2016 |
| WO | WO-2016146985 A1 | 9/2016 |
| WO | WO-2016149668 A1 | 9/2016 |
| WO | WO-2016149989 A1 | 9/2016 |
| WO | WO-2016197032 A1 | 12/2016 |
| WO | WO-2016197114 A1 | 12/2016 |
| WO | WO-2017011590 A1 | 1/2017 |
| WO | WO-2017025016 A1 | 2/2017 |
| WO | WO-2017030814 A1 | 2/2017 |
| WO | WO-2017046746 A1 | 3/2017 |
| WO | WO-2017059224 A2 | 4/2017 |
| WO | WO-2017079267 A1 | 5/2017 |
| WO | WO-2017182418 A1 | 10/2017 |
| WO | WO-2017197036 A1 | 11/2017 |
| WO | WO-2017197046 A1 | 11/2017 |
| WO | WO-2017197051 A1 | 11/2017 |
| WO | WO-2017197056 A1 | 11/2017 |
| WO | WO-2017201449 A1 | 11/2017 |
| WO | WO-2017211924 A1 | 12/2017 |
| WO | WO-2017214491 A1 | 12/2017 |
| WO | WO-2018033135 A1 | 2/2018 |
| WO | WO-2018033556 A1 | 2/2018 |
| WO | WO-2018033853 A2 | 2/2018 |
| WO | WO-2018071606 A1 | 4/2018 |
| WO | WO-2018098275 A1 | 5/2018 |
| WO | WO-2018098280 A1 | 5/2018 |
| WO | WO-2018137681 A1 | 8/2018 |
| WO | WO-2018193105 A1 | 10/2018 |
| WO | WO-2019001417 A1 | 1/2019 |
| WO | WO-2019034009 A1 | 2/2019 |
| WO | WO-2019108795 A1 | 6/2019 |
| WO | WO-2019157353 A1 | 8/2019 |
| WO | WO-2019183226 A1 | 9/2019 |
| WO | WO-2020249001 A1 | 12/2020 |
| WO | WO-2020249002 A1 | 12/2020 |
| WO | WO-2021018018 A1 | 2/2021 |

OTHER PUBLICATIONS

International Search Report and Written Opinion for International Application No. PCT/CN2014/075943, dated Jul. 18, 2014, 10 pages.

International Search Report and Written Opinion for International Application No. PCT/IB2017/054955, dated Sep. 10, 2018, 16 pages.

International Search Report and Written Opinion for International Application No. PCT/CN2017/098023, dated Nov. 16, 2017, 10 pages.

Bradshaw, J. M., "The Src, Syk, and Tec family kinases: Distinct types of molecular switches," Cell Signalling, 22:1175-1184 (2010).

Conley, M. E. et al., "Primary B Cell Immunodeficiencies: Comparisons and Contrasts," Annu. Rev. Immunol., 27:199-227 (2009).

Davis, R. E. et al., "Chronic active B-cell-receptor signalling in diffuse large B-cell lymphoma," Nature, 463:88-92 (2010).

Gurcan, H. M. et al., "A review of the current use of rituximab in autoimmune diseases," Int. Immunopharmacol., 9:10-25 (2009).

Hackam, D. G. et al., "Translation of research evidence from animals to humans," JAMA, 296(14):1731-1732 (2006).

Humphries, L. A. et al., "Tec Kinases Mediate Sustained Calcium Influx via Site-specific Tyrosine Phosphorylation of the Phospholipase Cγ Src Homology 2-Src Homology 3 Linker," J. Biol.Chem. 279(36):37651-37661 (2004).

Jenkins, S. M. et al., "Substituent variation in azabicydic triazole- and tetrazole-based muscarinic receptor ligands," J. Med. Chem., 35(13):2392-2406 (1992).

Jordan, V. C., "Tamoxifen: A most unlikely pioneering medicine," Nature Reviews: Drug Discovery, 2:205-213 (2003).

Khan, W. N., "Regulation of B lymphocyte development and activation by Bruton's tyrosine kinase," Immunol. Res., 23(2/3):147-156 (2001).

Kim, K.-H. et al., "Imidazo[1,5-a]quinoxalines as irreversible BTK inhibitors for the treatment of rheumatoid arthritis," Bioorg. Med. Chem. Lett., 21:6258-6263 (2011).

Lou, Y. et al., "Bruton's tyrosine kinase inhibitors: Approaches to potent and selective inhibition, preclinical and clinical evaluation for inflammatory diseases and B cell malignancies," J. Med. Chem., 55(10):4539-4550 (2012).

Mohamed, A. J. et al., "Bruton's tyrosine kinase (Btk): function, regulation, and transformation with special emphasis on the PH domain," Immunol. Rev., 228:58-73 (2009).

Pan, Z, "Bruton's tyrosine kinase as a drug discovery target," Drug News Perspect, 21(7):357-362 (2008).

Rokosz, L. L. et al., "Kinase inhibitors as drugs for chronic inflammatory and immunological diseases: progress and challenges," Expert Opin. Ther. Targets, 12(7):883-903 (2008).

Smith, C. I. E. et al., "Expression of Bruton's Agammaglobulinemia Tyrosine Kinase Gene, BTK, Is Selectively Down-Regulated in T Lymphocytes and Plasma Cells," J. Immunol., 152:557-565 (1994).

Uckun, F. M. et al., "Bruton's tyrosine kinase as a new therapeutic target," Anti-Cancer Agents in Medicinal Chemistry, 7(6):624-632 (2007).

Vetrie, D. et al., "The gene involved in X-linked agammaglobulinaemia is a member of the src family of protein-tyrosine kinases," Nature, 361:226-233 (1993).

Wilson, W. H. et al., "686—The Bruton's Tyrosine Kinase (Btk) Inhibitor, Ibrutinib (PCI-32765), Has Preferential Activity in the ABC Subtype of Relapsed/Refractory De Novo Diffuse Large B-Cell Lymphoma (DLBCL): Interim Results of a Multicenter, Open-Label, Phase2 Study," Poster #686, 54th American Society of Hematology (ASH) annual meeting abstract (Dec. 10, 2012).

Abdiche et al., "Assessing kinetic and epitopic diversity across orthogonal monoclonal antibody generation platforms." mABs (Feb.-Mar. 2016); 8(2):264-277.

Ahmadzadeh, M. et al., "Tumor antigen-specific CD8 T cells infiltrating the tumor express high levels of PD-1 and are functionally impaired," Blood. Aug. 20, 2009;114(8):1537-1544. doi: 10.1182/blood-2008-12-195792. Epub May 7, 2009.

Araki, K. et al., "Programmed cell death 1-directed immunotherapy for enhancing T-cell function," Cold Spring Harbor Symposia on Quantitative Biology, vol. LXXVIII, 239-247 (2013).

Arlauckas, S.P. et al., "In vivo imaging reveals a tumor-associated macrophage-mediated resistance pathway in anti-PD-1 therapy," Sci. Transl. Med., 9, eaal3604 (May 2017), 10 pages.

Balar, A. et al., "Pembrolizumab (pembro) as first-line therapy for advanced/unresectable or metastatic urothelial cancer: Preliminary results from the phase 2 KEYNOTE-052 study," Annals of Oncology 27 (Supplement 6): vi552-vi587, 2016.

Balbach, S. et al., "Pharmaceutical evaluation of early development candidates: 'The 100 mg-approach'," International Journal of Pharmaceutics, (2004), 275, pp. 1-12.

Beigene Co., Ltd., "Phase I Clinical Research to Evaluate Safety, Tolerability and Pharmacokinetics/Pharmacodynamics Characteristics of BTK Inhibitor, BGB-3111, in Treating Chinese B Lymphocyte Tumor Patients," [Online], May 2016, Retrieved from the Internet: http://www.chinadrugtrials.org.cn/clinicaltrials.searchlistdetail.dhtml, Retrieved on: Mar. 21, 2022, 17 pages (with Machine Translation).

Beigene, "Efficacy and Safety of Zanubrutinib in Relapsed or Refractory Chronic Lymphocytic Leukemia/Small Lymphocytic Lymphoma," [Online], Retrieved from the Internet:< url:< a=""href= "https://clinicaltrials.gov/ct2/show/NCT03206918">https://clinicaltrials.gov/ct2/show/NCT03206918, Jul. 2017, 10 pages.</url:>.

Bellmunt, J. et al., "Keynote-045: open-label, phase II study of pembrolizumab versus investigator's choice of paclitaxel, docetaxel, or vinflunine for previously treated advanced urothelial cancer," Journal for ImmunoTherapy of Cancer, 2016, 4(Suppl. 2):91, Presented at 31st Society for Immunotherapy of Cancer Annual Meeting, Nov. 9-13, 2016, National Harbor, MD, 1 page.

(56) References Cited

OTHER PUBLICATIONS

Bellmunt, J. et al., "Pembrolizumab as Second-Line Therapy for Advanced Urothelial Carcinoma," N. Engl. J. Med., vol. 376, No. 11, Mar. 2017, pp. 1015-1026.

Bellmunt, J. et al., "Randomized Phase III Study Comparing Paclitaxel/Cisplatin/Gemcitabine and Gemcitabine/Cisplatin in Patients with Locally Advanced or Metastatic Urothelial Cancer Without Prior Systemic Therapy: EORTC Intergroup Study 30987," J Clin Oncol., Apr. 1, 2012;30(10):1107-1113.

Berger, R. et al., "Phase I safety and pharmacokinetic study of CT-011, a humanized antibody interacting with PD-1, in patients with advanced hematologic malignancies," Clinical Cancer Research, 14(10):3044-3051 (May 2008).

Boyd et al., "Deep sequencing and human antibody repertoire analysis," Current Opinion in Immunology (Jun. 2016) Vo. 40, pp. 103-109. Epub Apr. 8, 2016.

Brahmer, J. R. et al., "Safety and Activity of Anti-PD-L1 Antibody in Patients with Advanced Cancer," N Engl J Med. (Jun. 28, 2012), 366(26):2455-2465.

Brahmer, J. R. et al., "Phase I study of single-agent anti-programmed death-1 (MDX-1106) in refractory solid tumors: safety, clinical activity, pharmacodynamics, and immunologic correlates," J Clin Oncol. Jul. 1, 2010;28(19):3167-3175.

Brand, F-X et al., "Prospect for anti-HER2 receptor therapy in breast cancer," Anticancer Research, 26:463-470 (2006).

Caira, "Crystalline polymorphism of organic compounds," Topics Curr Chem. Jan. 1, 1998;198:163-208.

Cartigny, D. et al., "General Asymmetric Hydrogenation of 2-Alkyl- and 2-Aryl-Substituted Quinoxaline Derivatives Catalyzed by Iridium-Difluorphos: Unusual Halide Effect and Synthetic Application," J. Org. Chem., Apr. 2012, vol. 77, No. 10, pp. 4544-4556.

Casset, F. et al., "A peptide mimetic of an anti-CD4 monoclonal antibody by rational design," Biochemical and Biophysical Research Communications, vol. 307, pp. 198-205 (2003).

Clynes, R. A. et al., "Inhibitory Fc receptors modulate in vivo cytoxicity against tumor targets," Nat. Med. 6(4):443-446 (Apr. 2000).

Conroy, et al., "Antibodies: From novel repertoires to defining and refining the structure of biologically important targets," Methods (Mar. 2017); 116:12-22. Epub Jan. 11, 2017.

Dahan, R. et al., "FcRs Modulate the Anti-tumor Activity of Antibodies Targeting the PD-1/PD-L1 Axis," Cancer Cell (Sep. 2015), 28(3):285-95. doi: 10.1016/j.ccell.2015.08.004.

Damschroder et al., "Analysis of human and primate CD2 molecules by protein sequence and epitope mapping with anti-human CD2 antibodies," Mol Immunol. (Aug. 2004), 41(10):985-1000.

De Pascalis, et al., "Grafting of "Abbreviated" Complementarity-Determining Regions Containing Specificity-Determining Residues Essential for Ligand Contact to Engineer a Less Immunogenic Humanized Monoclonal Antibody," The Journal of Immunology, Sep. 15, 2002, 169(6): 3076-3084.

De Toni, E. N. et al., "Tapering of Immunosuppression and Sustained Treatment With Nivolumab in a Liver Transplant Recipient," Gastroenterology, May 2017;152(6):1631-1633. doi: 10.1053/j.gastro.2017.01.063.

Desai, J. et al., "Updated safety, efficacy, and pharmacokinetics (PK) results from thephase I study of BGB-A317, an anti-programmed death-1 (PD-1) mAb in patients with advanced solid tumors," J. Immunother. Cancer, 2016; 4(Suppl 1):P154, 2 pages.

Dorfman, D. M. et al., "Programmed death-1 (PD-1) is a marker of germinal center-associated T Cells and angioimmunoblastic T-cell lymphoma," American Journal of Surgical Pathology, 30(7):802-810 (Jul. 2006).

El-Khoueiry, A. B. et al., "Nivolumab in patients with advanced hepatocellular carcinoma (CheckMate 040): an open-label, non-comparative, phase 1/2 dose escalation and expansion trial," Lancet (Jun. 2017) vol. 389, No. 10088, pp. 2492-2502.

European Search Report for European Application No. 16167542.6, dated Nov. 14, 2016, 5 pages.

Extended European Search Report for European Application No. 15815646.3, dated Dec. 21, 2017, 10 pages.

Extended European Search Report for European Application No. 17841107.0, dated Feb. 21, 2020, 12 pages.

Extended European Search Report for European Application No. 17841172.4, dated Mar. 5, 2020, 6 pages.

Extended European Search Report for European Application No. 18744173.8, dated Oct. 21, 2020, 12 pages.

Extended European Search Report for European Application No. 18823691.3, dated Feb. 22, 2021, 9 pages.

Ferrara et al., "Recombinant renewable polyclonal antibodies." mABs (2015); 7(1):32-41.

Fuller, M. J. et al., "Immunotherapy of chronic hepatitis C virus infection with antibodies against programmed cell death-1 (PD-1)," Proceedings of the National Academy of Sciences, 110(37):15001-15006 (Sep. 2013).

Galsky, M. D. et al.," Effectiveness of Adjuvant Chemotherapy for Locally Advanced Bladder Cancer," J Clin Oncol. Mar. 10, 2016;34(8):825-832.

Gelderman, K. A. et al., "Complement function in mAb-mediated cancer immunotherapy," Trends in Immunology, 25(3):158-164 (Mar. 2004).

Hamid, O. et al., "Safety and tumor responses with lambrolizumab (Anti-PD-1) in melanoma," New England Journal of Medicine, 369(2):134-144 (Jul. 2013).

Hirayama, Y., "Handbook for organic compound crystal—Principle and know-how," 2008, 28 pages.

"History of Changes for Study: NCT02690558. Phase 2 Study Of Pembrolizumab In Combination With Gemcitabine And Cisplatin As Neoadjuvant Therapy," NCT02690558, Mar. 10, Mar. 2017, Retrieved from the Internet: URL:https://clinicaltrials.gov/ct2/history/NCT02690558?V_4=View#StudyPageTop, 5 pages.

International Search Report and Written Opinion for International Application No. PCT/CN2013/083467, dated Jun. 16, 2014, 9 pages.

International Search Report and Written Opinion for International Application No. PCT/CN2015/083066, dated Sep. 24, 2015, 8 pages.

International Search Report and Written Opinion for International Application No. PCT/CN2018/074108, dated Apr. 23, 2018, 12 pages.

International Search Report and Written Opinion for International Application No. PCT/CN2018/092827, dated Sep. 29, 2018, 14 pages.

International Search Report and Written Opinion for International Application No. PCT/CN2018/100145, dated Nov. 14, 2018, 8 pages.

International Search Report and Written Opinion for International Application No. PCT/US2018/063068, dated Feb. 27, 2019, 7 pages.

International Search Report for International Application No. PCT/CN2020/095352, dated Sep. 16, 2020, 23 pages.

International Search Report for International Application No. PCT/CN2020/095353, dated Sep. 15, 2020, 23 pages.

International Search Report for International Application No. PCT/US2019/017313, dated Jun. 25, 2019, 16 pages.

InvivoGen Insight, "IgG-Fc Engineering For Therapeutic Use," Apr./May 2006, 4 pages.

James, L. K. et al., "Potential Mechanisms for IgG4 Inhibition of Immediate Hypersensitivity Reactions," Curr Allergy Asthma Rep., 2016; 16:23, 7 pages. Published online Feb. 18, 2016. doi: 10.1007/s11882-016-0600-2.

Jiao, Y. et al., "Advances in the research of the anti-cancer agent—Raf kinase inhibitor," Strait Pharmaceutical Journal, vol. 19, No. 8, 2007, pp. 1-5 (with English Abstract).

Jie, L., "Deuterated Drugs Progress," Chemical Engineering Design Communication Medicine and Chemical Industry, 2016, vol. 42 (4), pp. 199.

Kersseboom, R. et al., "Constitutive activation of Bruton's tyrosine kinase induces the formation of autoreactive IgM plasma cells," Eur. J. Immunol. (2010) 40:2643-2654.

Khan et al., "Cross-neutralizing anti-HIV-1 human single chain variable fragments (scFvs) against CD4 binding site and N332

(56) References Cited

OTHER PUBLICATIONS glycan identified from a recombinant phage library." Scientific Reports (2017); Article No. 45163, 12 pages.
Konitzer et al., "Generation of a highly diverse panel of antagonistic chicken monoclonal antibodies against the GIP receptor," mABs (Apr. 2017); 9(3):536-549. Epub Jan. 5, 2017.
Kudo, M., Immune Checkpoint Blockade in Hepatocellular Carcinoma: 2017 Update, Liver Cancer, Nov. 2016; 6(1):1-12.
Kudo, M., "Immune Checkpoint Inhibition in Hepatocellular Carcinoma: Basics and Ongoing Clinical Trials," Oncology, 2017;92 Suppl 1, pp. 50-62. doi: 10.1159/000451016. Epub Feb. 2, 2017.
Lee et al., "Molecular-level analysis of the serum antibody repertoire in young adults before and after seasonal influenza vaccination." Nat Med. (Dec. 2016); 22(12):1456-1464. Epub Nov. 7, 2016.
Lund, J. et al., "Multiple interactions of IgG with its core oligosaccharide can modulate recognition by complement and human Fc gamma receptor I and influence the synthesis of its oligosaccharide chains," J Immunol., Dec. 1, 1996, 157(11):4963-4969.
Luo, J. et al., "Modern Physical Pharmaceutics Theory and Practice," Shang Hai Science and Technology Literature Publishing House, Apr. 2005, pp. 293-295.
Office Action for Japanese Application No. 2019-508889, dated Jun. 22, 2021, 7 pages.
Pan, Z. et al., "Discovery of Selective Irreversible Inhibitors for Bruton's Tyrosine Kinase," ChemMedChem 2007, vol. 2, pp. 58-61.
Panka D.J., et al., "Variable Region Framework Differences Result in Decreased or Increased Affinity of Variant Anti-Digoxin Antibodies," Proceedings of the National Academy of Sciences of the United States of America, May 1988, vol. 85 (9), pp. 3080-3084.
Parola et al., "Integrating high-throughput screening and sequencing for monoclonal antibody discovery and engineering." Immunology (Jan. 2018); 153(1):31-41. Epub Oct. 30, 2017.
Paul, W. E. (Ed.), Chap. 9, Structure and Function of Immunoglobulins, In: Fundamental Immunology, Third Edition, pp. 292-295, 1993.
Piao, C-Y et al., "Lamivudine treatment in patients with HBV-related hepatocellular carcinoma-using an untreated, matched control cohort," Acta Med. Okayama, vol. 59, No. 5, pp. 217-224 (2005).
Plimack, E. R. et al., "Pembrolizumab (MK-3475) for advanced urothelial cancer: Updated results and biomarker analysis from KEYNOTE-012," J. Clin. Oncol., vol. 33, Issue 15 Suppl., May 2015, Abstract 4502, 2 pages.
Presta, L. G. et al., "Engineering therapeutic antibodies for improved function," Biochemical Society Transactions (2002) vol. 30, Part 4, pp. 487-490.
Rudikoff, S. et al., "Single amino acid substitution altering antigen-binding specificity," Proc. Natl. Acad. Sci. USA, 79:1979-1983 (Mar. 1, 1982).
Samonakis, D. N. et al., "Systemic treatment for hepatocellular carcinoma: Still unmet expectations," World J Hepatol., Jan. 2017; 9(2):80-90.
Sequence Alignment, 2014, 1 page.
Sharma, P. et al., "Efficacy and safety of nivolumab monotherapy in metastatic urothelial cancer (mUC): Results from the phase I/II CheckMate 032 study," J. Clin. Oncol., vol. 34, No. 15 Suppl., May 2016, pp. 4501.
Sharma, P. et al., "Nivolumab monotherapy in recurrent metastatic urothelial carcinoma (CheckMate 032): a multicentre, open-label, two-stage, multi-arm, phase 1/2 trial," Lancet Oncol., Nov. 2016, vol. 17, No. 11, pp. 1590-1598.
Sheehan et al., "Phage and Yeast Display." Microbial. Spectr. (2015); 3(1):AID-0028-2014; 17 pages.
Shields, et al., "High Resolution Mapping of the Binding Site on Human IgG1 for FcRI, FCRII, FCRIII, and FcRn and Design of IgG1 Variants with Improved Binding to the FcR*," J. Biol. Chem. (2001); 276: 6591-6604.
Shioji, Y., "Production Technology of Solid Preparations," Tokyo, CMC Publication, Jan. 27, 2003, Popular Edition, pp. 9 and 12-13.
Singhal, D. et al., "Drug polymorphism and dosage form design: a practical perspective," Advanced Drug Delivery Reviews, 56 (2004) pp. 335-347.
Smith, K. G. et al., "FcRIIB in autoimmunity and infection: evolutionary and therapeutic implications," Nat Rev Immunol. May 2010;10(5):328-43.
Stave, J. W. et al., "Antibody and antigen contact residues define epitope and paratope size and structure," The Journal of Immunology, vol. 191, Jan. 2013, pp. 1428-1435.
Strome, et al., "A Mechanistic Perspective of Monoclonal Antibodies in Cancer Therapy Beyond Target-Related Effects". The Oncologist (Sep. 2007); 12(9):1084-1095.
Supplementary Partial European Search Report for European Application No. 13893636.4, dated Feb. 28, 2017, 13 pages.
Sznol, M. et al., "Antagonist antibodies to PD-1 and B7-H1 (PD-L1) in the treatment of advanced human cancer," Clinical Cancer Research, 19(5):1021-1034 (Mar. 2013).
Takada, N., "Bulk Drug Form Screening and Selection at Drug Discovery Phase," Pharm Stage, Jan. 2007, vol. 6, No. 10, pp. 20-25.
Takayama, T. et al., "Effects of the novel and potent lymphocyte-specific protein tyrosine kinase inhibitor TKM0150 on mixed lymphocyte reaction and contact hypersensitivity in mice," Arzneimit-telforschung, 60(5):282-285 (2010).
Takayama, T. et al., "Ring-fused pyrazole derivatives as potent inhibitors of lymphocyte-specific kinase (Lck): Structure, synthesis, and SAR," Bioorganic & Medicinal Chemistry Letters, 20(1):112-116 (Jan. 2010).
Tam, C. S. et al., "A head-to-head Phase III study comparing zanubrutinib versus ibrutinib in patients with Waldenström macroglobulinemia," Future Oncology, vol. 14, No. 22, Sep. 2018, pp. 2229-2237.
Topalian, S. L., "Safety, Activity, and Immune Correlates of Anti-PD-1 Antibody in Cancer," N. Engl. J. Med., Jun. 2012; vol. 366, No. 26, pp. 2443-2454.
Van Regenmortel, M. H. V., "Development of a Preventive HIV Vaccine Requires Solving Inverse Problems Which Is Unattainable by Rational Vaccine Design." Front Immunol. (Jan. 2018); 8:2009, 11 pages.
Wang C., et al., "In Vitro Characterization of The Anti-PD-1 Antibody Nivolumab, BMS-936558, and in Vivo Toxicology in Non-Human Primates," Cancer Immunology Research, Sep. 2014, vol. 2 (9), pp. 846-856.
Wanich, N. et al., "High prevalence of hepatocellular carcinoma in patients with chronic hepatitis B infection in Thailand," Asian Pac J Cancer Prev, vol. 17, No. 6, pp. 2857-2860 (2016).
Wherry, E. J., "T cell exhaustion," Nature Immunology 12(6):492-499 (2011). Published online May 18, 2011.
Wu, H. et al. "Humanization of a Murine monoclonal antibody by simultaneous optimization of framework and CDR residues", Journal of Molecular Biology (1999); 294.1:151-162.
Xu, D. et al., "In vitro characterization of five humanized OKT3 effector function variant antibodies," Cell Immunol. Feb. 25, 2000;200(1):16-26.
Yen, C-J et al., "Preliminary results of a phase 1A/1B study of BGB-A317, an anti-PD-1 monoclonal antibody (mAb), in patients with advanced hepatocellular carcinoma (HCC)," Abstract P-140, Annals of Oncology, vol. 28, Supplement 3, p. 54 (2017).
Zhou et al., "Structural Repertoire of HIV-1-Neutralizing Antibodies Targeting the CD4 Supersite in 14 Donors." Cell (Jun. 2015); 161(6):1280-1292.
An, S. et al., "Small-molecule PROTACs: An emerging and promising approach for the development of targeted therapy drugs," EBioMedicine, Oct. 2018, vol. 36, pp. 553-562.
Ardley, H. C. et al., "E3 ubiquitin ligases," Essays Biochem., 2005, vol. 41, pp. 15-30.
Benson, D. M., Jr. et al., "The PD-1/PD-L1 axis modulates the natural killer cell versus multiple myeloma effect: a therapeutic target for CT-011, a novel monoclonal anti-PD-1 antibody," Blood, 116(13):2286-2294 (Sep. 2010).
Buhimschi, A. D., "Targeting the C481S Ibrutinib-Resistance Mutation in Bruton's Tyrosine Kinase Using PROTAC-Mediated Degradation," Biochemistry, vol. 57, No. 26, Jul. 2018, pp. 3564-3575.

(56) References Cited

OTHER PUBLICATIONS

Cermakova, K. et al., "Next-Generation Drugs and Probes for Chromatin Biology: From Targeted Protein Degradation to Phase Separation," Molecules, Aug. 2018, vol. 23, No. 1958, 26 pages.
Crews, C. M., "Inducing Protein Degradation as a Therapeutic Strategy," Jan. 2018, 61(2):403-404.
Dobrovolsky, D. et al., "Bruton tyrosine kinase degradation as a therapeutic strategy for cancer," Blood, Feb. 2019, 133(9):952-961.
Grice, G. L. et al., "The Proteasome Distinguishes between Heterotypic and Homotypic Lysine-11-Linked Polyubiquitin Chains," Cell Rep., Jul. 2015, 12(4):545-553.
International Search Report and Written Opinion for International Application No. PCT/CN2020/103988, dated Oct. 27, 2020, 14 pages.
Komander, D. et al., "The ubiquitin code," Annu. Rev. Biochem., 2012, vol. 81, pp. 203-229.
Lebraud, H. et al., "Protein degradation: a validated therapeutic strategy with exciting prospects," Essays Biochem., Nov. 2017, 61(5):517-527.
Lochmuller, C. H. et al., "Chromatographic resolution of enantiomers selective review," J. Chromatogr., vol. 113, No. 3, Oct. 1975, pp. 283-302.
Lu, J. et al., "Hijacking the E3 Ubiquitin Ligase Cereblon to Efficiently Target BRD4," Chem Biol., Jun. 2015, 22(6):755-763.
Lu, M. et al., "Discovery of a Keap1-dependent peptide PROTAC to knockdown Tau by ubiquitination-proteasome degradation pathway," Eur J Med Chem., Feb. 2018, vol. 146, pp. 251-259.
Neklesa, T. K. et al., "Targeted protein degradation by PROTACs," Pharmacol. Ther., Jun. 2017, vol. 174, pp. 138-144.
Ottis, P. et al., "Assessing Different E3 Ligases for Small Molecule Induced Protein Ubiquitination and Degradation," ACS Chem. Biol., Oct. 2017, 12(10):2570-2578.
Ottis, P. et al., "Proteolysis-Targeting Chimeras: Induced Protein Degradation as a Therapeutic Strategy," ACS Chem. Biol., Apr. 2017, 12(4):892-898.
Sakamoto, K. M., "Chimeric molecules to target proteins for ubiquitination and degradation," Methods Enzymol., vol. 399, Dec. 2005, pp. 833-847.
Sakamoto, K. M. et al., "Protacs: chimeric molecules that target proteins to the Skp1-Cullin-F box complex for ubiquitination and degradation," Proc Natl Acad Sci USA, Jul. 2001, 98(15):8554-8559.
Sun, Y. et al., "Degradation of Bruton's tyrosine kinase mutants by PROTACs for potential treatment of ibrutinib-resistant non-Hodgkin lymphomas," Leukemia, Mar. 2019, 33:2105-2110.
Sun, Y. et al., Letter to the Editor, "PROTAC-induced BTK degradation as a novel therapy for mutated BTK C481S induced ibrutinib-resistant B-cell malignancies," Cell Research, Jul. 2018, 28(7):779-781.
Swatek, K. N. et al., "Ubiquitin modifications," Cell Res., Apr. 2016, vol. 26, No. 4, pp. 399-422.
Toure et al. "Small-Molecule PROTACS: New Approaches to Protein Degradation" Angew Chern Int Ed Engl. (20 16) ;55(6):1966-1973.
Wenzel, S-S et al., "MCL1 is deregulated in subgroups of diffuse large B-cell lymphoma," Leukemia, vol. 27, pp. 1381-1390 (2013).
Zhou, P. et al., "Harnessing the ubiquitination machinery to target the degradation of specific cellular proteins," Mol. Cell., Sep. 2000;6(3):751-756.
Zorba, A. et al., "Delineating the role of cooperativity in the design of potent PROTACs for BTK," PNAS, Jun. 2018, 115(31):E7285-E7292.
Brinckerhoff, Courtenay C., "A Fresh Look At The Lead Compound Analysis," PharmaPatents, Foley & Lardner LLP, Jan. 22, 2019, 4 pages.
Buske, C. et al., "A Head-to-Head Phase 3 Study Comparing BGB-3111 and Ibrutinib in Patients With Waldenström Macroglobulinemia," Hematological Oncology, 2017, 35: 422-423.

ClinicalTrials.gov Identifier: NCT03053440, A Study Comparing BGB-3111 and Ibrutinib in Subjects With Waldenström's Macroglobulinemia (WM) (Aug. 8, 2017), 12 pages.
ClinicalTrials.gov Identifier: NCT03145064, Study of BTK Inhibitor BGB-3111 in Subjects With Relapsed/Refractory Non-GCB Type Diffuse Large B Cell Lymphoma (May 5, 2017), 5 pages.
ClinicalTrials.gov Identifier: NCT03189524, A Study to Investigate Zanubrutinib in Chinese Participants With B-cell Lymphoma (Jun. 15, 2017), 5 pages.
ClinicalTrials.gov Identifier: NCT03206970, Study to Evaluate Efficacy and Safety of BGB-3111 in Participants With Relapsed or Refractory Mantle Cell Lymphoma (MCL) (Jul. 3, 2017), 6 pages.
Eng, Melissa C., "United States: Selecting a Lead Compound: A Balancing Act In The Chemical Obviousness Inquiry," Mondaq, Mar. 8, 2018, retrieved from the Internet on Nov. 28, 2022, https://www.mondaq.com/unitedstates/patent/680778/selecting-a-lead-compound-a-balancing-act-in-the-chemical-obviousness-inquiry, 2 pages.
Hu, Nan, et al., "BTK inhibitor BGB-3111 demonstrates anti-tumor activity in solid tumor models." Cancer Research 77.13_Supplement (2017): 2010-2010.
"International Nonproprietary Names for Pharmaceutical Substances (INN)," WHO Drug Information, vol. 31, No. 2, 2017, pp. 241-242, 355.
Miller, Cary, "Prior Art Chemical Structures Must be More Than a 'Code Name'," Jones Day, Apr. 18, 2018, retrieved online Nov. 28, 2022, https://www.ptablitigationblog.com/prior-art-chemical-structures-must-be-more-than-a-code-name/.
Noonan, Kevin E., "Novartis Pharmaceuticals Corp. v. West-Ward Pharmaceuticals Int'l (Fed. Cir. 2019)," Patent Docs, May 16, 2019, retrieved from the internet on Nov. 28, 2022, https://www.patentdocs.org/2019/05/novartis-pharmaceuticals-corp-v-west-ward-pharmaceuticals-intl-fed-cir-2019.html.
Seymour, J. F., et al., "High Overall Response Rate with the BTK Inhibitor BGB-3111 in Patients with Chronic Lymphocytic Leukemia/Small Lymphocytic Lymphoma: An Update on Safety and Activity," Hematological Oncology, 35: 234-235.
Tam, C. et al.,"The BTK Inhibitor, Bgb-3111, Is Safe, Tolerable, and Highly Active in Patients with Relapsed/ Refractory B-Cell Malignancies: Initial Report of a Phase 1 First-in-Human Trial," Blood, 2015, vol. 126 (23), 8 pages.
Tam, C. S. et al., "Phase 1 study of the selective BTK inhibitor zanubrutinib in B-cell malignancies and safety and efficacy evaluation in CLL," The American Society of Hematology, vol. 134, No. 11, pp. 851-859 (2019).
Tam, C.S. et al., "Clinical pharmacology and PK/PD translation of the second-generation Bruton's tyrosine kinase inhibitor, zanubrutinib," Expert Review of Clinical Pharmacology, 2021, vol. 14:11, pp. 1329-1344.
Tam, C.S. et al., "High Major Response Rate, Including Very Good Partial Responses (VGPR), in Patients (pts) with Waldenstrom Macroglobulinemia (WM) Treated with the Highly Specific BTK Inhibitor Bgb-3111: Expansion Phase Results from an Ongoing Phase I Study," Blood 2016; 128 (22): 1216.
Tam, C.S. et al., Twice Daily Dosing with the Highly Specific BTK Inhibitor, Bgb-3111, Achieves Complete and Continuous BTK Occupancy in Lymph Nodes, and Is Associated with Durable Responses in Patients (pts) with Chronic Lymphocytic Leukemia (CLL)/Small Lymphocytic Lymphoma (SLL). Blood 2016; 128 (22): 642. doi: https://doi.org/10.1182/blood.V128.22.642.642.
Wu, J. et al., "Second-generation inhibitors of Bruton tyrosine kinase," J Hematol Oncol. Sep. 2, 2016;9(1):80.
Atkinson, B. T., "Tec regulates platelet activation by GPVI in the absence of Btk," Blood, Nov. 15, 2003, vol. 102, Issue 19, pp. 3592-3599.
Byrd, J. C. et al., "Acalabrutinib (ACP-196) in Relapsed Chronic Lymphocytic Leukemia," N. Engl. J. Med., 2016, vol. 374, pp. 323-332.
Byrd, J. C. et al., "Targeting BTK with Ibrutinib in Relapsed Chronic Lymphocytic Leukemia," N. Engl. J. Med., 2013, vol. 369, pp. 32-42.

(56) References Cited

OTHER PUBLICATIONS

Byrd, J. C. et al., "Three-year follow-up of treatment-naive and previously treated patients with CLL and SLL receiving single-agent ibrutinib," Blood, Apr. 15, 2015, vol. 125, Issue 16, pp. 2497-2506.

Chen, J. et al., "Impact of Bruton'S Tyrosine Kinase Inhibitors On Collagen-Induced Platelet Aggregation: A Pharmacokinetic/Pharmacodynamic Perspective," EHA Learning Center, Meeting Abstract 2016, 4 pages.

Di Paolo et al., "Specific Btk inhibition suppresses B cell- and myeloid cell-mediated arthritis," Nat. Chern. Biol., 2011, vol. 7, pp. 41-50.

Kaur, V. et al., "Ibrutinib in CLL: a focus on adverse events, resistance, and novel approaches beyond ibrutinib," Ann. Hematol., 2017, vol. 96(7), pp. 1175-1184.

Li et al., "Skin toxicities associated with epidermal growth factor receptor inhibitors," Target Oncol. 2009, vol. 4(2), pp. 107-119.

Melosky et al., "Supportive Care Treatments for Toxicities of Anti-EGFR and Other Targeted Agents," Curr. Oncol. 19 (Suppl 1), 2012, pp. 59-63.

Raedler, L. A., "Farydak (Panobinostat): First HDAC Inhibitor Approved for Patients with Relapsed Multiple Myeloma," Am. Health Drug Benefits, Mar. 2016, vol. 9, pp. 84-87.

Wang, M. L. et al., "Targeting BTK with Ibrutinib in Relapsed or Refractory Mantle-Cell Lymphoma," N. Engl. J. Med., Aug. 8, 2013, vol. 369, pp. 507-516.

\* cited by examiner

TREATMENT OF B CELL CANCERS USING A COMBINATION COMPRISING BTK INHIBITORS

CROSS-REFERENCE TO RELATED APPLICATIONS

This application is the U.S. national stage application to International Patent Application No. PCT/CN2017/098023, filed Aug. 18, 2017, which claims the benefit of priority to International Application No. PCT/CN2016/096082 filed on Aug. 19, 2016, the entire contents of each of which are incorporated herein by reference.

DESCRIPTION OF THE TEXT FILE SUBMITTED ELECTRONICALLY

The contents of the text file submitted electronically herewith are incorporated herein by reference in their entirety: A computer readable format copy of the Sequence Listing (filename: BEIG_018_01US_SeqList.txt, date recorded: Feb. 13, 2019, file size 79 kilobytes).

FIELD OF THE INVENTION

Disclosed herein is a method for the prevention, delay of progression or treatment of cancer in a subject, comprising administering to the subject in need thereof a Btk inhibitor (in particularly (S)-7-(1-acryloylpiperidin-4-yl)-2-(4-phenoxyphenyl)-4,5,6,7-tetrahydropyrazolo-[1,5-a]pyrimidine-3-carboxamide or a pharmaceutically acceptable salt thereof) in combination with an immune checkpoint inhibitor or a targeted therapy agent. Disclosed herein is also a pharmaceutical combination comprising a Btk inhibitor (in particularly (S)-7-(1-acryloylpiperidin-4-yl)-2-(4-phenoxyphenyl)-4,5,6,7-tetra-hydropyrazolo[1,5-a]pyrimidine-3-carboxamide or a pharmaceutically acceptable salt thereof) in combination with an immune checkpoint inhibitor, or a targeted therapy agent and the use thereof.

BACKGROUND OF THE INVENTION

Bruton's tyrosine kinase (Btk) belongs to the Tec family of cytoplasmic tyrosine kinases, which is the second largest family of non-receptor kinases in humans [Vetrie et al., Nature 361: 226-233, 1993; Bradshaw, Cell Signal. 22: 1175-84, 2010]. It is expressed in all cell lineages of the hematopoietic system, except for T cells and is localized in bone marrow, spleen and lymph node tissue [Smith et al., J. Immunol. 152: 557-565, 1994]. Inactivating mutations in the gene encoding Btk cause X-linked agammaglobulinemia (XLA) in humans and X-linked immunodeficiency (XID) in mice [Conley et al., Annu. Rev. Immunol. 27: 199-227, 2009]. Both diseases are characterized by dramatic defects in B cell development and function, suggesting the essential role of Btk for B cell development and function. In addition, constitutive activation of Btk in B cells results in the accumulation of autoreactive plasma cells [Kersseboom et al., Eur J Immunol. 40:2643-2654, 2010]. Btk is activated by upstream Src-family kinases in BCR signaling pahway. Once activated, Btk in turn phosphorylates phospholipase-Cγ (PLCγ), leading to Ca$^{2+}$ mobilization and activation of NF-κB and MAP kinase pathways. These proximal signaling events promote expression of genes involved in proliferation and survival [Humphries et al., J. Biol. Chem. 279: 37651, 2004]. In addition to its essential regulatory role as downstream of BCR, Btk activity also plays a critical role in FcR signaling. Signaling via FcRγ associated receptors also promotes Btk-dependent proinflammatory cytokine production by cells such as macrophages [Di Paolo et al., Nat. Chem. Biol. 7: 41-50, 2011]. Btk has been an important target due to its proximal location in the BCR and FcR signaling pathways. Preclinical studies show that Btk deficient mice are resistant to developing collagen-induced arthritis. Moreover, clinical studies of Rittman, a CD20 antibody to deplete mature B-cells, reveal the key role of B-cells in a number of inflammatory diseases such as rheumatoid arthritis, systemic lupus erythematosus and multiple sclerosis [Gurcan et al., Int. Immunopharmacol. 9: 10-25, 2009]. In addition, aberrant activating of Btk plays important role in pathogenesis of B-cell lymphomas indicating that inhibition of Btk is useful in the treatment of hematological malignancies [Davis et al., Nature 463: 88-92, 2010].

In addition, aberrant activation of Btk plays an important role in pathogenesis of B-cell lymphomas indicating that inhibition of Btk is useful in the treatment of hematological malignancies [Davis et al., Nature 463: 88-92, 2010)]. The covalent BTK inhibitor ibrutinib (PCI-32765, Imbruvica®) was approved by the US Food and Drug Administration for the treatment of chronic lymphocytic leukemia (CLL), mantle cell lymphoma (MCL) and Waldenstrom's macroglobulinemia (WM).

WO2014/173289A1 disclosed a series of fused heterocyclic compounds having the following general Formula (I) or a stereoisomer thereof, or a pharmaceutically acceptable salt thereof as Btk inhibitors, which have demonstrated potent inhibitory activity against Bruton's tyrosine kinase.

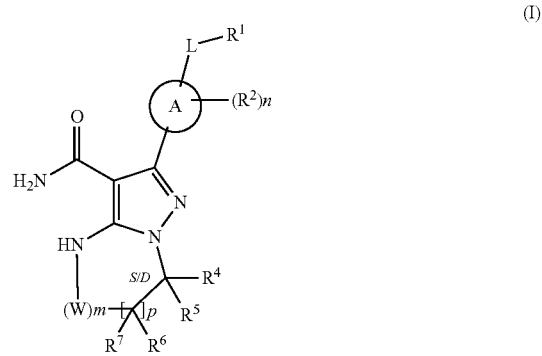

The unpublished PCT application PCT/CN2016/095510 disclosed a crystalline form of the Btk inhibitor in WO 2014/173289 A1, particularly, (S)-7-(1-acryloylpiperidin-4-yl)-2-(4-phenoxyphenyl)-4,5,6,7-tetra-hydropyrazolo[1,5-a] pyrimidine-3-carboxamide (hereinafter Compound 1) for the treatment of cancers with aberrations in the B-cell receptor (BCR) and FcR signaling pathway in which Btk plays important roles. Compound 1 has demonstrated to have potent and irreversible inhibitory activities against Btk.

Compound 1

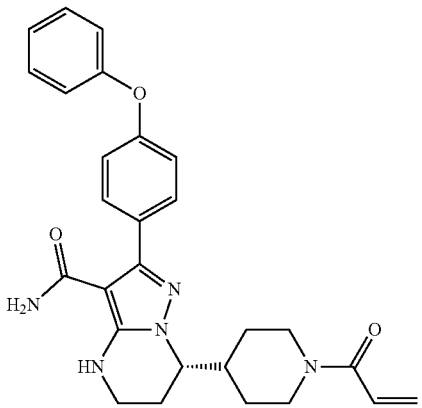

The inventors of the present application have found that the combination of a Btk inhibitor (in particular, the above-mentioned Compound 1) with an immunotherapy agent or a targeted therapy agent produces significant inhibition of tumor growth in cancers with aberrations in the B-cell receptor as compared with the monotherapy of each of the above active pharmaceutical agent alone.

SUMMARY OF THE INVENTION

In a first aspect, disclosed herein is a method for the prevention, delay of progression or treatment of cancer in a subject, comprising administering to the subject in need thereof a therapeutically effective amount of a Btk inhibitor of Formula (I) or a stereoisomer thereof, or a pharmaceutically acceptable salt thereof, in combination with a therapeutically effective amount of an immune checkpoint inhibitor or a targeted therapy agent.

In a second aspect, disclosed herein is a pharmaceutical combination for use in the prevention, delay of progression or treatment of cancer, comprising a Btk inhibitor of Formula (I) or a stereoisomer thereof, or a pharmaceutically acceptable salt thereof, in combination with an immune checkpoint inhibitor or a targeted therapy agent.

In a third aspect, disclosed herein is a Btk inhibitor of Formula (I) or a stereoisomer thereof, or a pharmaceutically acceptable salt thereof, for use in the prevention, delay of progression or treatment of cancer in combination with an immune checkpoint inhibitor or a targeted therapy agent. In one embodiment of this aspect, disclosed herein is an immune checkpoint inhibitor or a targeted therapy agent for use in the prevention, delay of progression or treatment of cancer in combination with a Btk inhibitor of Formula (I) or a stereoisomer thereof, or a pharmaceutically acceptable salt thereof.

In a fourth aspect, disclosed herein is a use of a pharmaceutical combination in the manufacture of a medicament for use in the prevention, delay of progression or treatment of cancer, said pharmaceutical combination comprising a Btk inhibitor of Formula (I) or a stereoisomer thereof, or a pharmaceutically acceptable salt thereof, and an immune checkpoint inhibitor or a targeted therapy agent.

In a fifth aspect, disclosed herein is an article of manufacture, or "kit" comprising a first container, a second container and a package insert, wherein the first container comprises at least one dose of a medicament comprising a Btk inhibitor of Formula (I) or a stereoisomer thereof, or a pharmaceutically acceptable salt thereof, the second container comprises at least one dose of a medicament comprising an immune checkpoint inhibitor or a targeted therapy agent, and the package insert comprises instructions for treating cancer a subject using the medicaments.

The method and pharmaceutical combination disclosed herein, as a combination therapy, produce significantly more efficacious than either single agent.

In an embodiment of each of the above five aspects, the targeted therapy agent is an antibody. In an embodiment of each of the above five aspects, the targeted therapy agent is an anti-CD20 antibody. In some other embodiments of each of the above five aspects, the immune checkpoint inhibitor is an antibody. In an embodiment of each of the above five aspects, the immune check point inhibitor is an inhibitor of PD-1, PD-L1, PD-L2, TIM-3, Gal-9, CTLA-4, CD80, CD86, A2AR, B7-H3, B7-H4, BTLA, HVEM, IDO1, IDO2, TDO, LAG3, VISTA, KIR, 2B4, CD2, CD27, CD28, CD30, CD40, CD90, CD137, CD226, DR³, GITR, ICOS, LAIR¹, LIGHT, MARCO, PS, OX-40, SLAM TIGHT, CTCNI, or any combinations thereof. In an embodiment of each of the above five aspects, the immune checkpoint inhibitor is a monoclonal antibody. In an embodiments of each of the above five aspects, the immune checkpoint inhibitor is an inhibitor of PD-1.

In an embodiment of each of the above five aspects, the cancer is a hematologic cancer. In an embodiment of each of the above five aspects, the hematologic cancer is a leukemia, a lymphoma, a myeloma, a non-Hodgkin's lymphoma (NHL), a Hodgkin's lymphoma (HL), or a B-cell malignancy. In an embodiments of each of the above five aspects, the hematologic cancer is a B-cell malignancy. In an embodiments of each of the above five aspects, the B-cell malignancy is chronic lymphocytic leukemia (CLL), small lymphocytic lymphoma (SLL), follicular lymphoma (FL), mantle cell lymphoma (MCL), marginal zone lymphoma (MZL), Waldenstrom macroglobulinemia (WM), Hairy cell leukemia (HCL), Burkitt's-like leukemia (BL), B cell pro-lymphocytic leukemia (B-PLL), diffuse large B cell lymphoma (DLBCL), germinal center B-cell diffuse large B-cell lymphoma (GCB-DLBCL), non-germinal center B-cell diffuse large B-cell lymphoma (non-GCB DLBCL), DLBCL with undetermined subtype, primary central nervous system lymphoma (PCNSL), secondary central nervous system lymphoma (SCNSL) of breast or testicular origin, multiple myeloma, extranodal marginal zone B cell lymphoma, nodal marginal zone B cell lymphoma, Burkitt's lymphoma, non-Burkitt high grade B cell lymphoma, primary mediastinal B-cell lymphoma (PMBL), immunoblastic large cell lymphoma, precursor B-lymphoblastic lymphoma, B cell pro-lymphocytic leukemia, lymphoplasmacytic lymphoma, splenic marginal zone lymphoma, plasma cell myeloma, plasmacytoma, mediastinal (thymic) large B cell lymphoma, intravascular large B cell lymphoma, primary effusion lymphoma, lymphomatoid granulomatosis, or a combination thereof. In an embodiment of each of the above five aspects, the B-cell malignancy is diffuse large B-cell lymphoma (DLBCL). In an embodiments of each of the above five aspects, DLBCL is activated B-cell diffuse large B-cell lymphoma (ABC-DLBCL), GCB-DLBCL or Non-GCB DLBCL. In an embodiment of each of the above five aspects, the B-cell malignancy is chronic lymphocytic leukemia (CLL), small lymphocytic lymphoma (SLL), B cell prolymphocytic leukemia (B-PLL), non-CLL/SLL lymphoma, follicular lymphoma (FL), mantle cell lymphoma (MCL), marginal zone lymphoma (MZL), Waldenstrom's macroglobulinemia (WM), multiple myeloma or a combination thereof. In an embodiment of each of the above five aspects, the B-cell malignancy is a relapsed or refractory (R/R) B-cell malignancy. In an embodiment of each of the above five aspects, the relapsed or refractory B-cell malignancy is diffuse large B-cell lymphoma (DLBCL). In an embodiments of each of the above five aspects, the relapsed or refractory DLBCL is activated B-cell diffuse large B-cell lymphoma (ABC-DLBCL), GCB-DLBCL or Non-GCB DLBCL. In an embodiment of each of the above five aspects, the relapsed or refractory (R/R) B-cell malignancy is diffuse large B-cell lymphoma (DLBCL), chronic lymphocytic leukemia (CLL), small lymphocytic lymphoma (SLL), B cell prolymphocytic leukemia (B-PLL), non-CLL/SLL lymphoma, follicular lymphoma (FL), mantle cell lymphoma (MCL), marginal zone lymphoma (MZL), Waldenstrom's macroglobulinemia (WM), multiple myeloma, or a combination thereof. In an embodiment of each of the above five aspects, the B-cell malignancy is a metastasized B-cell malignancy. In an embodiment of each of the above five aspects, the metastasized B-cell malignancy is diffuse large B-cell lymphoma (DLBCL), chronic lymphocytic leukemia (CLL), small lymphocytic lymphoma (SLL), B cell prolymphocytic leukemia (B-PLL), non-CLL/SLL lymphoma, follicular lymphoma (FL), mantle cell lymphoma (MCL), marginal zone lymphoma (MZL), Waldenstrom's macroglobulinemia (WM), multiple myeloma or a combination thereof.

In an embodiment of each of the above five aspects, the cancer is a sarcoma, or carcinoma. In an embodiments of each of the above five aspects, the cancer is selected from anal cancer; appendix cancer; bile duct cancer (i.e., cholangiocarcinoma); bladder cancer; breast cancer; cervical cancer; colon cancer; cancer of Unknown Primary (CUP); esophageal cancer; eye cancer; fallopian tube cancer; gastroenterological cancer; kidney cancer; liver cancer; lung cancer; medulloblastoma; melanoma; oral cancer; ovarian cancer; pancreatic cancer; parathyroid disease; penile cancer; pituitary tumor; prostate cancer; rectal cancer; skin cancer; stomach cancer; testicular cancer; throat cancer; thyroid cancer; uterine cancer; vaginal cancer; vulvar cancer; or a combination thereof. In an embodiment of each of the above five aspects, the cancer is selected from bladder cancer, breast cancer, colon cancer, gastroenterological cancer, kidney cancer, lung cancer, ovarian cancer, pancreatic cancer, prostate cancer, proximal or distal bile duct cancer, melanoma, or a combination thereof. In an embodiment of each of the above five aspects, the colon cancer is adenocarcinoma, gastrointestinal carcinoid tumors, gastrointestinal stromal tumors, primary colorectal lymphoma, leiomyosarcoma, melanoma, squamous cell-carcinoma, mucinous adenocarcinoma, Signet ring cell adenocarcinoma, or a combination thereof. In an embodiment of each of the above five aspects, the cancer is a relapsed or refractory cancer. In an embodiment of each of the above five aspects, the relapsed or refractory cancer is selected from bladder cancer, breast cancer, colon cancer, gastroenterological cancer, kidney cancer, lung cancer, ovarian cancer, pancreatic cancer, prostate cancer, proximal or distal bile duct cancer, melanoma, or a combination thereof. In an embodiment of each of the above five aspects, the cancer is a metastasized cancer. In embodiments of each of the above five aspects, the metastasized cancer is selected from bladder cancer, breast cancer, colon cancer, gastroenterological cancer, kidney cancer, lung cancer, ovarian cancer, pancreatic cancer, prostate cancer, proximal or distal bile duct cancer, and melanoma.

In an embodiment of each of the above five aspects, the BTK inhibitor is (S)-7-(1-acryloylpiperidin-4-yl)-2-(4-phenoxyphenyl)-4,5,6,7-tetra-hydropyrazolo[1,5-a]pyrimidine-3-carboxamide (Compound 1), or a pharmaceutically acceptable salt thereof. In an embodiment of each of the above five aspects, the Btk inhibitor and the immune checkpoint inhibitor, or a targeted therapy agent, are administered simultaneously, sequentially or intermittently.

DETAILED DESCRIPTION OF THE INVENTION

Figure 1:
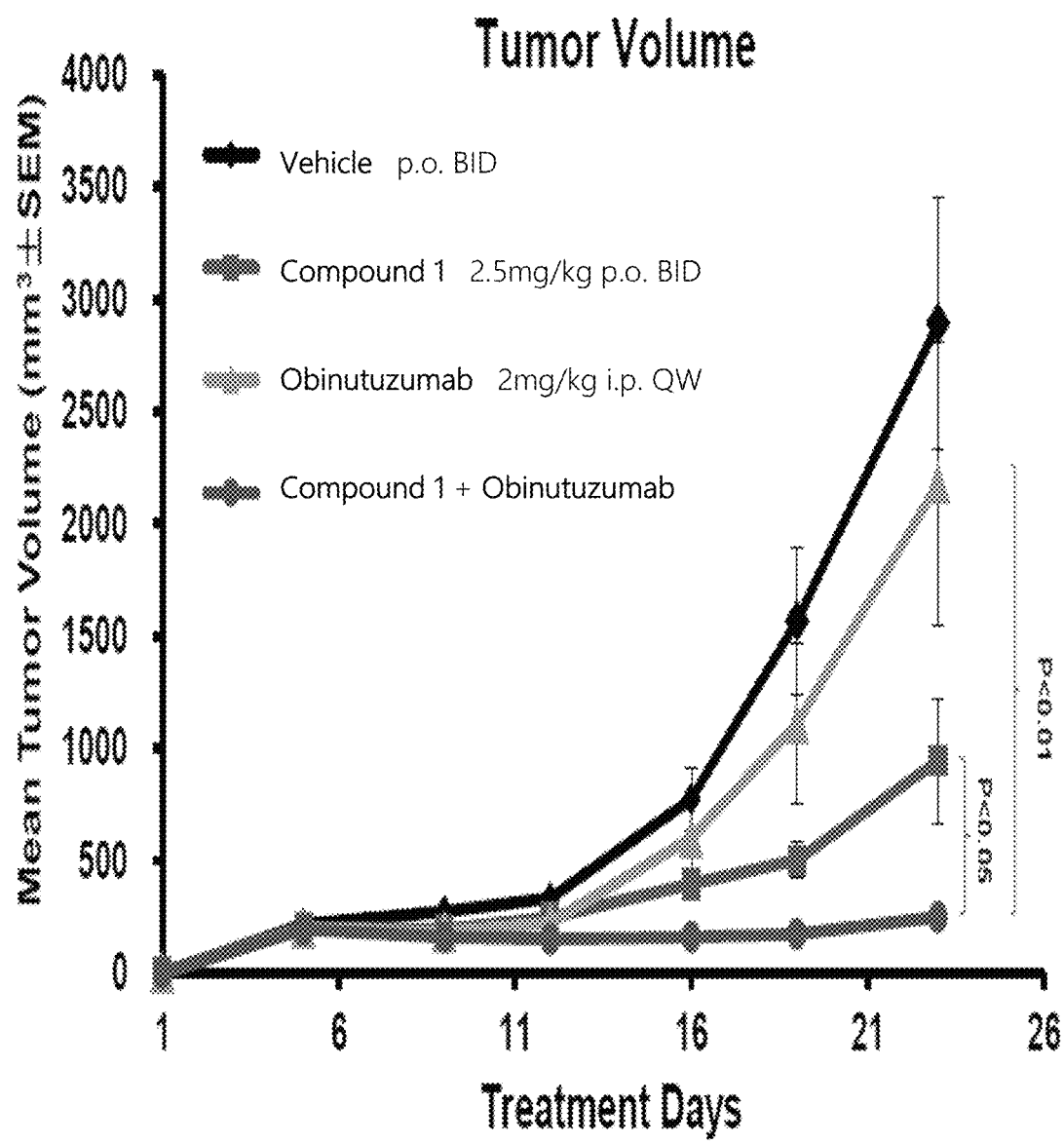
FIG. 1 shows the combination effect of Compound 1 and anti-CD20 mAb (obinutuzumab) on tumor growth in REC-1/NK92MI MCL xenograft model.

Abbreviations (1):

| | |
|---|---|
| ABC-DLBCL | Activated B-cell diffuse large B-cell lymphoma |
| A2AR | Adenosine A2A receptor |
| B-PLL | B cell prolymphocytic leukemia |
| Btk | Bruton's Tyrosine Kinase |
| BTLA | B and T Lymphocyte Attenuator, CD272 |
| CDR | Complementarity Determining Region |
| CLL | chronic lymphocytic leukemia |
| CTLA-4 | Cytotoxic T-Lymphocyte-Associated protein 4, CD152 |
| DLBCL | diffuse large B-cell lymphoma |
| DMEM | Dulbecco minimum essential medium |
| HVEM | Herpesvirus Entry Mediator |
| non-CLL/SLL | non-chronic lymphocytic leukemia/small lymphocytic lymphoma |
| IDO | Indoleamine 2,3-dioxygenase |
| TDO | Tryptophan 2,3-dioxygenase |
| IG | immunoglobulin G |
| i.p. | Intraperitoneal or Intraperitoneally |
| KIR | Killer-cell Immunoglobulin-like Receptor |
| LAG3 | Lymphocyte Activation Gene-3 |
| mAb | Monoclonal antibodies |
| NK | Natural killer |
| PBMC | Peripheral blood mononuclear cell |
| PBS | Phosphate Buffered Saline |

| | |
|---|---|
| PD-1 | Programmed Death 1 protein, Pdcd-1, CD279 |
| p.o. | "by mouth" or "per os" |
| QD | Once daily |
| Q4D | Once every four days |
| QW | Once weekly |
| Q2W | Once every two weeks |
| Q3W | Once every three weeks |
| SLL | small lymphocytic lymphoma |
| TIM-3 | T-cell Immunoglobulin domain and Mucin domain 3 |
| Vh | Heavy chain variable region |
| Vl | Light chain variable region |
| VISTA | V-domain Ig suppressor of T-cell activation |

Abbreviations (2):

| | |
|---|---|
| ACN | acetonitrile |
| AcOH | Acetic acid |
| D-DBTA | (2S, 3S)-Dibenzoyl tartaric acid |
| DCM | Dichloromethane |
| DMF | N, N-dimethylformamide |
| DMF-DMA | N, N-dimethylformamide dimethyl acetal |
| EA | Ethyl Acetate |
| EDCI | 1-Ethyl-3-(3-dimethylaminopropyl)carbodiimide |
| EtOAc | ethyl acetate |
| HOBt | Hydroxybenzotriazole |
| HPLC | High Performance Liquid Chromatography |
| L-DBTA | (2R, 3R)-Dibenzoyl tartaric acid |
| MeCN | Acetonitrile |
| MeOH | Methanol |
| MeMgBr | Methyl Magnesium Bromide |
| MsOH | Methanesulfonic Acid |
| MTBE | Methyl tertiary butyl ether |
| NLT | not less than |
| NMR | Nuclear Magnetic Resonance |
| NMT | not more than |
| Pd | Palladium |
| pH | Hydrogen ion concentration |
| RT | Room Temperature |
| TEA | Triethylamine |
| XRPD | X-ray Powder Diffraction |

Definitions

Unless specifically defined elsewhere in this document, all other technical and scientific terms used herein have the meaning commonly understood by one of ordinary skill in the art to which this invention belongs.

As used herein, including the appended claims, the singular forms of words such as "a", "an", and "the", include their corresponding plural references unless the context clearly indicates otherwise.

The term "or" is used to mean, and is used interchangeably with, the term "and/or" unless the context clearly dictates otherwise.

Throughout this specification and the claims which follow, unless the context requires otherwise, the word "comprise", and variations such as "comprises" and "comprising", will be understood to imply the inclusion of an active agent (e.g., a mAb or a Btk inhibitor) or a stated amino acid sequence, but not the exclusion of any other active ingredient or amino acid sequence. When used herein the term "comprising" can be interchangeable with the term "containing" or "including".

The term "alkyl" refers to a hydrocarbon group selected from linear and branched saturated hydrocarbon groups of 1-18, or 1-12, or 1-6 carbon atoms. Examples of the alkyl group include methyl, ethyl, 1-propyl or n-propyl ("n-Pr"), 2-propyl or isopropyl ("i-Pr"), 1-butyl or n-butyl ("n-Bu"), 2-methyl-1-propyl or isobutyl ("i-Bu"), 1-methylpropyl or s-butyl ("s-Bu"), and 1,1-dimethylethyl or t-butyl ("t-Bu"). Other examples of the alkyl group include 1-pentyl, 2-pentyl, 3-pentyl, 2-methyl-2-butyl, 3-methyl-2-butyl, 3-methyl-1-butyl, 2-methyl-1-butyl, 1-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl and 3,3-dimethyl-2-butyl groups. Lower alkyl means 1-8, preferably 1-6, more preferably 1-4 carbon atoms; lower alkenyl or alkynyl means 2-8, 2-6 or 2-4 carbon atoms.

The term "alkenyl" refers to a hydrocarbon group selected from linear and branched hydrocarbon groups comprising at least one C=C double bond and of 2-18, or 2-12, or 2-6 carbon atoms. Examples of the alkenyl group may be selected from ethenyl or vinyl, prop-1-enyl, prop-2-enyl, 2-methylprop-1-enyl, but-1-enyl, but-2-enyl, but-3-enyl, buta-1,3-dienyl, 2-methylbuta-1,3-diene, hex-1-enyl, hex-2-enyl, hex-3-enyl, hex-4-enyl, and hexa-1,3-dienyl groups.

The term "alkynyl" refers to a hydrocarbon group selected from linear and branched hydrocarbon group, comprising at least one CC triple bond and of 2-18, or 2-12, or 2-6 carbon atoms. Examples of the alkynyl group include ethynyl, 1-propynyl, 2-propynyl (propargyl), 1-butynyl, 2-butynyl, and 3-butynyl groups.

The term "cycloalkyl" refers to a hydrocarbon group selected from saturated and partially unsaturated cyclic hydrocarbon groups, comprising monocyclic and polycyclic (e.g., bicyclic and tricyclic) groups. For example, the cycloalkyl group may be of 3-12, or 3-8, or 3-6 carbon atoms. Even further for example, the cycloalkyl group may be a monocyclic group of 3-12, or 3-8, or 3-6 carbon atoms. Examples of the monocyclic cycloalkyl group include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, cyclohexadienyl, cycloheptyl, cyclooctyl, cyclononyl, cyclodecyl, cycloundecyl, and cyclododecyl groups. Examples of the bicyclic cycloalkyl groups include those having 7-12 ring atoms arranged as a bicycle ring selected from [4,4], [4,5], [5,5], [5,6] and [6,6] ring systems, or as a bridged bicyclic ring selected from bicyclo[2.2.1]heptane, bicyclo[2.2.2]octane, and bicyclo[3.2.2]nonane. The ring may be saturated or have at least one double bond (i.e. partially unsaturated), but is not fully conjugated, and is not aromatic, as aromatic is defined herein.

The term "Aryl" herein refers to a group selected from:5- and 6-membered carbocyclic aromatic rings, for example, phenyl; bicyclic ring systems such as 7-12 membered bicyclic ring systems wherein at least one ring is carbocyclic and aromatic, selected, for example, from naphthalene, and indane; and tricyclic ring systems such as 10-15 membered tricyclic ring systems wherein at least one ring is carbocyclic and aromatic, for example, fluorene. For example, the aryl group is selected from 5- and 6-membered carbocyclic aromatic rings fused to a 5- to 7-membered cycloalkyl or heterocyclic ring optionally comprising at least one heteroatom selected from N, O, and S, provided that the point of attachment is at the carbocyclic aromatic ring when the carbocyclic aromatic ring is fused with a heterocyclic ring, and the point of attachment can be at the carbocyclic aromatic ring or at the cycloalkyl group when the carbocyclic aromatic ring is fused with a cycloalkyl group. Bivalent radicals formed from substituted benzene derivatives and having the free valences at ring atoms are named as substituted phenylene radicals. Bivalent radicals derived from univalent polycyclic hydrocarbon radicals whose names end in "-yl" by removal of one hydrogen atom from the carbon atom with the free valence are named by adding "-idene" to the name of the corresponding univalent radical, e.g., a naphthyl group with two points of attachment is termed naphthylidene. Aryl, however, does not encompass or overlap with heteroaryl, separately defined below. Hence, if one or more carbocyclic aromatic rings are fused with a heterocyclic aromatic ring, the resulting ring system is heteroaryl, not aryl, as defined herein.

The term "halogen" or "halo" refers to F, Cl, Br or I.

The term "heteroalkyl" refers to alkyl comprising at least one heteroatom.

The term "heteroaryl" refers to a group selected from: 5- to 7-membered aromatic, monocyclic rings comprising 1, 2, 3 or 4 heteroatoms selected from N, O, and S, with the remaining ring atoms being carbon; 8- to 12-membered bicyclic rings comprising 1, 2, 3 or 4 heteroatoms, selected from N, O, and S, with the remaining ring atoms being carbon and wherein at least one ring is aromatic and at least one heteroatom is present in the aromatic ring; and 11- to 14-membered tricyclic rings comprising 1, 2, 3 or 4 heteroatoms, selected from N, O, and S, with the remaining ring atoms being carbon and wherein at least one ring is aromatic and at least one heteroatom is present in an aromatic ring. For example, the heteroaryl group includes a 5- to 7-membered heterocyclic aromatic ring fused to a 5- to 7-membered cycloalkyl ring. For such fused, bicyclic heteroaryl ring systems wherein only one of the rings comprises at least one heteroatom, the point of attachment may be at the heteroaromatic ring or at the cycloalkyl ring. When the total number of S and O atoms in the heteroaryl group exceeds 1, those heteroatoms are not adjacent to one another. In some embodiments, the total number of S and O atoms in the heteroaryl group is not more than 2. In some embodiments, the total number of S and O atoms in the aromatic heterocycle is not more than 1. Examples of the heteroaryl group include, but are not limited to, (as numbered from the linkage position assigned priority 1) pyridyl (such as 2-pyridyl, 3-pyridyl, or 4-pyridyl), cinnolinyl, pyrazinyl, 2,4-pyrimidinyl, 3,5-pyrimidinyl, 2,4-imidazolyl, imidazopyridinyl, isoxazolyl, oxazolyl, thiazolyl, isothiazolyl, thiadiazolyl, tetrazolyl, thienyl, triazinyl, benzothienyl, furyl, benzofuryl, benzoimidazolyl, indolyl, isoindolyl, indolinyl, phthalazinyl, pyrazinyl, pyridazinyl, pyrrolyl, triazolyl, quinolinyl, isoquinolinyl, pyrazolyl, pyrrolopyridinyl (such as 1H-pyrrolo[2,3-b]pyridin-5-yl), pyrazolopyridinyl (such as 1H-pyrazolo[3,4-b]pyridin-5-yl), benzoxazolyl (such as benzo[d]oxazol-6-yl), pteridinyl, purinyl, 1-oxa-2,3-diazolyl, 1-oxa-2,4-diazolyl, 1-oxa-2,5-diazolyl, 1-oxa-3,4-diazolyl, 1-thia-2,3-diazolyl, 1-thia-2,4-diazolyl, 1-thia-2,5-diazolyl, 1-thia-3,4-diazolyl, furazanyl, benzofurazanyl, benzothiophenyl, benzothiazolyl, benzoxazolyl, quinazolinyl, quinoxalinyl, naphthyridinyl, furopyridinyl, benzothiazolyl (such as benzo[d]thiazol-6-yl), indazolyl (such as 1H-indazol-5-yl) and 5,6,7,8-tetrahydroisoquinoline.

The term "heterocyclic" or "heterocycle" or "heterocyclyl" refers to a ring selected from 4- to 12-membered monocyclic, bicyclic and tricyclic, saturated and partially unsaturated rings comprising at least one carbon atoms in addition to 1, 2, 3 or 4 heteroatoms, selected from oxygen, sulfur, and nitrogen. "Heterocycle" also refers to a 5- to 7-membered heterocyclic ring comprising at least one heteroatom selected from N, O, and S fused with 5-, 6-, and/or 7-membered cycloalkyl, carbocyclic aromatic or heteroaromatic ring, provided that the point of attachment is at the heterocyclic ring when the heterocyclic ring is fused with a carbocyclic aromatic or a heteroaromatic ring, and that the point of attachment can be at the cycloalkyl or heterocyclic ring when the heterocyclic ring is fused with cycloalkyl.

The "Heterocycle" also refers to an aliphatic spirocyclic ring comprising at least one heteroatom selected from N, O, and S, provided that the point of attachment is at the heterocyclic ring. The rings may be saturated or have at least one double bond (i.e. partially unsaturated). The heterocycle may be substituted with oxo. The point of the attachment may be carbon or heteroatom in the heterocyclic ring. A heterocyle is not a heteroaryl as defined herein. Examples of the heterocycle include, but not limited to, (as numbered from the linkage position assigned priority 1) 1-pyrrolidinyl, 2-pyrrolidinyl, 2,4-imidazolidinyl, 2,3-pyrazolidinyl, 1-piperidinyl, 2-piperidinyl, 3-piperidinyl, 4-piperidinyl, 2,5-piperazinyl, pyranyl, 2-morpholinyl, 3-mo holinyl, oxiranyl, aziridinyl, thiiranyl, azetidinyl, oxetanyl, thietanyl, 1,2-dithietanyl, 1,3-difhietanyl, dihydropyridinyl, tetrahydropyridinyl, thiomorpholinyl, thioxanyl, piperazinyl, homopiperazinyl, homopiperidinyl, azepanyl, oxepanyl, thiepanyl, 1,4-oxathianyl, 1,4-dioxepanyl, 1,4-oxafhiepanyl, 1,4-oxaazepanyl, 1,4-dithiepanyl, 1,4-fhiazepanyl and 1,4-diazepane 1,4-dithianyl, 1,4-azathianyl, oxazepinyl, diazepinyl, thiazepinyl, dihydrofhienyl, dihydropyranyl, dihydrofuranyl, tetrahydrofuranyl, tetrahydrothienyl, tetrahydropyranyl, tetrahydrothiopyranyl, 1-pyrrolinyl, 2-pyrrolinyl, 3-pyrrolinyl, indolinyl, 2H-pyranyl, 4H-pyranyl, 1,4-dioxanyl, 1,3-dioxolanyl, pyrazolinyl, pyrazolidinyl, dithianyl, difhiolanyl, pyrazolidinylimidazolinyl, pyrimidinonyl, 1,1-dioxo-thiomoholinyl, 3-azabicyco[3.1.0] hexanyl, 3-azabicyclo[4.1.0]heptanyl and azabicyclo[2.2.2] hexanyl. Substituted heterocycle also includes ring systems substituted with one or more oxo moieties, such as piperidinyl N-oxide, morpholinyl-N-oxide, 1-oxo-1-thiomorpholinyl and 1, 1-dioxo-1-thiomorpholinyl.

Substituents are selected from: halogen, —R$^a$, —OR$^a$, =O, =NR$^a$, =N—OR$^a$, —NR$^a$R$^b$, —SW, —SiR$^a$R$^a$R$^b$, —OC(O)R$^a$, —C(O)R$^a$, —CO$_2$R$^a$, —CONR$^a$R$^b$, —OC(O)NR$^a$R$^b$, —NR$^b$C(O)R$^a$, —NR$^a$—C(O)NR$^b$R$^b$, —NR$^a$—SO$_2$NR$^b$, —NR$^b$CO$_2$R$^a$, —NH—C(NH$_2$)=NH, —NR$^a$C(NH$_2$)=NH, —NH—C(NH$_2$)=NR$^a$, —S(O)R$^a$, —SO$_2$R$^a$, —SO$_2$NR$^a$R$^b$, —NR$^b$SO$_2$R, —CN and —NO$_2$, —N$_3$, —CH(Ph)$_2$, perfluoro(C$_1$-C$_4$)alkoxy and perfluoro(C$_1$-C$_4$)alkyl, in a number ranging from zero to three, with those groups having zero, one or two substituents being particularly preferred. R$^a$, R$^b$ and R$^c$ each independently refer to hydrogen, unsubstituted (C$_1$-C$_8$)alkyl and heteroalkyl, unsubstituted aryl, aryl substituted with one to three halogens, unsubstituted alkyl, alkoxy or thioalkoxy groups, or aryl-(C$_1$-C$_4$)alkyl groups. When R$^a$ and R$^b$ are attached to the same nitrogen atom, they can be combined with the nitrogen atom to form a 5-, 6- or 7-membered ring. Hence, —NR$^a$R$^b$ includes 1-pyrrolidinyl and 4-morpholinyl, "alkyl" includes groups such as trihaloalkyl (e.g., —CF$_3$ and —CH$_2$CF$_3$), and when the aryl group is 1,2,3,4-tetrahydronaphthalene, it may be substituted with a substituted or unsubstituted (C$_3$-C$_7$)spirocycloalkyl group. The (C$_3$-C$_7$)spirocycloalkyl group may be substituted in the same manner as defined herein for "cycloalkyl". Preferred substituents are selected from: halogen, —R$^a$, —OR$^a$, =O, —NR$^a$R$^b$, —SR$^a$, —SiR$^a$R$^a$R$^b$, —OC(O)R$^a$, —C(O)R$^a$, —CO$_2$R$^a$, —CONR$^a$R$^b$, —OC(O)NR$^a$R$^b$, —NR$^b$C(O)R$^a$, —NR$^b$CO$_2$R$^a$, —NR$^a$—SO$_2$NR$^b$R$^b$, —S(O)R$^a$, —SO$_2$R$^a$, —SO$_2$NR$^a$R$^b$, —NR$^b$SO$_2$R, —CN and —NO$_2$, perfluoro(C$_1$-C$_4$)alkoxy and perfluoro(C$_1$-C$_4$)alkyl, where R$^a$ and R$^b$ are as defined above.

The term "fused ring" herein refers to a polycyclic ring system, e.g., a bicyclic or tricyclic ring system, in which two rings share only two ring atoms and one bond in common. Examples of fused rings may comprise a fused bicyclic cycloalkyl ring such as those having from 7 to 12 ring atoms arranged as a bicyclic ring selected from [4,4], [4,5], [5,5], [5,6] and [6,6] ring systems as mentioned above; a fused bicyclic aryl ring such as 7 to 12 membered bicyclic aryl ring systems as mentioned above, a fused tricyclic aryl ring such as 10 to 15 membered tricyclic aryl ring systems mentioned above; a fused bicyclic heteroaryl ring such as 8- to 12-membered bicyclic heteroaryl rings as mentioned above, a fused tricyclic heteroaryl ring such as 11- to 14-membered tricyclic heteroaryl rings as mentioned above; and a fused bicyclic or tricyclic heterocyclyl ring as mentioned above.

When compounds contain olefin double bonds, unless specified otherwise, such double bonds are meant to include both E and Z geometric isomers.

Some of the compounds may exist with different points of attachment of hydrogen, referred to as tautomers. For example, compounds including carbonyl —$CH_2C(O)$— groups (keto forms) may undergo tautomerism to form hydroxyl —CH=C(OH)— groups (enol forms). Both keto and enol forms, individually as well as mixtures thereof, are also intended to be included where applicable.

The term "Pharmaceutically acceptable salts" include, but are not limited to salts with inorganic acids, selected, for example, from hydrochlorates, phosphates, diphosphates, hydrobromates, sulfates, sulfinates, and nitrates; as well as salts with organic acids, selected, for example, from malates, maleates, fumarates, tartrates, succinates, citrates, lactates, methanesulfonates, p-toluenesulfonates, 2-hydroxyethylsulfonates, benzoates, salicylates, stearates, alkanoates such as acetate, and salts with HOOC—$(CH_2)_n$—COOH, wherein n is selected from 0 to 4. Similarly, examples of pharmaceutically acceptable cations include, but are not limited to, sodium, potassium, calcium, aluminum, lithium, and ammonium.

In addition, if a compound is obtained as an acid addition salt, the free base can be obtained by basifying a solution of the acid salt. Conversely, if the product is a free base, an addition salt, such as a pharmaceutically acceptable addition salt, may be produced by dissolving the free base in a suitable organic solvent and treating the solution with an acid, in accordance with conventional procedures for preparing acid addition salts from base compounds. Those skilled in the art will recognize various synthetic methodologies that may be used without undue experimentation to prepare non-toxic pharmaceutically acceptable addition salts.

The terms "administration", "administering", "treating" and "treatment" herein, when applied to an animal, human, experimental subject, cell, tissue, organ, or biological fluid, mean contact of an exogenous pharmaceutical, therapeutic, diagnostic agent, or composition to the animal, human, subject, cell, tissue, organ, or biological fluid. Treatment of a cell encompasses contact of a reagent to the cell, as well as contact of a reagent to a fluid, where the fluid is in contact with the cell. The term "administration" and "treatment" also means in vitro and ex vivo treatments, e.g., of a cell, by a reagent, diagnostic, binding compound, or by another cell. The term "subject" herein includes any organism, preferably an animal, more preferably a mammal (e.g., rat, mouse, dog, cat, rabbit) and most preferably a human.

An "effective amount" refers to an amount of at least one compound and/or at least one stereoisomer thereof, and/or at least one pharmaceutically acceptable salt thereof effective to "treat" a disease or disorder in a subject, and that will elicit, to some significant extent, the biological or medical response of a tissue, system, animal or human that is being sought, such as when administered, is sufficient to prevent development of, or alleviate to some extent, one or more of the symptoms of the condition or disorder being treated. The therapeutically effective amount will vary depending on the compound, the disease and its severity and the age, weight, etc., of the mammal to be treated.

The term "at least one substituent" includes, for example, from 1 to 4, such as from 1 to 3, further as 1 or 2, substituents. For example, "at least one substituent $R^{16}$" herein includes from 1 to 4, such as from 1 to 3, further as 1 or 2, substituents selected from the list of R<16> as described herein.

The term "antibody" herein is used in the broadest sense and specifically covers antibodies (including full length monoclonal antibodies) and antibody fragments so long as they recognize antigen, such as, a target antigen (e.g., CD20) or an immune checkpoint (e.g., PD-1). An antibody molecule is usually monospecific, but may also be described as idiospecific, heterospecific, or polyspecific. Antibody molecules bind by means of specific binding sites to specific antigenic determinants or epitopes on antigens.

The term "monoclonal antibody" or "mAb" or "Mab" herein means a population of substantially homogeneous antibodies, i.e., the antibody molecules comprised in the population are identical in amino acid sequence except for possible naturally occurring mutations that may be present in minor amounts. In contrast, conventional (polyclonal) antibody preparations typically include a multitude of different antibodies having different amino acid sequences in their variable domains, particularly their CDRs, which are often specific for different epitopes. The modifier "monoclonal" indicates the character of the antibody as being obtained from a substantially homogeneous population of antibodies, and is not to be construed as requiring production of the antibody by any particular method. Monoclonal antibodies (mAbs) may be obtained by methods known to those skilled in the art. See, for example, U.S. Pat. No. 4,376,110. The mAbs disclosed herein may be of any immunoglobulin class including IgG, IgM, IgD, IgE, IgA, and any subclass thereof. A hybridoma producing a mAb may be cultivated in vitro or in vivo. High titers of mAbs can be obtained in in vivo production where cells from the individual hybridomas are injected intraperitoneally into mice, such as pristine-primed Balb/c mice to produce ascites fluid containing high concentrations of the desired mAbs. MAbs of isotype IgM or IgG may be purified from such ascites fluids, or from culture supernatants, using column chromatography methods well known to those of skill in the art.

In general, the basic antibody structural unit comprises a tetramer. Each tetramer includes two identical pairs of polypeptide chains, each pair having one "light chain" (about 25 kDa) and one "heavy chain" (about 50-70 kDa). The amino-terminal portion of each chain includes a variable region of about 100 to 110 or more amino acids primarily responsible for antigen recognition. The carboxy-terminal portion of the heavy chain may define a constant region primarily responsible for effector function. Typically, human light chains are classified as kappa and lambda light chains. Furthermore, human heavy chains are typically classified as α, δ, ε, γ, or μ and define the antibody's isotypes as IgA, IgD, IgE, IgG, and IgM, respectively. Within light and heavy chains, the variable and constant regions are joined by a "J" region of about 12 or more amino acids, with the heavy chain also including a "D" region of about 10 more amino acids.

The variable regions of each light/heavy chain (Vl/Vh) pair form the antibody binding site. Thus, in general, an intact antibody has two binding sites. Except in bifunctional or bispecific antibodies, the two binding sites are, in general, the same.

Typically, the variable domains of both the heavy and light chains comprise three hypervariable regions, also called "complementarity determining regions (CDRs)", which are located between relatively conserved framework regions (FR). The CDRs are usually aligned by the framework regions, enabling binding to a specific epitope. In general, from N-terminal to C-terminal, both light and heavy chain variable domains comprise FR-1 (or FR1), CDR-1 (or CDR1), FR-2 (FR2), CDR-2 (CDR2), FR-3 (or FR3), CDR-3 (CDR3), and FR-4 (or FR4). The assignment of amino acids to each domain is, generally, in accordance with the definitions of Sequences of Proteins of Immunological Interest, Kabat, et al., *National Institutes of Health*, Bethesda, Md.; 5<m> ed.; NIH Publ. No. 91-3242 (1991); Kabat (1978) *Adv. Prot. Chem.* 32: 1-75; Kabat, et al., (1977) *J. Biol. Chem.* 252:6609-6616; Chothia, et al, (1987) *J. Mol. Biol.* 196:901-917 or Chothia, et al, (1989) *Nature* 342:878-883.

The term "hypervariable region" means the amino acid residues of an antibody that are responsible for antigen-binding. The hypervariable region comprises amino acid residues from a "complementarity determining region" or "CDR" (i.e., CDR-L1, CDR-L2 and CDR-L3 in the light chain variable domain and CDR-H1, CDR-H2 and CDR-H3 in the heavy chain variable domain). See, Kabat et al. (1991) *Sequences of Proteins of Immunological Interest, 5th Ed. Public Health Service, National Institutes of Health, Bethesda, Md.* (defining the CDR regions of an antibody by sequence); see also Chothia and Lesk (1987) *J. Mol. Biol.* 196: 901-917 (defining the CDR regions of an antibody by structure). The term "framework" or "FR" means those variable domain residues other than the hypervariable region residues defined herein as CDR residues.

Unless otherwise indicated, "antibody fragment" or "antigen-binding fragment" means antigen binding fragments of antibodies, i.e. antibody fragments that retain the ability to bind specifically to the antigen bound by the full-length antibody, e.g. fragments that retain one or more CDR regions. Examples of antigen binding fragments include, but not limited to, Fab, Fab', F(ab')2, and Fv fragments; diabodies; linear antibodies; single-chain antibody molecules, e.g., single chain Fv (ScFv); nanobodies and multispecific antibodies formed from antibody fragments.

An antibody that "specifically binds to" a specified target protein is an antibody that exhibits preferential binding to that target as compared to other proteins, but this specificity does not require absolute binding specificity. An antibody is considered "specific" for its intended target if its binding is determinative of the presence of the target protein in a sample, e.g. without producing undesired results such as false positives. Antibodies or binding fragments thereof, useful in the present invention will bind to the target protein with an affinity that is at least two fold greater, preferably at least ten times greater, more preferably at least 20-times greater, and most preferably at least 100-times greater than the affinity with non-target proteins. An antibody herein is said to bind specifically to a polypeptide comprising a given amino acid sequence, e.g. the amino acid sequence of a mature human PD-1 molecule, if it binds to polypeptides comprising that sequence but does not bind to proteins lacking that sequence.

The term "human antibody" herein means an antibody that comprises human immunoglobulin protein sequences only. A human antibody may contain murine carbohydrate chains if produced in a mouse, in a mouse cell, or in a hybridoma derived from a mouse cell. Similarly, "mouse antibody" or "rat antibody" mean an antibody that comprises only mouse or rat immunoglobulin protein sequences, respectively.

The term "humanized antibody" means forms of antibodies that contain sequences from non-human (e.g., murine) antibodies as well as human antibodies. Such antibodies contain minimal sequence derived from non-human immunoglobulin. In general, the humanized antibody will comprise substantially all of at least one, and typically two, variable domains, in which all or substantially all of the hypervariable loops correspond to those of a non-human immunoglobulin and all or substantially all of the FR regions are those of a human immunoglobulin sequence. The humanized antibody optionally also will comprise at least a portion of an immunoglobulin constant region (Fc), typically that of a human immunoglobulin. The prefix "hum", "hu", "Hu" or "h" is added to antibody clone designations when necessary to distinguish humanized antibodies from parental rodent antibodies. The humanized forms of rodent antibodies will generally comprise the same CDR sequences of the parental rodent antibodies, although certain amino acid substitutions may be included to increase affinity, increase stability of the humanized antibody, or for other reasons.

The terms "cancer" or "tumor" herein mean or describe the physiological condition involving abnormal cell growth with the potential to invade or spread to other parts of the body. The "disease" refers to any disease, discomfort, illness, symptoms or indications, and can be substituted with the term "disorder" or "condition".

In some embodiments, the cancer is a hematologic cancer. In some embodiments, the hematologic cancer is a leukemia, a lymphoma, a myeloma, a non-Hodgkin's lymphoma (NHL), a Hodgkin's lymphoma (HL), or a B-cell malignancy. In some embodiments, the hematologic cancer is a B-cell malignancy. In some embodiments, the B-cell malignancy is chronic lymphocytic leukemia (CLL), small lymphocytic lymphoma (SLL), follicular lymphoma (FL), mantle cell lymphoma (MCL), marginal zone lymphoma (MZL), Waldenstrom macroglobulinemia (WM), Hairy cell leukemia (HCL), Burkitt's-like leukemia (BL), B cell prolymphocytic leukemia (B-PLL), diffuse large B cell lymphoma (DLBCL), germinal center B-cell diffuse large B-cell lymphoma (GCB-DLBCL), non-germinal center B-cell diffuse large B-cell lymphoma (non-GCB DLBCL), DLBCL with undetermined subtype, primary central nervous system lymphoma (PCNSL), secondary central nervous system lymphoma (SCNSL) of breast or testicular origin, multiple myeloma, extranodal marginal zone B cell lymphoma, nodal marginal zone B cell lymphoma, Burkitt's lymphoma, non-Burkitt high grade B cell lymphoma, primary mediastinal B-cell lymphoma (PMBL), immunoblastic large cell lymphoma, precursor B-lymphoblastic lymphoma, B cell prolymphocytic leukemia, lymphoplasmacytic lymphoma, splenic marginal zone lymphoma, plasma cell myeloma, plasmacytoma, mediastinal (thymic) large B cell lymphoma, intravascular large B cell lymphoma, primary effusion lymphoma, lymphomatoid granulomatosis, or a combination thereof. In some embodiments, the B-cell malignancy is diffuse large B-cell lymphoma (DLBCL). In some embodiments, DLBCL is activated B-cell diffuse large B-cell lymphoma (ABC-DLBCL), GCB-DLBCL or Non-GCB DLBCL. In some embodiments, the B-cell malignancy is chronic lymphocytic leukemia (CLL), small lymphocytic lymphoma (SLL), B cell prolymphocytic leukemia (B-PLL), non-CLL/SLL lymphoma, follicular lymphoma (FL), mantle cell lymphoma (MCL), marginal zone lymphoma (MZL), Waldenstrom's macroglobulinemia (WM), multiple myeloma, or a combination thereof. In some embodiments, the B-cell malignancy is a relapsed or refractory (R/R) B-cell malignancy. In some embodiments, the relapsed or refractory (R/R) B-cell malignancy is diffuse large B-cell lymphoma (DLBCL). In some embodiments, the relapsed or refractory DLBCL is activated B-cell diffuse large B-cell lymphoma (ABC-DLBCL), GCB-DLBCL or Non-GCB DLBCL. In some embodiments, the relapsed or refractory (R/R) B-cell malignancy is chronic lymphocytic leukemia (CLL), small lymphocytic lymphoma (SLL), B cell prolymphocytic leukemia (B-PLL), non-CLL/SLL lymphoma, follicular lymphoma (FL), mantle cell lymphoma (MCL), marginal zone lymphoma (MZL), Waldenstrom's macroglobulinemia (WM), multiple myeloma, or a combination thereof. In some embodiments, the B-cell malignancy is a metastasized B-cell malignancy. In some embodiments, the metastasized B-cell malignancy is diffuse large B-cell lymphoma (DLBCL), chronic lymphocytic leukemia (CLL), small lymphocytic lymphoma (SLL), B cell prolymphocytic leukemia (B-PLL), non-CLL/SLL lymphoma, follicular lymphoma (FL), mantle cell lymphoma (MCL), marginal zone lymphoma (MZL), Waldenstrom's macroglobulinemia (WM), multiple myeloma, or a combination thereof. In some embodiments, the cancer is a sarcoma, or carcinoma. In some embodiments, the cancer is selected from anal cancer; appendix cancer; bile duct cancer (i.e., cholangiocarcinoma); bladder cancer; breast cancer; cervical cancer; colon cancer; cancer of Unknown Primary (CUP); esophageal cancer; eye cancer; fallopian tube cancer; gastroenterological cancer; kidney cancer; liver cancer; lung cancer; medulloblastoma; melanoma; oral cancer; ovarian cancer; pancreatic cancer; parathyroid disease; penile cancer; pituitary tumor; prostate cancer; rectal cancer; skin cancer; stomach cancer; testicular cancer; throat cancer; thyroid cancer; uterine cancer; vaginal cancer; or vulvar cancer; or a combination thereof. In some embodiments, the cancer is selected from bladder cancer, breast cancer, colon cancer, gastroenterological cancer, kidney cancer, lung cancer, ovarian cancer, pancreatic cancer, prostate cancer, proximal or distal bile duct cancer, melanoma, or a combination thereof. In some embodiments, the colon cancer is adenocarcinoma, gastrointestinal carcinoid tumors, gastrointestinal stromal tumors, primary colorectal lymphoma, leiomyosarcoma, melanoma, squamous cell-carcinoma, mucinous adenocarcinoma, Signet ring cell adenocarcinoma, or a combination thereof. In some embodiments, the cancer is a relapsed or refractory cancer. In some embodiments, the relapsed or refractory cancer is selected from bladder cancer, breast cancer, colon cancer, gastroenterological cancer, kidney cancer, lung cancer, ovarian cancer, pancreatic cancer, prostate cancer, proximal or distal bile duct cancer, melanoma, or a combination thereof. In some embodiments, the cancer is a metastasized cancer. In embodiments, the metastasized cancer is selected from bladder cancer, breast cancer, colon cancer, gastroenterological cancer, kidney cancer, lung cancer, ovarian cancer, pancreatic cancer, prostate cancer, proximal or distal bile duct cancer, and melanoma.

The term "CDRs" means complementarity determining region(s) in an immunoglobulin variable region, defined using the Kabat numbering system, unless otherwise indicated.

Immune Checkpoint Inhibitors

In some embodiments, the Btk inhibitor is co-administered with an immune checkpoint inhibitor, which is an inhibitor of PD-1, PD-L1, PD-L2, TIM-3, Gal-9, CTLA-4, CD80, CD86, A2AR, B7-H3, B7-H4, BTLA, BTLA, HVEM, IDO1, IDO2, TDO, LAG3, VISTA, KIR, 2B4, CD2, CD27, CD28, CD30, CD40, CD90, CD137, CD226, CD276, DR$^3$, GITR, ICOS, LAIR$^1$, LIGHT, MARCO, PS, OX-40, SLAM TIGHT, CTCNI, or a combination thereof.

"Immune checkpoints (checkpoint proteins)" are molecules in the immune system that either turn up a signal (co-stimulatory molecules) or turn down a signal. And they also regulate T-cell activation or function. Many cancers protect themselves from the immune system by inhibiting the T cell signal. An "immune checkpoint inhibitor", which totally or partially reduces, inhibits, interferes with or modulates one or more checkpoint proteins, has been increasing considered as targets for cancer immunotherapies. Numerous checkpoint proteins are known, such as PD-1 (Programmed Death 1, CD279) with its ligands PD-L1 (also named CD274 or B7-H1) and PD-L2; TIM-3 (T-cell Immunoglobulin domain and Mucin domain 3, also known as HAVCR2) and its ligand Gal-9; CTLA-4 (Cytotoxic T-Lymphocyte-Associated protein 4, CD152) and its ligands CD80 and CD86; and A2AR (Adenosine A2A receptor); B7-H3 (CD276); B7-H4 (VTCN1); BTLA (B and T Lymphocyte Attenuator, CD272) and its ligand HVEM (Herpesvirus Entry Mediator); IDO (Indoleamine 2,3-dioxygenase); LAG3 (Lymphocyte Activation Gene-3); VISTA (V-domain Ig suppressor of T-cell activation); MR (Killer-cell Immunoglobulin-like Receptor). These proteins are responsible for co-stimulatory or inhibitory interactions of T-cell responses. Immune checkpoint proteins regulate and maintain self-tolerance and the duration and amplitude of physiological immune responses. Immune checkpoint inhibitors include antibodies or are derived from antibodies.

The immune system has multiple inhibitory pathways that are critical for maintaining self-tolerance and modulating immune responses. In T-cells, the amplitude and quality of response is initiated through antigen recognition by the T-cell receptor and is regulated by immune checkpoint proteins that balance co-stimulatory and inhibitory signals.

PD-1 is an immune checkpoint protein, that limits the activity of T cells in peripheral tissues at the time of an inflammatory response to infection and to limit autoimmunity PD-1 blockade in vitro enhances T-cell proliferation and cytokine production in response to a challenge by specific antigen targets or by allogeneic cells in mixed lymphocyte reactions. A strong correlation between PD-1 expression and response was shown with blockade of PD-1 (Pardon, *Nature Reviews Cancer*, 12: 252-264, 2012). PD-1 blockade can be accomplished by a variety of mechanisms including antibodies that bind PD-1 or its ligands. Examples of PD-1 and PD-L1 blockers, also named PD-1 and PD-L1 inhibitors, are described in U.S. Pat. Nos. 7,488,802; 7,943,743; 8,008, 449; 8,168,757; 8,217,149, and WO03042402, WO2008156712, WO2010089411, WO2010036959, WO2011066342, WO2011159877, WO2011082400, WO2011161699, and WO2015035606. In some embodiments the PD-1 inhibitors include an antibody or a fragment antigen binding thereof, which specifically binds to PD-1. In certain other embodiments the PD-1 blockers include anti-PD-1 antibodies and similar binding proteins such as nivolumab (MDX 1106, BMS 936558, ONO-4538, Opdivo®) described in U.S. Pat. No. 8,008,449B2, a fully human IgG4 antibody that binds to and blocks the activation of PD-1 by its ligands PD-L1 and PD-L2; pembrolizumab (lambrolizumab, MK-3475 or SCH 900475, Keytruda®) disclosed in U.S. Pat. No. 8,168,757B2, a humanized monoclonal IgG4 antibody against PD-1; pidilizumab (CT-011), a humanized antibody that binds PD-1; AMP-224, a fusion protein of B7-DC; an antibody Fc portion; BMS-936559 (MDX-1105-01) for PD-L1 (B7-H1) blockade for PD-1 blockade.

Other immune checkpoint protein is CTLA-4, that downregulates pathways of T-cell activation (Fong et al., Cancer Res. 69(2):609-615, 2009; Weber Cancer Immunol. Immunother, 58:823-830, 2009). Blockade of CTLA-4 has been shown to augment T-cell activation and proliferation. Inhibitors of CTLA-4 include anti-CTLA-4 antibodies. Anti-CTLA-4 antibodies bind to CTLA-4 and block the interaction of CTLA-4 with its ligands CD80/CD86 expressed on antigen presenting cells and thereby blocking the negative down regulation of the immune responses elicited by the interaction of these molecules. Examples of anti-CTLA-4 antibodies are described in U.S. Pat. Nos. 5,811,097; 5,811,097; 5,855,887; 6,051,227; 6,207,157; 6,682,736; 6,984,720; and 7,605,238. One anti-CDLA-4 antibody is tremelimumab (ticilimumab, CP-675,206). In one embodiment, the anti-CTLA-4 antibody is ipilimumab (MDX-010, MDX-101, Yervoy®);) a fully human monoclonal IgG antibody that binds to CTLA-4. Ipilimumab is marketed under the name Yervoy™ and has been approved for the treatment of unresectable or metastatic melanoma. Other immune-checkpoint inhibitors include: LAG-3 inhibitors, such as IMP321, a soluble Ig fusion protein (Brignone et al., 2007, *J. Immunol.* 179: 4202-4211); B7 inhibitors, such as B7-H3 and B7-H4 inhibitors, eg., anti-B7-H3 antibody MGA271 (Loo et al., 2012, *Clin. Cancer Res. July* 15 (18) 3834); TIM3 inhibitors; A2AR inhibitors; BTLA inhibitors; IDO inhibitors, eg., INCB024360, an IDO1 inhibitor; VISTA inhibitors; or MR inhibitors, such as lirilumab (INN), an antibody binding to $KIR^2DL1/2L3$.

In some embodiments, the immune checkpoint inhibitor is an antibody or a fragment antigen binding thereof, or a chemical molecule drug. In some embodiments, the immune checkpoint inhibitor is a chemical molecule drug, which is an inhibitor of PD-1, PD-L1, PD-L2, TIM-3, Gal-9, CTLA-4, CD80, CD86, A2AR, B7-H3, B7-H4, BTLA, BTLA, HVEM, IDO1, IDO2, TDO, LAG3, VISTA, MR, 2B4, CD2, CD27, CD28, CD30, CD40, CD90, CD137, CD226, CD276, $DR^3$, GITR, ICOS, $LAIR^1$, LIGHT, MARCO, PS, OX-40, SLAM TIGHT, CTCNI, or a combination thereof; or an antibody or a fragment antigen binding thereof, which specifically binds to one or more checkpoint proteins selected from PD-1, PD-L1, PD-L2, TIM-3, Gal-9, CTLA-4, CD80, CD86, A2AR, B7-H3, B7-H4, BTLA, BTLA, HVEM, IDO1, IDO2, TDO, LAG3, VISTA, MR, 2B4, CD2, CD27, CD28, CD30, CD40, CD90, CD137, CD226, CD276, $DR^3$, GITR, ICOS, $LAIR^1$, LIGHT, MARCO, PS, OX-40, SLAM TIGHT, or CTCNI. In some embodiments, the immune checkpoint inhibitor is an anti-PD-1 antibody. In some embodiments, the immune checkpoint is a monoclonal antibody. In some embodiments, the immune checkpoint inhibitor is nivolumab or pidilizumab.

In some embodiments, the immune checkpoint inhibitor is a monoclonal antibody or a fragment thereof, disclosed in WO 2015/035606 A1.

Preferably, the anti-PD-1 monoclonal antibody is an antibody which comprises a heavy chain variable region (Vh) and a light chain variable region (Vl) that contain complement determinant regions (CDRs) listed as follows:

| | |
|---|---|
| a) mu317 | CDR-H1, CDR-H2 and CDR-H3 (SEQ ID NOs: 11, 12, 13, respectively); and CDR-L1, CDR-L2 and CDR-L3 (SEQ ID NOs: 14, 15, 16, respectively); |
| b) mu326 | CDR-H1, CDR-H2 and CDR-H3 (SEQ ID NOs: 17, 18, 19, respectively); and CDR-L1, CDR-L2 and CDR-L3 (SEQ ID NOs: 20, 21, 22, respectively); |
| c) 317-4B6 | CDR-H1, CDR-H2 and CDR-H3 (SEQ ID NOs: 31, 32, 33, respectively); and CDR-L1, CDR-L2 and CDR-L3 (SEQ ID NOs: 34, 35, 36, respectively); |
| d) 326-4A3 | CDR-H1, CDR-H2 and CDR-H3 (SEQ ID NOs: 37, 38, 39, respectively); and CDR-L1, CDR--L2 and CDR-L3 (SEQ ID NOs: 40, 41, 42, respectively); |
| e) 317-1H | CDR-H1, CDR-H2 and CDR-H3 (SEQ ID NOs: 11, 59, 13, respectively); and CDR-L1, CDR-L2 and CDR-L3 (SEQ ID NOs: 14, 15, 16, respectively); |
| f) 317-4B2 | CDR-HL CDR-H2 and CDR-H3 (SEQ ID NOs: 11, 60, 13, respectively); and CDR-L1, CDR-L2 and CDR-L3 (SEQ ID NOs: 61, 15, 16, respectively); |
| g) 317-4B5 | CDR-Hl, CDR-H2 and CDR-H3 (SEQ ID NOs: 11, 60, 13, respectively); and CDR-L1, CDR-L2 and CDR-L3 (SEQ ID NOs: 61, 15, 16, respectively); |
| h) 317-4B6 | CDR-H1, CDR-H2 and CDR-H3 (SEQ ID NOs: 11, 32, 13, respectively); and CDR-L1, CDR-L2 and CDR-L3 (SEQ ID NOs: 61, 15, 16, respectively); |
| i) 326-1 | CDR-H1, CDR-H2 and CDR-H3 (SEQ ID NOs: 17, 62, 19, respectively); and CDR-L1, CDR-L2 and CDR-L3 (SEQ ID NOs: 20, 21, 22, respectively); |
| j) 326-3B1 | CDR-H1, CDR-H2 and CDR-H3 (SEQ ID NOs: 17, 62, 19, respectively); and CDR-L1, CDR-L2 and CDR-L3 (SEQ ID NOs: 20, 21, 22, respectively); |
| or k) 326-3G1 | CDR-H1, CDR-H2 and CDR-H3 (SEQ ID NOs: 17, 62, 19, respectively); and CDR-L1, CDR-1 2 and CDR-L3 (SEQ ID NOs: 20, 21, 22, respectively). |

Preferably, the anti-PD-1 monoclonal antibody is an antibody which comprises a heavy chain variable region (Vh) and a light chain variable region (Vl) that contain any combinations of CDRs listed as follows:

| | |
|---|---|
| (a) | CDR-H1 (SEQ ID NO 31), CDR-H2 (SEQ ID NO 12, 32, 59 or 60) and CDR-H3 (SEQ ID NO 33), CDR-L1 ( SEQ ID NO 14, 34 or 61), CDR-L2 (SEQ ID NO 35) and CDR-L3 (SEQ ID NO 36); or |
| (b) | CDR-H1 (SEQ ID NO 37), CDR-H2 (SEQ ID NO 18, 38 or 62) and CDR-H3 (SEQ ID NO 39), CDR-L1 (SEQ ID NO 40), CDR-L2 (SEQ ID NO 41) and CDR-L3 (SEQ ID NO 42). |

Preferably, the anti-PD-1 monoclonal antibody is an antibody which comprises a heavy chain variable region (Vh) and a light chain variable region (Vl) comprising:

| |
|---|
| a) mu317 (SEQ ID NOs: 4 and 6, respectively); |
| b) mu326 (SEQ ID NOs: 8 and 10, respectively); | c) 317-4B6 (SEQ ID NOs: 24 and 26, respectively);
d) 326-4A3 (SEQ ID NOs: 28 and 30, respectively);
e) 317-4B2 (SEQ ID NOs: 43 and 44, respectively);
f) 317-4B5 (SEQ ID NOs: 45 and 46, respectively);
g) 317-1 (SEQ ID NOs: 48 and 50, respectively);
h) 326-3B1 (SEQ ID NOs: 51 and 52, respectively);
i) 326-3GI (SEQ ID NOs: 53 and 54, respectively);
j) 326-1 (SEQ ID NOs: 56 and 58, respectively);
k) 317-3A1 (SEQ ID NOs: 64 and 26, respectively);
l) 317-3C1 (SEQ ID NOs: 65 and 26, respectively);
m) 317-3E1 (SEQ ID NOs: 66 and 26, respectively);
n) 317-3F1 (SEQ ID NOs: 67 and 26, respectively);
o) 317-3G1 (SEQ ID NOs: 68 and 26, respectively);
p) 317-3H1 (SEQ ID NOs: 69 and 26, respectively);
q) 317-311 (SEQ ID NOs: 70 and 26, respectively);
r) 317-4B 1 (SEQ ID NOs: 71 and 26, respectively);
s) 317-4B3 (SEQ ID NOs: 72 and 26, respectively);
t) 317-4B4 (SEQ ID NOs: 73 and 26, respectively);
u) 317-4A2 (SEQ ID NOs: 74 and 26, respectively);
v) 326-3 A 1 (SEQ ID NOs: 75 and 30, respectively);
w) 326-3C1 (SEQ ID NOs: 76 and 30, respectively);
x) 326-3D1 (SEQ ID NOs: 77 and 30, respectively);
y) 326-3E1 (SEQ ID NOs: 78 and 30, respectively);
z) 326-3F1 (SEQ ID NOs: 79 and 30, respectively);
aa) 326-3B N55D (SEQ ID NOs: 80 and 30, respectively);
ab) 326-4A1 (SEQ ID NOs: 28 and 81, respectively); or
ac) 326-4A2 (SEQ ID NOs: 28 and 82, respectively).

Preferably, the anti-PD-1 monoclonal antibody is an antibody which comprises a IgG4 heavy chain effector or constant domain comprising any of SEQ ID NOs: 83-88.

Preferably, the anti-PD-1 monoclonal antibody is an antibody which contains a F(ab) or F(ab)2 comprising a domain said above, including a heavy chain variable region (Vh), a light chain variable region (V1) and a IgG4 heavy chain effector or constant domain.

Preferably, the anti-PD-1 monoclonal antibody is an antibody which comprise a heavy chain variable region (Vh) and a light chain variable region (V1), and a IgG4 heavy chain effector or constant domain comprising SEQ ID NOs: 87 or 88, wherein the heavy chain variable region (Vh) and the light chain variable region (V1) comprise:

a) mu317 (SEQ ID NOs: 4 and 6, respectively);
b) mu326 (SEQ ID NOs: 8 and 10, respectively);
c) 317-4B6 (SEQ ID NOs: 24 and 26, respectively);
d) 326-4A3 (SEQ ID NOs: 28 and 30, respectively);
e) 317-4B2 (SEQ ID NOs: 43 and 44, respectively);
f) 317-4B5 (SEQ ID NOs: 45 and 46, respectively);
g) 317-1 (SEQ ID NOs: 48 and 50, respectively);
h) 326-3B1 (SEQ ID NOs: 51 and 52, respectively);
i) 326-3GI (SEQ ID NOs: 53 and 54, respectively);
j) 326-1 (SEQ ID NOs: 56 and 58, respectively);
k) 317-3A1 (SEQ ID NOs: 64 and 26, respectively);
l) 317-3C1 (SEQ ID NOs: 65 and 26, respectively);
m) 317-3E1 (SEQ ID NOs: 66 and 26, respectively);
n) 317-3F1 (SEQ ID NOs: 67 and 26, respectively);
o) 317-3G1 (SEQ ID NOs: 68 and 26, respectively);
p) 317-3H1 (SEQ ID NOs: 69 and 26, respectively);
q) 317-311 (SEQ ID NOs: 70 and 26, respectively);
r) 317-4B 1 (SEQ ID NOs: 71 and 26, respectively);
s) 317-4B3 (SEQ ID NOs: 72 and 26, respectively);
t) 317-4B4 (SEQ ID NOs: 73 and 26, respectively);
u) 317-4A2 (SEQ ID NOs: 74 and 26, respectively);
v) 326-3 A 1 (SEQ ID NOs: 75 and 30, respectively);
w) 326-3C1 (SEQ ID NOs: 76 and 30, respectively);
x) 326-3D1 (SEQ ID NOs: 77 and 30, respectively);
y) 326-3E1 (SEQ ID NOs: 78 and 30, respectively);
z) 326-3F1 (SEQ ID NOs: 79 and 30, respectively);
aa) 326-3B N55D (SEQ ID NOs: 80 and 30, respectively);
ab) 326-4A1 (SEQ ID NOs: 28 and 81, respectively); or
ac) 326-4A2 (SEQ ID NOs: 28 and 82, respectively).

Preferably, the anti-PD-1 monoclonal antibody is an antibody which comprises a heavy chain variable region (Vh) and a light chain variable region (V1) (comprising SEQ ID No 24 and SEQ ID No 26, respectively) and a IgG4 heavy chain effector or constant domain (comprising SEQ ID NO 88), hereinafter Mab 1, which specifically binds to PD-1, especially PD-1 residues including K45 and 193; or, 193, L95 and P97, and inhibits PD-1-medidated cellular signaling and activities in immune cells, antibodies binding to a set of amino acid residues required for its ligand binding.

The anti-PD1 monoclonal antibodies and antibody fragments thereof may be prepared in accordance with the disclosure of WO2015/035606 A1, the entire disclosure of which is expressly incorporated herein by reference. In a preferred embodiment, the anti-PD1 monoclonal antibodies is Mab 1, which is administered at a dosage of about 2 mg/kg Q3W to about 200 mg/kg Q3W.

Targeted Therapy Agent

In some embodiment, the Btk inhibitor is co-administered with an targeted therapy agent.

Targeted therapy is one of the major modalities of medical treatment for cancer, which blocks the growth of cancer cells by interfering with specific targeted molecules needed for carcinogenesis and tumor growth, rather than by simply interfering with all rapidly dividing cells. B-lymphocyte antigen CD20 (CD20), which is an important target for the treatment of B-cell malignancies, is an activated-glycosylated phosphoprotein expressed on the surface of all B-cells beginning at the pro-B phase (CD45R+, CD117+) and progressively increasing in concentration until maturity.

In some embodiments, the targeted therapy agent is an antibody. In some of the embodiments, the targeted therapy agent is an anti-CD20 antibody. In some of the embodiments, the targeted therapy agent is a monoclonal antibody. In some of the target therapy agent is selected from rituximab, ibritumomab, tiuxetan, tositumonmab, ofatumumab or obinutuzumab.

Btk Inhibitors

"Btk inhibitor" means a compound of Formula (I), or a stereoisomer thereof, or a pharmaceutically acceptable salt thereof.

As disclosed in each of the above five aspects, the Btk inhibitor is a compound of Formula (I),

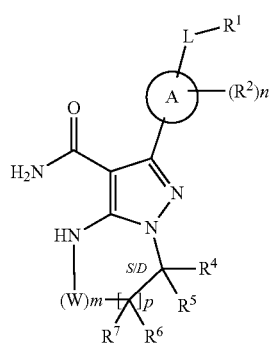

(I)

or a stereoisomer thereof, or a pharmaceutically acceptable salt thereof,
wherein:
A is a 5- or 6-membered aromatic ring comprising 0-3 heteroatoms of N, S or O;
each W is independently —(CH$_2$)— or —C(O)—;
L is a bond, CH$_2$, NR$^{12}$, O, or S;
S/D is a single or double bond, and when a double bond, R$^5$ and R$^7$ are absent;
m is 0, or an integer of 1-4;
n is 0, or an integer of 1-4, wherein when n is more than 1, each R$^2$ may be different;
p is 0, or an integer of 1-2, wherein when p is 0, m is non-zero, and when p is more than 1, each R$^6$ and each R$^7$ may be different;
R$^1$, R$^4$, R$^5$, R$^6$, and R$^7$ are each independently H, halogen, heteroalkyl, alkyl, alkenyl, cycloalkyl, aryl, saturated or unsaturated heterocyclyl, heteroaryl, alkynyl, —CN, —NR$^{13}$R$^{14}$, —OR$^{13}$, —COR$^{13}$, —CO$_2$R$^{13}$, —CONR$^{13}$R$^{14}$, —C(=NR$^{13}$)NR$^{14}$R$^{15}$, —NR$^{13}$COR$^{14}$, —NR$^{13}$CONR$^{14}$R$^{15}$, —NR$^{13}$CO$_2$R$^{14}$, —SO$_2$R$^{13}$, —NR$^{13}$SO$_2$NR$^{14}$R$^{15}$, or —NR$^{13}$SO$_2$R$^{14}$, wherein the alkyl, alkenyl, alkynyl, cycloalkyl, heteroaryl, aryl, and saturated or unsaturated heterocyclyl are optionally substituted with at least one substituent R$^{16}$, wherein (R$^4$ and R$^5$), or (R$^4$ and R$^6$), or (R$^6$ and R$^7$), or (R$^6$ and R$^6$ when p is 2), together with the atoms to which they are attached, can form a ring selected from cycloalkyl, saturated or unsaturated heterocycle, aryl, and heteroaryl rings optionally substituted with at least one substituent R$^{16}$;

R$^2$ is halogen, alkyl, —S-alkyl, —CN, —NR$^{13}$R$^{14}$, —OR$^{13}$, —COR$^{13}$, —CO$_2$R$^{13}$, —CONR$^{13}$R$^{14}$, —C(=NR$^{13}$)NR$^{14}$R$^{15}$, —NR$^{13}$COR$^{14}$, —NR$^{13}$CONR$^{14}$R$^{15}$, —NR$^{13}$CO$_2$R$^{14}$, —SO$_2$R$^{13}$, —NR$^{13}$SO$_2$NR$^{14}$R$^{15}$, or —NR$^{13}$SO$_2$R$^{14}$;

R$^{12}$ is H or lower alkyl;

R$^{13}$, R$^{14}$ and R$^{15}$ are each independently H, heteroalkyl, alkyl, alkenyl, alkynyl, cycloalkyl, saturated or unsaturated heterocyclyl, aryl, or heteroaryl; wherein (R$^{13}$ and R$^{14}$), and/or (R$^{14}$ and R$^{15}$) together with the atom(s) to which they are attached, each can form a ring selected from cycloalkyl, saturated or unsaturated heterocycle, aryl, and heteroaryl rings optionally substituted with at least one substituent R$^{16}$; R$^{16}$ is halogen, substituted or unsubstituted alkyl, substituted or unsubstituted alkenyl, substituted or unsubstituted alkynyl, substituted or unsubstituted cycloalkyl, substituted or unsubstituted aryl, substituted or unsubstituted heteroaryl, substituted or unsubstituted heterocyclyl, oxo, —CN, —OR$^a$, —NR$^a$R$^b$, —COR$^a$, —CO$_2$R$^a$, —CONR$^a$R$^b$, —C(=NR$^a$)NR$^b$R$^c$, —NR$^a$COR$^b$, —NR$^a$CONR$^a$R$^b$, —NR$^a$CO$_2$R$^b$, —SO$_2$R$^a$, —SO$_2$aryl, —NR$^a$SO$_2$NR$^b$R$^c$, or —NR$^a$SO$_2$R$^b$, wherein R$^a$, R$^b$, and R$^c$ are independently hydrogen, halogen, substituted or unsubstituted alkyl, substituted or unsubstituted alkenyl, substituted or unsubstituted alkynyl, substituted or unsubstituted cycloalkyl, substituted or unsubstituted aryl, substituted or unsubstituted heteroaryl, substituted or unsubstituted heterocyclyl, wherein (R$^a$ and R$^b$), and/or (R$^b$ and R$^c$) together with the atoms to which they are attached, can form a ring selected from cycloalkyl, saturated or unsaturated heterocycle, aryl, and heteroaryl rings.

In some embodiments, the compound of Formula (I) is optically pure.

In some embodiments, S/D is a double bond and R$^5$ and R$^7$ are absent; p is 1 and m is 0, 1 or 2; A is phenyl; and R$^4$ and R$^6$, together with the atoms to which they are attached, form a ring of formula

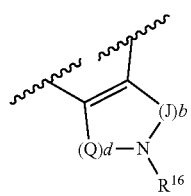

wherein Q is —CH$_2$—; J is —CH$_2$—; and d and b are each independently 0, or an integer of 1-4 S/D is a single bond; p is 1 and m is 0, 1 or 2; A is phenyl; or S/D is a single bond; p is 0 and R$^6$ and R$^7$ are absent; A is phenyl.

In some embodiments, A is phenyl; W is —(CH$_2$)—; L is 0; S/D is a single bond; m is 1; n is 0; p is 1; R$^1$ is phenyl; R$^2$ is absent; R$^5$ is H; and R$^6$ and R$^7$ are H; yielding the combination structure:

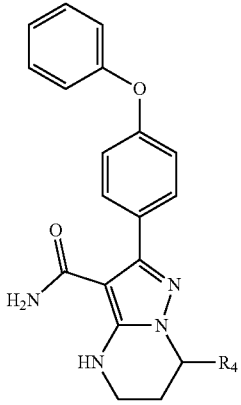

In some embodiments, R$^4$ is N-containing C$_1$-C$_8$ alkyl, N-containing C$_3$-C$_8$ cycloalkyl and phenyl, each optionally substituted.

In some embodiments, R$^4$ is methylamino, aniline group, azetidinyl, pyrrolidinyl, piperidinyl, azacycloheptenyl, each N-substituted with a moiety selected from benzyl, acyl, acryloyl, substituted-acryloyl, propiolyl, and substituted-propiolyl.

In some embodiments, R$^4$ is selected from structures,

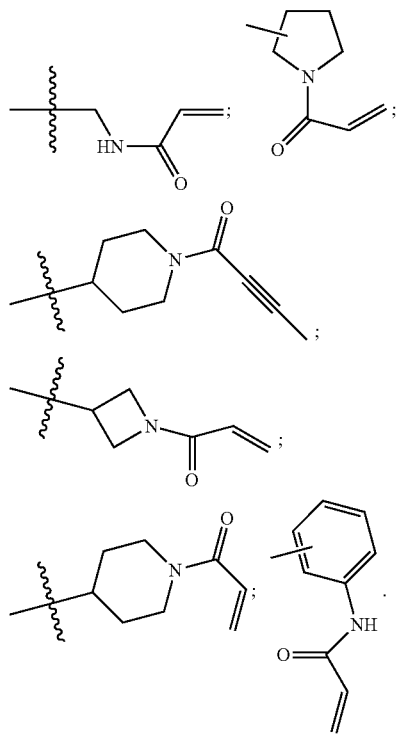

In some embodiments, R$^4$ s 1-acryloylpiperidin-4-yl (i.e., Compound 27 in WO 2014/173289 A1).

As disclosed in each of the above five aspects, the Btk inhibitor is a compound of Formula (II)—i.e., Compound 1,

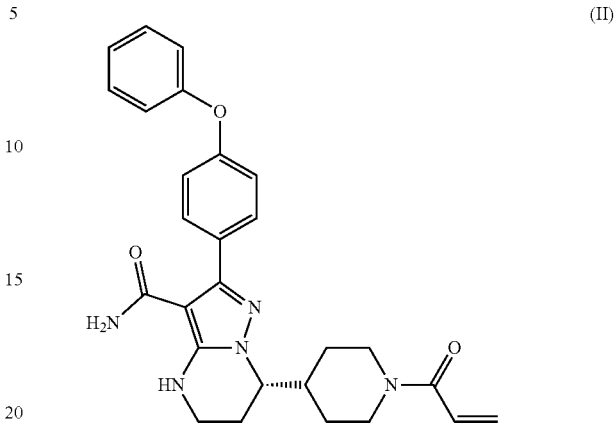

(II)

or a pharmaceutically acceptable salt thereof.

The Btk inhibitor disclosed herein, such as the compound of Formula (II), may be synthesized by synthetic routes disclosed in WO 2014/173289 A1 and unpublished PCT application PCT/CN2016/095510, the entire disclosure of which is expressly incorporated herein by reference. The Btk inhibitor, i.e., Compound 1, disclosed herein, may be prepared in accordance with the procedures in PCT/CN2016/095510, the entire disclosure of which is expressly incorporated herein by reference.

Combination Therapy

The combination therapy may be administered as a simultaneous, or separate or sequential regimen. When administered sequentially, the combination may be administered in two or more administrations. The combined administration includes co-administration, using separate formulation, and consecutive administration in either order, wherein preferably there is a time period while both (or all) active agents simultaneously exert their biological activities.

Suitable dosages for any of the above co-administered agents are those presently used and may be lowered due to the combined action (synergy) of the Btk inhibitor and the targeted therapy agent or the immune checkpoint inhibitor, such as to increase the therapeutic index or mitigate toxicity or other side-effects or consequences.

In a particular embodiment of anti-cancer therapy, the Btk inhibitor and the targeted therapy agent or the immune checkpoint inhibitor may be further combined with surgical therapy and radiotherapy.

In an embodiment of each of the above five aspects, the amounts of the Btk inhibitor and the targeted therapy agent or the immune checkpoint inhibitor disclosed herein and the relative timings of administration be determined by the individual needs of the patient to be treated, administration route, severity of disease or illness, dosing schedule, as well as evaluation and judgment of the designated doctor.

The Btk inhibitor and the targeted therapy agent or the immune checkpoint inhibitor disclosed herein may be administered in various known manners, such as orally, topically, rectally, parenterally, by inhalation spray, or via an implanted reservoir, although the most suitable route in any given case will depend on the particular host, and nature and severity of the conditions for which the active ingredient is being administered. The term "parenteral" as used herein includes subcutaneous, intracutaneous, intravenous, intramuscular, intraarticular, intraarterial, intrasynovial, intrasternal, intrathecal, intralesional and intracranial injection or infusion techniques.

In one embodiment of each of the above five aspects, the Btk inhibitor and the targeted therapy agent or the immune checkpoint inhibitor disclosed herein may be administered in different route. In a preferred embodiment, the Btk inhibitor is administered orally, and the targeted therapy agent or the immune checkpoint inhibitor is administered parenterally such as subcutaneously, intracutaneously, intravenously or intraperitoneally. In a preferred embodiment, the BTK inhibitor is administered once a day, two times per day, three times per day, four times per day, or five times per day, and is administered at a dosage of about 80 mg/day to about 640 mg/day. In a preferred embodiment, the BTK inhibitor is administered at a dose of 320 mg QD or 160 mg BID.

EXAMPLE

The present invention is further exemplified, but not limited to, by the following examples that illustrate the invention.

Example 1 Preparation of (S)-7-(1-acryloylpiperidin-4-yl)-2-(4-phenoxyphenyl)-4,5,6,7-tetrahydropyrazolo[1,5-a]pyrimidine-3-carboxamide (Compound 1) and Crystalline Form A Thereof Step 1: Synthesis of BG-2

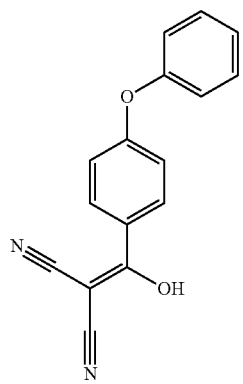

BG-2

Under nitrogen atmosphere, to a solution of EA (5 v), HOBT (1.2 eq.), EDCI (1.2 eq.), 4-phenoxybenzoic acid (BG-1, 80 Kg, 1.0 eq.) and malononitrile (1.2 eq.) was added TEA (2.4 eq.) at 10° C. The mixture was then stirred at RT until the reaction was completed. The mixture was then centrifuged and the cake was washed with EA. The filtrate was washed with aqueous $NaHCO_3$ twice and $NH_4Cl$. The organic phase was washed with 1.5 N $H_2SO_4$ twice and stirred. Concentrated, precipitated from methanol and purified water. The solid was collected by centrifugation and dried under vacuum. This gave 79.9 Kg of BG-2. $^1$H NMR (DMSO-$d_6$) δ 7.62 (d, J=8.6 Hz, 2H), 7.46-7.38 (m, 2H), 7.18 (t, J=7.4 Hz, 1H), 7.06 (d, J=8.0 Hz, 2H), 6.94 (d, J=8.6 Hz, 2H).

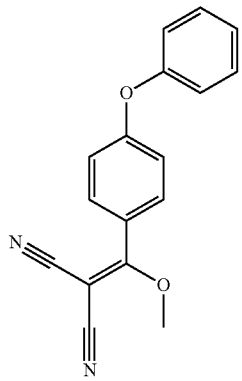

BG-3

Step 2: Synthesis of BG-3

Under nitrogen atmosphere, a solution of BG-2 (79.9 kg, 1.0 eq.) in MeCN (5.0 v) was added into trimethoxymethane (12.0 v) at 85° C. The resultant mixture was stirred until the reaction was completed. Sampled for HPLC analysis. Concentrated under vacuum. The residue was precipitated from i-PrOH and hexane. The mixture was centrifuged, and the cake was washed with hexane and dried under vacuum. This gave 71.7 Kg of product. $^1$H NMR (400 MHz, DMSO-$d_6$) δ 7.70 (d, J=8.4 Hz, 2H), 7.52-7.45 (m, 2H), 7.28 (t, J=7.6 Hz, 1H), 7.22-7.06 (m, 4H), 3.93 (s, 3H).

Step 3: Synthesis of BG-4

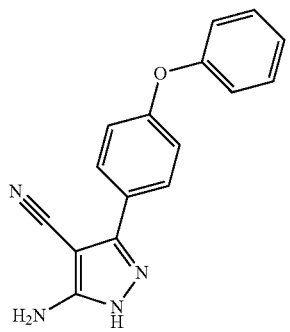

BG-4

Under nitrogen atmosphere, to a solution of BG-3 (71.6 kg, 1.0 eq.) in ethanol (2.5 v) hydrazinium hydroxide (1.0 eq) in ethanol (0.6 v) was charged dropwise to the reactor below 15° C. The solution was heated to RT and stirred until the reaction was completed. Water (4.0 v) was added to the reactor. The solution was then cooled to 5° C., centrifuged and the cake was washed with water (1.0 v). The cake was dried under vacuum. This gave 66.9 Kg of product. $^1$H NMR (DMSO-$d_6$) δ 12.11 (br s, 1H), 7.80 (d, J=8.8 Hz, 2H), 7.46-7.39 (m, 2H), 7.18 (t, J=7.6 Hz, 1H), 7.12-7.04 (m, 4H), 6.43 (br s, 2H).

Steps 4 to 6: Synthesis of BG-8

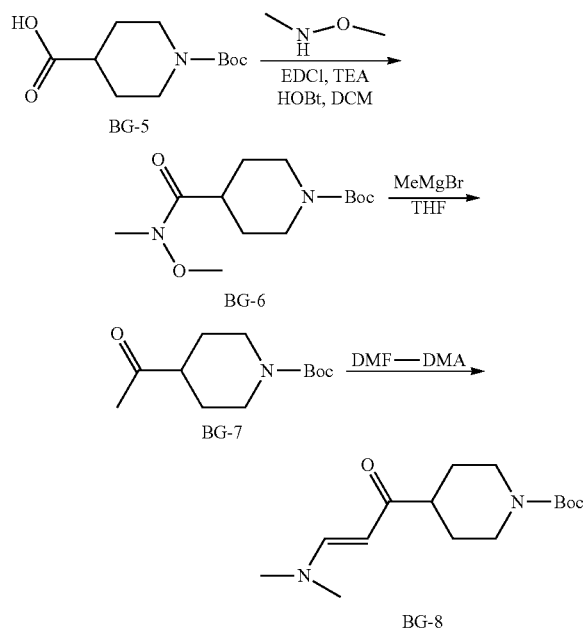

Step 7: Synthesis of BG-9

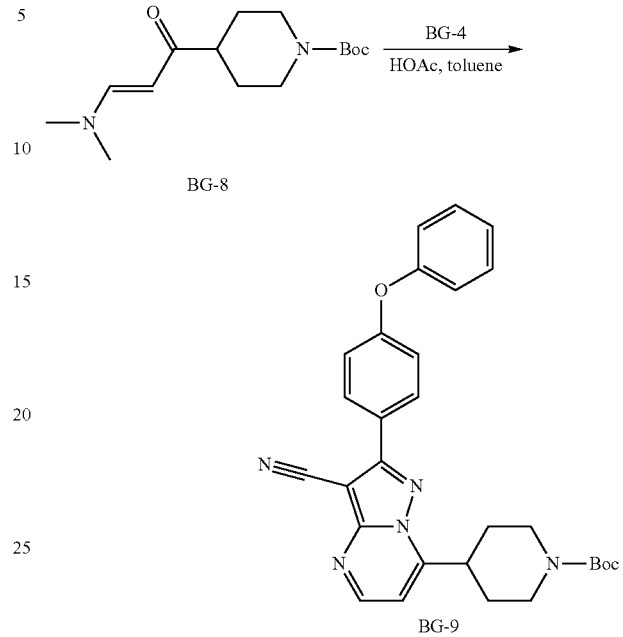

To a mixture of DCM (8.0 v), BG-5 (80.0 Kg, 1.0 eq.), N,O-dimethylhydroxylamine hydrochloride (1.2 eq.), HOBt (1.2 eq.) and EDCI (1.2 eq.), TEA (2.6 eq.) was charged dropwise below 15° C. the mixture was stirred at RT until the reaction was completed, centrifuged and the cake was washed with DCM (1.0 v) twice. The filtrate was washed with 20% aqueous NH$_4$Cl (3×4.0 v). The filtrate was concentrated under vacuum to give the crude product BG-6, which was used in the next step without further purification. The residue was dissolved in toluene (5.0 v) and THF (1.0 v), cooled to 10° C., charged dropwise MeMgBr (1.4 eq.) at 10° C. and then stirred at RT until the reaction was completed. The solution was cooled below 10° C. Saturated aqueous NH$_4$Cl was charged dropwise below 10° C. The mixture was centrifuged, separated, filtrated, and the organic phase was washed with aqueous NaCl twice. The organic phase was concentrated to give the crude product, which was used in the next step without further purification. The residue in DMF (2.5 v) and DMF-DMA (2.5 v) was stirred at 110° C. until the reaction was completed. The reaction mixture was cooled, concentrated and then DCM was added. The final mixture was washed with saturated aqueous NH$_4$Cl. The organic layer was concentrated and precipitated by charging hexane. The mixture was centrifuged and the cake was collected. The cake was dried under vacuum. This gave 82.2 Kg of the desired product. $^1$H NMR (DMSO-d$_6$) δ 7.49 (d, J=12.6 Hz, 1H), 5.01 (d, J=12.6 Hz, 1H), 3.99-3.82 (m, 2H), 3.14-2.94 (m, 2H), 2.89-2.61 (m, 6H), 2.49-2.37 (m, 1H), 1.66-1.56 (m, 2H), 1.39 (s, 9H), 1.39-1.20 (m, 2H).

Under nitrogen atmosphere, a mixture of toluene (8.0 v), AcOH (0.5 v), BG-8 (1.2 eq.) and BG-4 (66.9 Kg 1.0 eq.) was heated to 95° C. and stirred until the reaction was completed. The mixture was cooled, concentrated and precipitated from methanol. The mixture was centrifuged and the cake was washed with methanol. The cake was dried under vacuum. This gave 107.8 Kg of product. $^1$H NMR (DMSO-d$_6$) δ 8.78 (d, J=4.6 Hz, 1H), 8.15-8.07 (m, 2H), 7.51-7.41 (m, 2H), 7.34 (d, J=4.6 Hz, 1H), 7.27-7.19 (m, 3H), 7.17-7.10 (m, 2H), 4.24-4.02 (m, 2H), 3.81-3.69 (m, 1H), 3.12-3.82 (m, 2H), 2.15-2.04 (m, 2H), 1.76-1.60 (m, 2H), 1.43 (s, 9H).

Step 8: Synthesis of BG-10

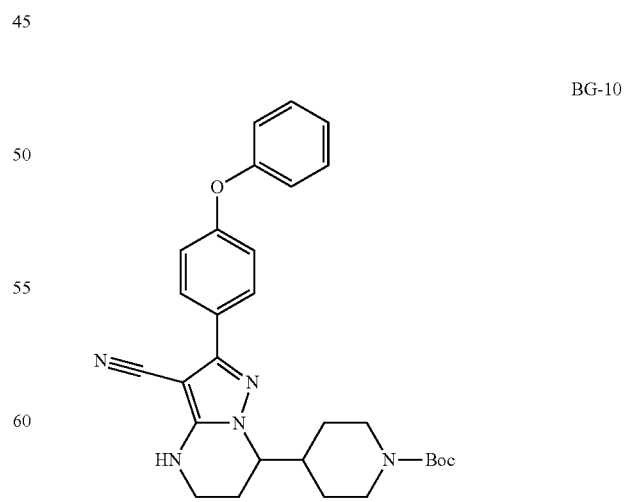

To a mixture of THF (10.0 v), BG-9 (13.0 Kg, 1.0 eq.) and D-DBTA (1.0 eq) under N$_2$ was charged Pd/C (10% w/w), hydrogen gas was introduced into the reactor and the hydrogen pressure was maintained to 1.8 MPa. The reactor was heated to 40° C. slowly and stirred until the reaction was completed. The mixture was then cooled, filtered, and the cake was washed with THF. The filtrate was collected, and concentrated under vacuum. DCM was added. The residue was washed with aq. NaHCO₃, concentrated and precipitated from MTBE and hexane, then centrifuged. The cake was collected and dried under vacuum to give the desired compound (yield:94.8% and purity:98.5%). ¹H-NMR (DMSO-d₆) δ 7.82-7.76 (m, 2H), 7.56-7.51 (m, 1H), 7.45-7.37 (m, 2H), 7.21-7.14 (m, 1H), 7.12-7.03 (m, 4H), 4.09-3.91 (m, 3H), 3.30-3.22 (m, 2H), 2.82-2.55 (m, 2H), 2.18-1.99 (m, 2H), 1.98-1.86 (m, 1H), 1.69-1.58 (m, 1H), 1.56-1.45 (m, 1H), 1.38 (s, 9H), 1.32-1.13 (m, 2H).

Step 9: Synthesis of BG-11

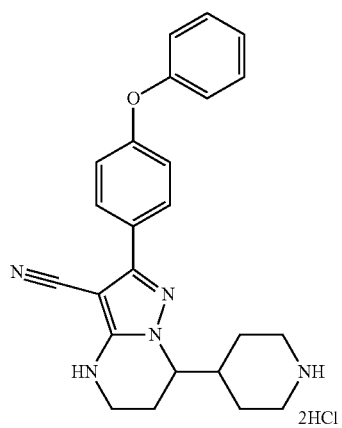

BG-11

To a solution of BG-10 (100.0 Kg 1.0 eq.) in DCM (6.0 v) was added dropwise HCl in EtOH (20.9% w/w, 2.0 v) under nitrogen atmosphere. The mixture is stirred until the reaction was completed. MTBE (4.0 v) was added to the solution, cooled. The cakes was collected by centrifugation and washed with hexane (2.0 V), then the cake was slurried in hexane (5 v), and centrifuged again. The cake was washed with hexane (2.0 V) and dried under vacuum. This gave 85.2 Kg product. ¹H-NMR (DMSO-d₆) δ 9.25-8.85 (m, 2H), 7.84-7.70 (m, 2H), 7.47-7.37 (m, 2H), 7.18 (t, J=7.4 Hz, 1H), 7.12-7.03 (m, 4H), 5.73 (br s, 2H), 4.12-4.03 (m, 1H), 3.25-3.19 (m, 4H), 2.90-2.73 (m, 2H), 2.28-2.12 (m, 1H), 2.10-2.00 (m, 1H), 1.99-1.86 (m, 1H), 1.84-1.52 (m, 4H).

Step 10: Synthesis of BG-11A

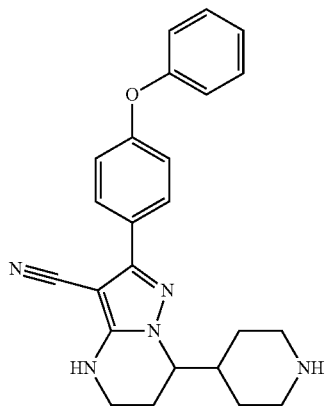

BG-11A

A mixture of BG-11 (85.0 Kg, 1.0 eq) in water (6.0 v) and NaOH (3.0 eq) was stirred until the reaction was completed at RT. The cake was collected and slurried in MTBE (6.0 v). The mixture was then centrifuged to collect the cake. The cake was dried under vacuum. This gave 71.3 Kg product. ¹H-NMR (DMSO-d₆) δ 7.82-7.74 (m, 2H), 7.54-7.49 (m, 1H), 7.45-7.38 (m, 2H), 7.21-7.14 (m, 1H), 7.12-7.04 (m, 4H), 4.03-3.95 (m, 1H), 3.29-3.21 (m, 2H), 3.00-2.87 (m, 2H), 2.46-2.31 (m, 2H), 2.11-1.83 (m, 3H), 1.58-1.12 (m, 4H).

Step 11: Synthesis of BG-11B

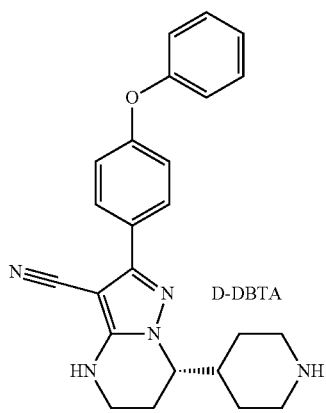

BG-11B

A mixture of enthanol/water/acetic acid (7:3:1, 46 v) and BG-11A (30 kg, 1.0 eq.) in a reactor was heated to 70±5° C. under nitrogen atmosphere, then a solution of D-DBTA (1.20 eq.) in ethanol/water/acetic acid (7:3:1, 4 v) was added dropwise with the temperature not less than 65° C. The resulting solution was stirred for 16 hrs at 60-65° C., then cooled to RT. The solid was collected by centrifugation and washed with ethanol (2.0 v). The cake was slurried in the mixed solvent of ethanol/water/AcOH (7:3:1, 20 v) for 16 hrs at 55° C. and cooled to RT. The solid was collected by centrifugation, washed with ethanol (2.0 v). The cake was dried under vacuum (Yield: 37.9%). ¹H-NMR (DMSO-d₆) δ 8.76 (br s, 2H), 7.99-7.89 (m, 4H), 7.83-7.75 (m, 2H), 7.66-7.57 (m, 3H), 7.52-7.45 (m, 4H), 7.45-7.39 (m, 2H), 7.21-7.14 (m, 1H), 7.13-7.03 (m, 4H), 5.64 (s, 2H), 4.08-4.00 (m, 1H), 3.29-3.19 (m, 4H), 2.85-2.72 (m, 2H), 2.21-1.40 (m, 7H).

Step 12: Synthesis of BG-11C

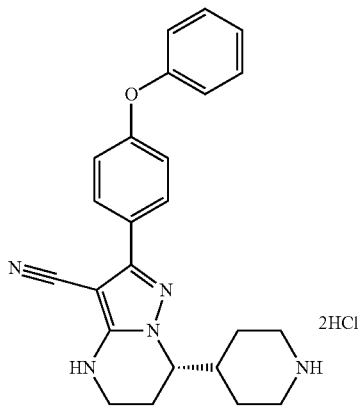

BG-11C

To a mixture of dichloromethane (15.0 v) and 20.0% aqueous KOH (3.0 v) was added bachwise BG-11B (48.0 kg, 1.0 eq.) under nitrogen atmosphere at RT. After the reaction was completed, the organic layer was collected and the water layer was extracted with dichloromethane (5.0 v). The organic layers were combined. Con. HCl (0.36 v) was added to the above organic layers at RT. The resulting mixture was stirred until the reaction was completed. The solid was collected by centrifugation and washed with dichloromethane (1.0 v). The collected solid was slurried with MTBE (6.0 v). The solid was collected by centrifugation and washed with MTBE (1.0 v), then was dried under vacuum. This gave 31.5 Kg product (Yield:100%).

Step 12: Synthesis of BG-11D (Alternative Intermediate)

ACN (5.0 v), soft water (10.0 v), KOH (5.0 eq) was charged to a reactor and stirred for at least 15 min. BG-11B (1.0 eq) was charge to the reactor in portion-wise. The mixture was stirred until the reaction was completed. The cake was collected by centrifugation, slurried in ACN (1.0 v) and soft water (5.0 v), and dried under vacuum to give the product.

Step 13: Synthesis of BG-12

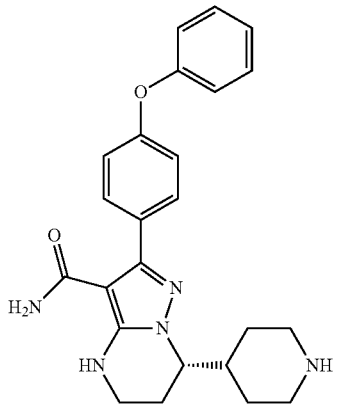

BG-12

A solution of BG-11C (15.0 Kg 1.0 eq.) in MsOH (2.5 v) was stirred at 85° C. under nitrogen atmosphere until the reaction was completed. After cooling to 5° C. purified water (4.0 v) was added dropwise to the system and kept the temperature not more than 35° C. (temperature increased obviously). The resulting solution was stirred for 16 hrs at 30° C., and then washed with DCM (2×3.0 v). The aqueous phase was collected. DCM (6.0 v) was added to the aqueous phase, the mixture was cooled to 5° C. The pH value was adjusted to 11~12 with 20% aqueous NaOH (temperature increased obviously) with stirring with the temperature not more than 30° C. The organic phase was separated and collected. The aqueous was extracted with DCM (3.0 v). The organic layers were combined and concentrated. MTBE (4.0 v) was added to the residue. The mixture was then concentrated and precipitated from n-heptane. The solid was collected by centrifugation and dried in a vacuum oven. This gave 12.55 Kg product (Yield: 94.9%). ¹H-NMR (DMSO-d₆) δ 7.52-7.46 (m, 2H), 7.45-7.38 (m, 2H), 7.21-7.13 (m, 1H), 7.12-7.03 (m, 4H), 6.64 (s, 1H), 3.99-3.90 (m, 1H), 3.29-3.22 (m, 2H), 3.03-2.90 (m, 2H), 2.48-2.36 (m, 2H), 2.03 (dd, J=13.9, 5.6 Hz, 2H), 2.14-1.99 (m, 1H), 1.97-1.85 (m, 1H), 1.65-1.15 (m, 3H).

Step 14: Synthesis of BG-13

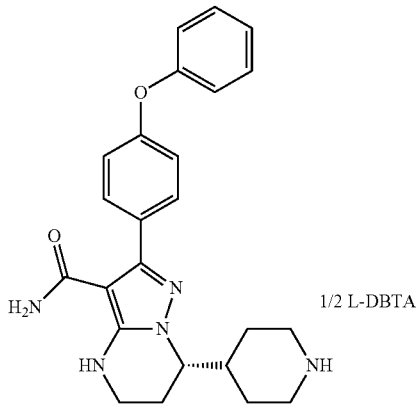

BG-13

A mixture of MeOH (13.5 v), purified water (4.5 v) and BG-12 (8.5 Kg, 1.0 eq.) in a reactor was heated to 50° C. under N₂ atmosphere. To the mixture was charged dropwise a solution of L-DBTA (0.7 eq) in MeOH/purified water (1.5 v/0.5 v) while keeping the temperature at 50° C. After addition, the mixture was stirred for at least 2 hrs at 50° C., and then cooled to RT and stirred for at least 16 hrs at RT. The cake was collected by Centrifugation and was washed with MeOH (2.0 v). The cake was dried in a vacuum oven. This gave 9.08 Kg product (Yield: 74.8%).

Step 15: Synthesis of (S)-7-(1-acryloylpiperidin-4-yl)-2-(4-phenoxyphenyl)-4,5,6,7-tetrahydropyrazolo[1,5-a]pyrimidine-3-carboxamide (Compound 1)

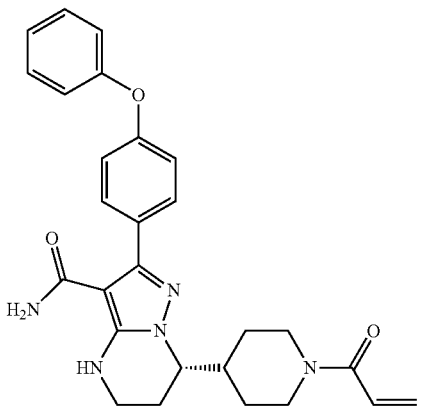 [SMILES: C=CC(=O)N1CCC([C@@H]2CCNc3c(C(N)=O)c(-c4ccc(Oc5ccccc5)cc4)nn32)CC1]

Under N₂ atmosphere, ACN (12.0 v), water (12.5 v), BG-13 (8.0 Kg, 1.0 eq), and NaHCO₃ (2.5 eq.) were added to a reactor. The mixture was then cooled to −5-0° C. To the mixture, the solution of acryloyl chloride (1.1 eq.) in MeCN (0.5 v) was added dropwise and stirred until the reaction was completed. EA (6.0 v) was then added to the reactor, and stirred. The organic phase was collected. The aqueous layer was further extracted with EA (3.0 v). The organic phases were combined and washed with brine. The organic layer was collected and concentrated.

The residue was purified by silica gel (2 wt) column, eluted with 3% w/w methanol in DCM (21.0 v). The Compound 1 solution was collected and concentrated under vacuum. The residue was precipitated from EA/MTBE (2.0 v). The cake was collected by centrifugation as the product.

Step 15: Synthesis of (S)-7-(1-acryloylpiperidin-4-yl)-2-(4-phenoxyphenyl)-4,5,6,7-tetrahydropyrazolo[1,5-a]pyrimidine-3-carboxamide (Compound 1, Alternative Method)

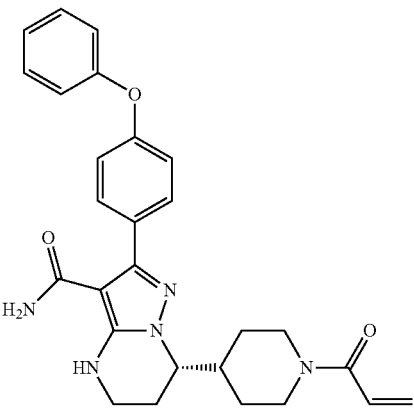 [SMILES: C=CC(=O)N1CCC([C@@H]2CCNc3c(C(N)=O)c(-c4ccc(Oc5ccccc5)cc4)nn32)CC1]

A mixture of CH₃CN (10.0 v), purified water (5.0 v), NaOH (1.5 eq.) and BG-13 (1.0 eq.) was stirred to get a clear solution. EtOAc (6.0 v) was then charged to the reaction and separated. The organic phase was collected and washed with 15% brine (3.0 v) twice. The organic phase prepared above was concentrated and the solvent was swapped to CH₃CN (residue volume: NMT 5.0 v). CH₃CN (7.5 v) and purified water (12.5 v) were charged and cooled to 15-20° C. L-(+)-tartaric acid (0.5 eq) and NaHCO₃ (2.5 eq.) were charged to the reaction mixture. A solution of acryloyl chloride (1.1 eq.) in CH₃CN (0.5 v) was charged drop-wise to the reaction mixture. After the reaction was completed, EtOAc (6.0 v) was charged to the reaction mixture and organic layer was collected. Aqueous phase was further extracted with EA (3.0 v). The organic layers were combined, washed with 15% brine (5.0 v) and concentrated. The solvent was swapped to DCM (volume of residue: 1.5-2.0 v) and purified by silica gel column (silica gel: 100-200 mush, 2.0 w/w; eluent: 3% w/w MeOH in DCM (about 50 v). The collected solution was concentrated and swapped to EtOAc (4.0 v). MTBE (6.4 v) was charged drop-wise to residue at 50° C. The mixture was then cooled to 5° C. and the cake was collected centrifugation.

Step 16: Preparation of Crystalline Form A of Compound 1

The above cake was dissolved in 7.0 volumes of DCM, and then swapped to solvent EA. After recrystallization from EA/MTBE, the cakes was collected by centrifugation, and was dried under vacuum. This gave 4.44 Kg product (Yield: 70.2%).

Figure 8:
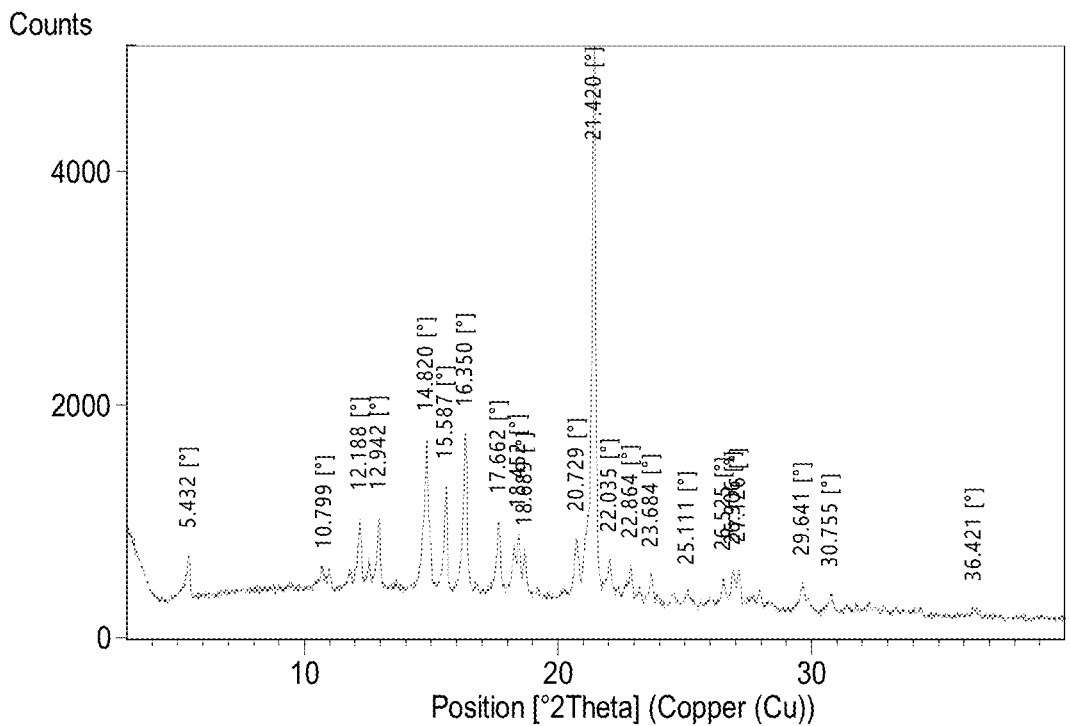
FIG. 8 shows an X-ray diffraction pattern of Compound 1 in a crystalline form.

The product was then characterized by X-ray powder diffraction (XRPD) pattern method, which was generated on a PANalytical Empyrean X-ray powder diffractometer with the XRPD parameters as follows: X-Ray wavelength (Cu, kα, Kα1 (Å): 1.540598, Kα2 (Å): 1.544426; Kα2/Kα1 intensity ratio: 0.50); X-Ray tube setting (45 Kv, 40 mA); divergence slit (automatic); scan mode (Continuous); scan range (° 2TH) (3°-40); step size (° 2TH) (0.0131); scan speed (°/min) (about 10). The XRPD result found the resultant product as a crystalline shown in FIG. 8.

Figure 9:
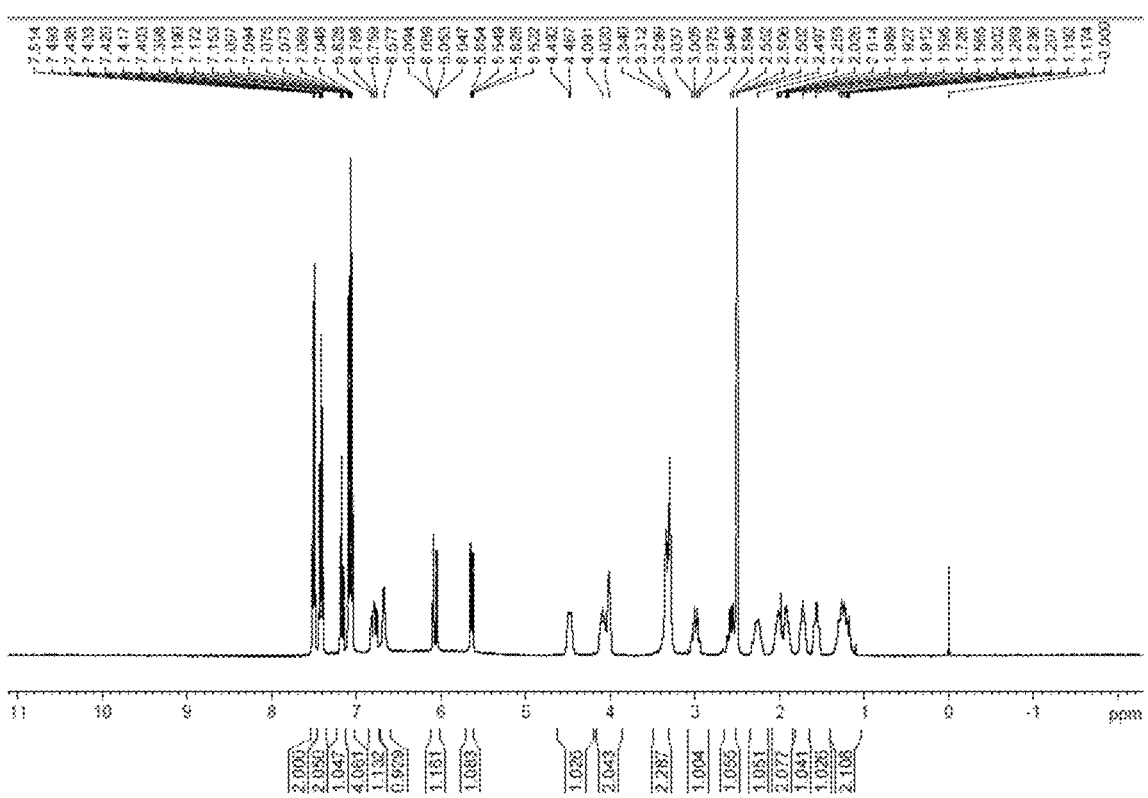
FIG. 9 shows $^1$H-NMR of the crystalline form of Compound 1.

The proton nuclear magnetic resonance ($^1$H-NMR) shown as in FIG. 9 was collected on a Bruker 400M NMR Spectrometer in DMSO-$d_6$. $^1$H-NMR (DMSO-$d_6$) δ 7.50 (d, J=8.6 Hz, 2H), 7.46-7.38 (m, 2H), 7.17 (t, J=7.6 Hz, 1H), 7.08 (d, J=7.6 Hz, 2H), 7.05 (d, J=8.8 Hz, 2H), 6.85-6.72 (m, 1H), 6.67 (s, 1H), 6.07 (dd, J=16.8, 2.2 Hz, 1H), 5.64 (dd, J=10.4 Hz, 2.2 Hz, 1H), 4.55-4.38 (m, 1H), 4.17-3.94 (m, 2H), 3.33-3.22 (m, 2H), 3.08-2.88 (m, 1H), 2.67-2.51 (m, 1H), 2.36-2.15 (m, 1H), 2.12-1.82 (m, 2H), 1.79-1.65 (m, 1H), 1.63-1.49 (m, 1H), 1.38-1.08 (m, 2H).

Figure 10:
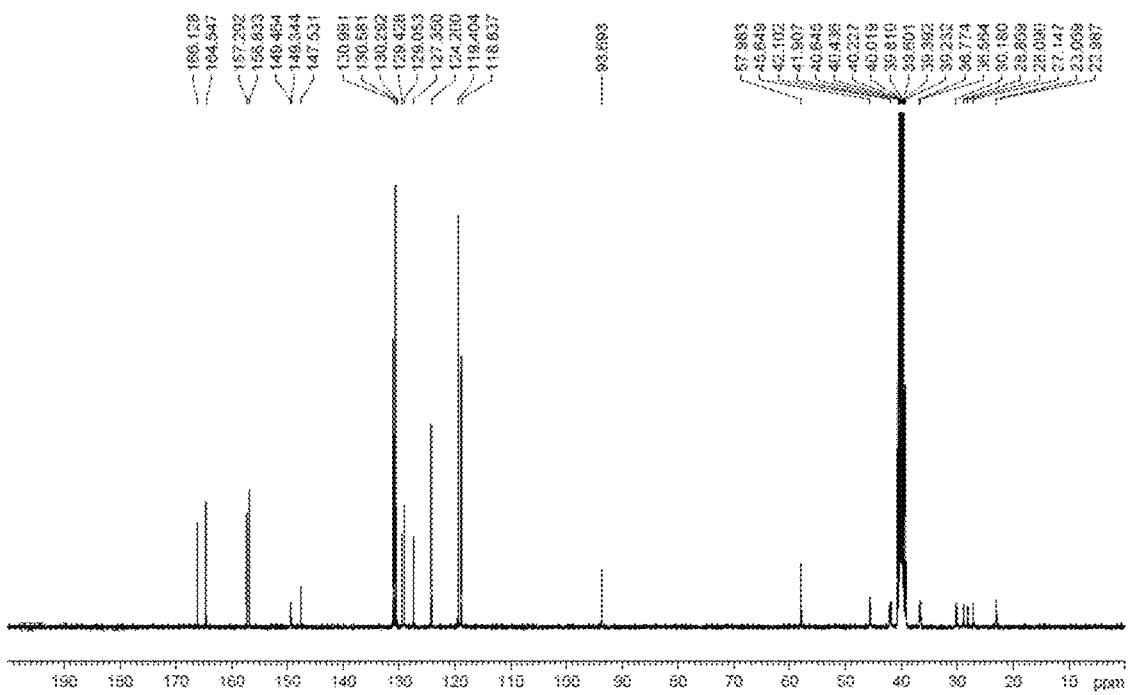
FIG. 10 shows $^{13}$C-NMR of the crystalline form of Compound 1.

The carbon nuclear magnetic resonance ($^{13}$C-NMR) shown as in FIG. 10 was collected on a Bruker 400M NMR Spectrometer in DMSO-$d_6$. $^{13}$C-NMR spectra for Crystalline Form A of Compound 1.

Example 2 Effect of the Combination of Anti-CD20 mAb and BTK Inhibitor in Human REC-1/NK92MI Mantle Cell Lymphoma Xenograft Model Method REC-1 cells were cultured in RPMI1640 complete medium supplemented with 10% (v/v) fetal bovine serum, and 100 μg/mL of penicillin and streptomycin. NK92MI/CD16V cell line, overexpressing CD16 and FcRγ chain, was established from parental cell line NK92MI. The cells were maintained in MEM alpha supplemented with 0.2 mM inositol; 0.1 mM 2-mercaptoethanol; 0.02 mM folic acid; 1×NEAA; adjust to a final concentration of 20% (v/v) fetal bovine serum and 100 μg/mL of penicillin and streptomycin. NOD/SCID mice were pre-treated with cyclophosphamide (prepared in saline, 150 mg/kg, i.p.) and disulfiram (prepared in 0.8% Tween-80 in saline, 125 mg/kg, p.o., one hour after each dose of cyclophosphamide) once daily for two days.

On the day of implantation, culture medium was replaced with fresh medium. Four hours later, media was removed and cells were collected as described above. Cells were re-suspended in cold (4° C.) PBS and same volume of matrigel was added to give a final concentration of $5×10^7$ cells/mL for REC-1 and $1×10^7$ cells/mL for NK92MI/CD16V, respectively. Re-suspended cells were placed on ice prior to inoculation. The right flank region of each mouse was cleaned with 75% ethanol prior to cell inoculation. Animals were then co-injected subcutaneously with $1×10^7$ REC-1 cells and $2×10^6$ NK92MI/CD16V cells in 200 μl of cell suspension in the right front flank via a 26-gauge needle.

On day 3 after inoculation, animals were randomly divided into four groups with 12 mice per group. The groups consisted of a control group (no drug treatment), 2.5 mg/kg of Compound 1, 2 mg/kg of obinutuzumab (Gazyva®, obtained from Roch), and the combination of Compound 1 and obinutuzumab (2.5 mg/kg and 2 mg/kg, respectively). Treatments were administered in a volume of 10 mL/kg body weight, assessed immediately before dosing and the volume dosed was adjusted accordingly. Compound 1 was administered by oral gavage (p.o.) twice daily (BID) and obinutuzumab was administered by intraperitoneal (i.p.) injection once weekly (QW). After implantation, primary tumor volume was measured in two dimensions using a calliper.

Individual body weight was recorded twice weekly, with mice being monitored daily for clinical signs of toxicity for the duration of the study. Mice were euthanized using carbon dioxide when their tumor volume reached 2,500 mm$^3$ after twice measurements, the tumor was ulcerated, or body weight loss exceeded 20%.

Tumor volume was calculated using the formula: V=0.5× (a×b$^2$) where a and b are the long and short diameters of the tumor, respectively. Tumor growth inhibition (TGI) was calculated using the following formula:

% TGI=100×[1−(treated$_t$/placebo$_t$)]

treated$_t$=treated tumor volume at time t
placebo$_t$=placebo tumor volume at time t Result In vivo efficacy of Compound 1 and obinutuzumab was examined in human REC-1/NK92MI MCL xenograft model. Compound 1, as a single agent, was shown to be active in this model, with 72% TGI on day 23, while obinutuzumab, as a single agent, was shown to have no anti-tumor effect. The combination of these two agents induced 98% TGI on day 23 which was significantly more efficacious than either single agent (FIG. 1).

Example 3 Effect of the Combination of Anti-CD20 mAb and BTK Inhibitor in Human TMD-8 DLBCL Xenograft Model Method TMD-8 DLBCL cells were cultured in RPMI1640 complete medium supplemented with 10% (v/v) fetal bovine serum, and 100 μg/mL of penicillin and streptomycin. On the day of implantation, culture medium was replaced with fresh medium. Four hours later, media was removed and cells were collected as described above. Cells were re-suspended in cold (4° C.) PBS and same volume of matrigel was added to give a final concentration of $5×10^7$ cells/mL for TMD-8 cells. Re-suspended cells were placed on ice prior to inoculation. The right flank region of each mouse was cleaned with 75% ethanol prior to cell inoculation. Animals were then injected subcutaneously with $1×10^7$ TMD-8 cells in 200 μl of cell suspension in the right front flank via a 26-gauge needle.

On day 7 after inoculation, animals were randomly divided into 4 groups with 10 mice per group. The groups consisted of a control group (no drug treatment), 7.5 mg/kg of Compound 1, 10 mg/kg of obinutuzumab (Gazyva®, obtained from Roch), and the combination of Compound 1 and obinutuzumab. Treatments were administered in a volume of 10 mL/kg body weight, assessed immediately before dosing and the volume dosed was adjusted accordingly. Compound 1 was administered by oral gavage (p.o.) twice daily (BID) and obinutuzumab was administered by intraperitoneal (i.p.) injection once every week (QW). After implantation, primary tumor volume was measured in two dimensions using a calliper.

Mice were euthanized using carbon dioxide when their tumor volume reached 2,500 mm$^3$ after twice measurements, the tumor was ulcerated, or body weight loss exceeded 20%.

Figure 2:
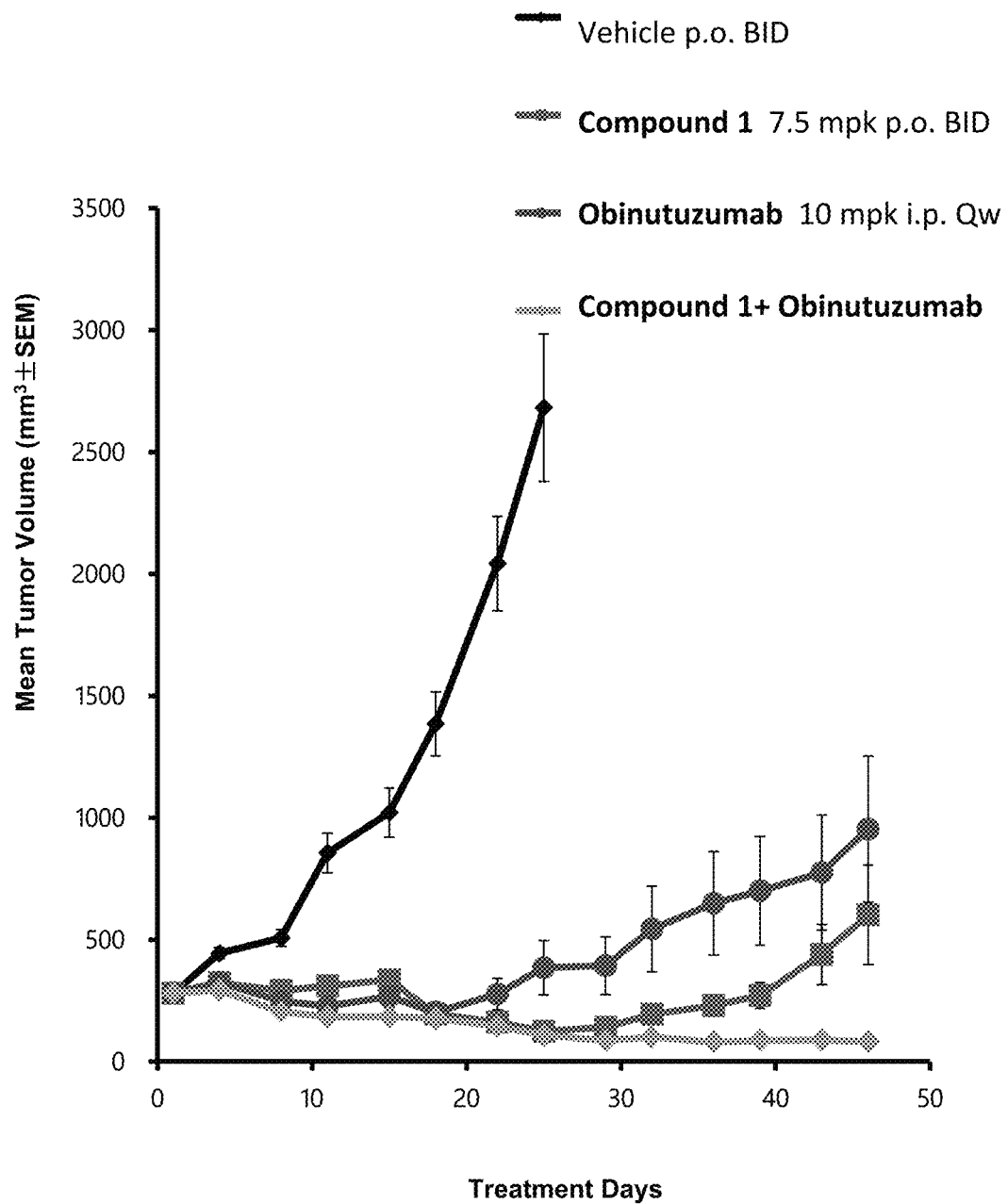
FIG. 2 shows the combination effect of Compound 1 and anti-CD20 mAb (obinutuzumab) on tumor growth in human TMD-8 DLBCL xenograft model.

Tumor volume was calculated using the formula: V=0.5× (a×b$^2$) where a and b are the long and short diameters of the tumor, respectively. Tumor growth inhibition (TGI) was calculated using the following formula:

% TGI=100×[1−(treated$_t$/placebo$_t$)]

treated$_t$=treated tumor volume at time t
placebo$_t$=placebo tumor volume at time t Result On day 46, treatments of Compound 1 and obinutuzumab resulted in 81% and 61% of tumor growth inhibition (TGI), respectively. Objective responses were observed with Compound 1 at 7.5 mg/kg (1CR/4PR/5) and obinutuzumab at 10 mg/kg (0CR/2PR/2). The combination of Compound 1 and obinutuzumab was more efficacious than each single agent treatment and resulted in 111% TGI with 90% (1CR/8PR/9) overall response rate (FIG. 2).

Example 4 Effect of the Combination of Anti-CD20 mAb and BTK Inhibitor in Human REC-1 MCL Xenograft Model Method REC-1 cells were cultured in RPMI1640 complete medium supplemented with 10% (v/v) fetal bovine serum, and 100 µg/mL of penicillin and streptomycin. On the day of implantation, culture medium was replaced with fresh medium. Four hours later, media was removed and cells were collected as described above. Cells were re-suspended in cold (4° C.) PBS and same volume of matrigel was added to give a final concentration of $5 \times 10^7$ cells/mL for REC-1. Re-suspended cells were placed on ice prior to inoculation. The right flank region of each mouse was cleaned with 75% ethanol prior to cell inoculation. Animals were then injected subcutaneously with $1 \times 10^7$ REC-1 cells in 200 µl of cell suspension in the right front flank via a 26-gauge needle.

On day 9 after inoculation, animals were randomly divided into 6 groups with 7 mice per group. The groups consisted of a control group (no drug treatment), 25 mg/kg of Ibrutinib, 7.5 mg/kg of Compound 1, 200 µg/dose of rituximab, the combination of Compound 1 and rituximab (7.5 mg/kg and 200 µg/dose, respectively), and the combination of Ibrutinib and rituximab (25 mg/kg and 200 µg/dose, respectively). Compound 1 and ibrutinib were administered in a volume of 10 mL/kg body weight, assessed immediately before dosing and the volume dosed was adjusted accordingly. Compound 1 and Ibrutinib were administered by oral gavage (p.o.) twice daily (BID) and rituximab was administered by intraperitoneal (i.p.) injection once every four days (Q4D). After implantation, primary tumor volume was measured in two dimensions using a calliper.

Individual body weight was recorded twice weekly, with mice being monitored daily for clinical signs of toxicity for the duration of the study. Mice were euthanized using carbon dioxide when their tumor volume reached 2,500 mm³ after twice measurements, the tumor was ulcerated, or body weight loss exceeded 20%.

Figure 3:
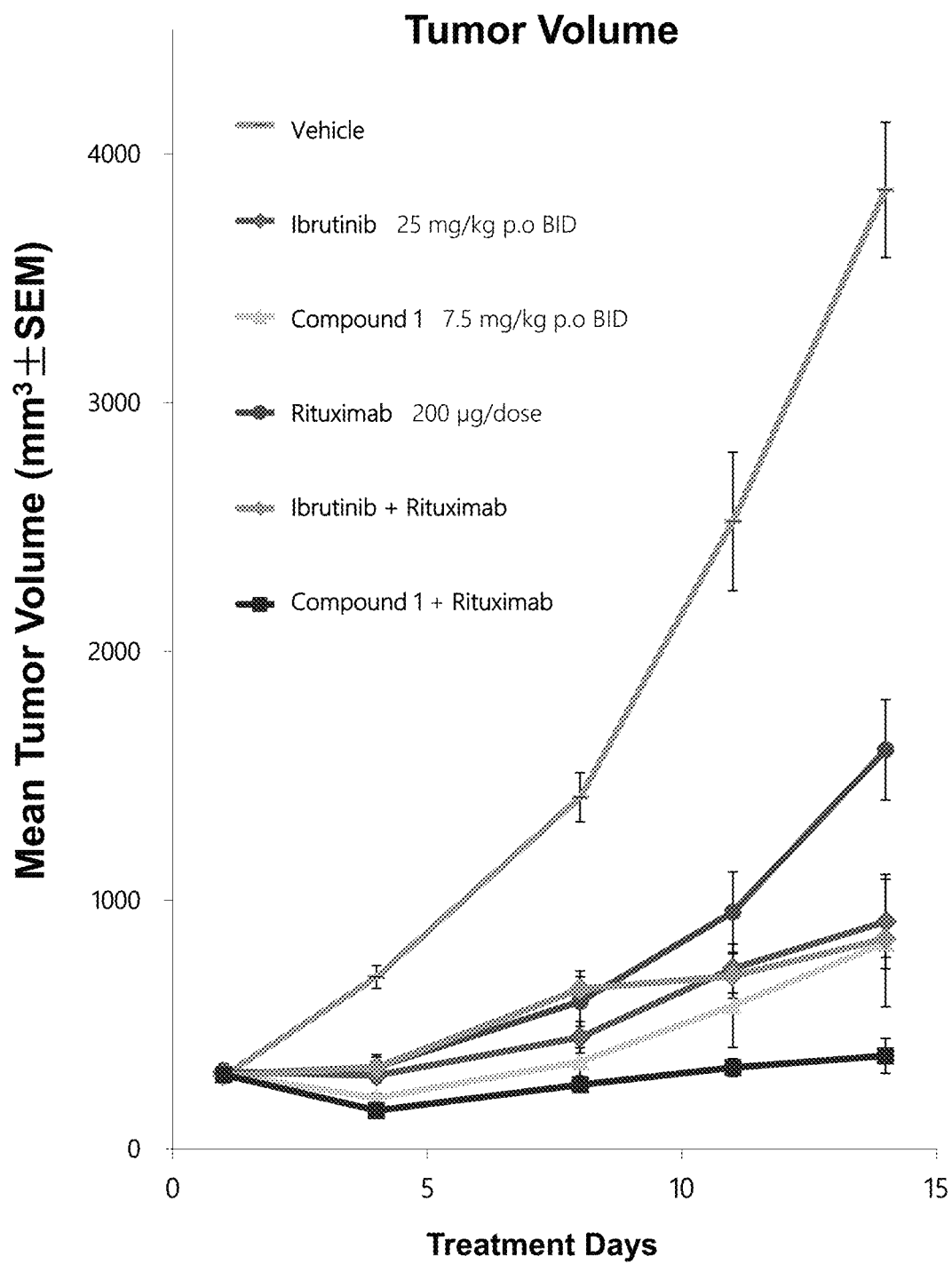
FIG. 3 shows the combination effects of anti-CD20 mAb (rituximab) and BTK inhibitor (including Compound 1 and ibrutinib) on tumor growth in human REC-1 MCL xenograft model.
Figure 4:
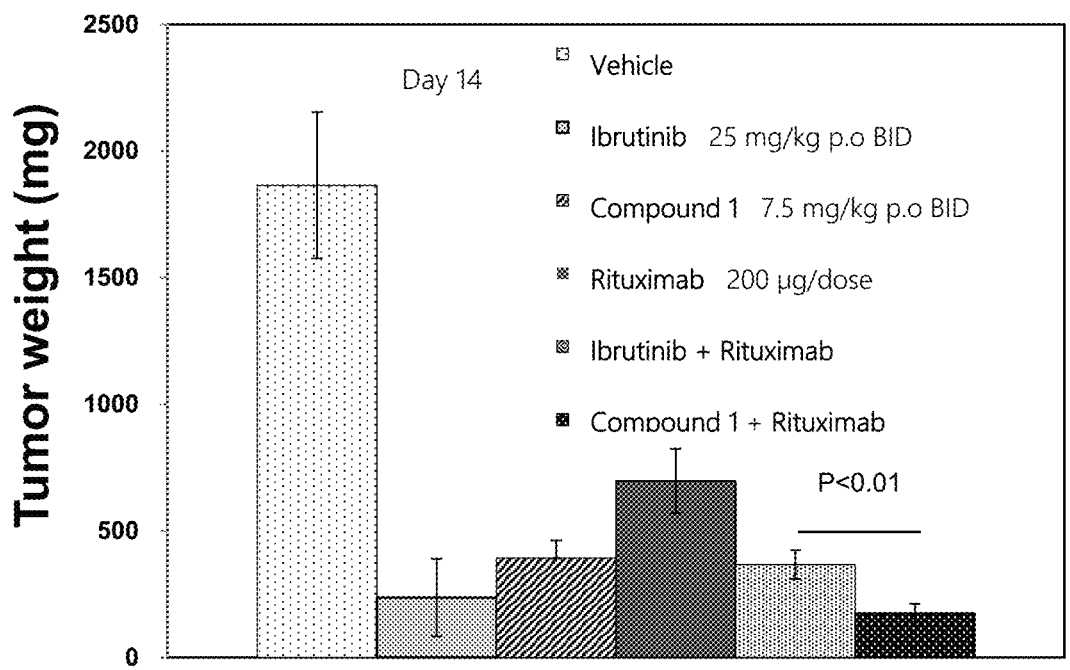
FIG. 4 shows the combination effects of anti-CD20 mAb (rituximab) and BTK inhibitor (including Compound 1 and ibrutinib) on tumor weight in human REC-1 MCL xenograft model (on Day 14).

Tumor volume was calculated using the formula: $V = 0.5 \times (a \times b^2)$ where a and b are the long and short diameters of the tumor, respectively. Tumor growth inhibition (TGI) was calculated using the following formula:

% TGI=100×[1−(treated$_t$/placebo$_t$)]

treated$_t$=treated tumor volume at time t
placebo$_t$=placebo tumor volume at time t Result As shown in FIG. 3, the tumor growth was retarded in rituximab, Compound 1 and Ibrutinib treatment groups. Compound 1 achieved similar anti-tumor effect as Ibrutinib, with 85% and 83% of TGI, respectively. The combination of Compound 1 and rituximab was more efficacious than each single agent, whereas combination of Ibrutinib with rituximab showed no obvious combo effect. On day 14, Compound 1 in combination with rituximab caused significant lower tumor weight when compared with combinational treatment of Ibrutinib and rituximab (FIG. 4).

Example 5 Effect of the Combination of Anti-PD-1 mAb and Btk Inhibitor in Human A431 Epidermoid Carcinoma Allogeneic Model Method On the day of implantation, human peripheral blood mononuclear cells (PBMCs) were isolated from 150 mL blood donated by a healthy volunteer. Briefly, peripheral blood was collected into vacuum blood collection tubes containing sodium heparin. PBMCs were separated by density gradient centrifugation using Histopaque-1077 and washed one time by Dulbecco's Phosphate Buffered Saline (DPBS). The cell pellet was suspended with DPBS at appropriate volume to give a final concentration of $1 \times 10^8$ cells/mL and placed on ice prior to inoculation.

A431 cells were cultured in DMEM complete medium supplemented with 10% (v/v) fetal bovine serum, and 100 µg/mL of penicillin and streptomycin. On the day of implantation, culture medium was replaced with fresh medium. Five hours later, media was removed and cells were collected as described above, except that cells were re-suspended in cold (4° C.) DPBS to give a final concentration of $5 \times 10^7$ cells/mL and placed on ice prior to inoculation. Mix the A431 cells, PBMCs and matrigel at the ratio of 1:1:2. NOD/SCID mice were pre-treated with cyclophosphamide (prepared in saline, 150 mg/kg, i.p.) and disulfiram (prepared in 0.8% Tween-80 in saline, 125 mg/kg, p.o., one hour after each dose of cyclophosphamide) once daily for one day. The right axilla region of each mouse was cleaned with 70% ethanol prior to cell inoculation. Each animal was injected subcutaneously with $2.5 \times 10^6$ A431 cells and $5 \times 10^6$ PBMC (200 µl cell mixture in 50% matrigel) in the right front flank via a 26-gauge needle 24 hours after the second dose of cyclophosphamide.

Starting from day 0 after cell inoculation, animals were randomly divided into four groups with 10-11 mice per group. The groups consisted of a control group (no drug treatment), 15 mg/kg of Compound 1, 10 mg/kg of Mab 1, and the combination of Compound 1 and Mab 1 (15 mg/kg and 10 mg/kg, respectively). Treatments were administered in a volume of 10 mL/kg body weight, assessed immediately before dosing and the volume dosed was adjusted accordingly. Compound 1 was administered by oral gavage (p.o.) twice daily (BID) and Mab 1 was administered by intraperitoneal (i.p.) injection once weekly (QW). After implantation, primary tumor volume was measured in two dimensions using a calliper.

Individual body weight was recorded twice weekly, with mice being monitored daily for clinical signs of toxicity for the duration of the study. Mice were euthanized using carbon dioxide when their tumor volume reached 2,500 mm³, the tumor was ulcerated, or body weight loss exceeded 20%.

Tumor volume was calculated using the formula: $V = 0.5 \times (a \times b^2)$ where a and b are the long and short diameters of the tumor, respectively.

Result

Figure 5:
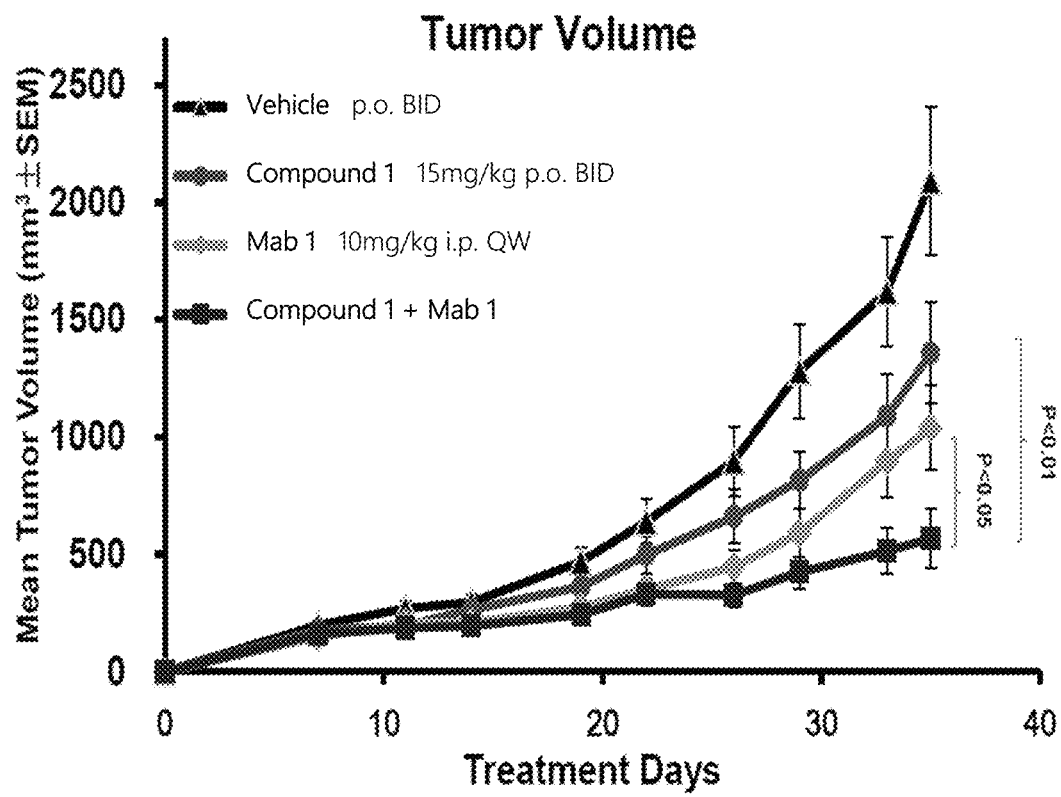
FIG. 5 shows the combination effects of anti-PD-1 mAb (Mab 1) and Compound 1 on tumor volume in human A431 epidermoid carcinoma allogeneic model.

In vivo efficacy of Compound 1 and Mab 1 was examined in human A431 epidermoid carcinoma allogeneic model. Mab 1, as a single agent, showed marginal effect in this model while Compound 1 showed no anti-tumor effect in this model. As shown in FIG. 5, the combination of these two agents demonstrated better efficacy than either single agent.

Example 6 Effect of the Combination of Anti-PD-1 mAb and BTK Inhibitor in Human A431 Epidermoid Carcinoma Allogeneic Model Method On the day of implantation, human peripheral blood mononuclear cells (PBMCs) were isolated from 150 mL blood donated by a healthy volunteer. Briefly, peripheral blood was collected into vacuum blood collection tubes containing sodium heparin. PBMCs were separated by density gradient centrifugation using Histopaque-1077 and washed one time by Dulbecco's Phosphate Buffered Saline (DPBS). The cell pellet was suspended with DPBS at appropriate volume to give a final concentration of $5 \times 10^7$ cells/mL and placed on ice prior to inoculation.

A431 cells were cultured in DMEM complete medium supplemented with 10% (v/v) fetal bovine serum, and 100 µg/mL of penicillin and streptomycin. On the day of implantation, culture medium was replaced with fresh medium. Five hours later, media was removed and cells were collected as described above, except that cells were re-suspended in cold (4° C.) DPBS to give a final concentration of $5 \times 10^7$ cells/mL and placed on ice prior to inoculation. Mix the A431 cells, PBMCs and matrigel at the ratio of 1:1:2. NOD/SCID mice were pre-treated with cyclophosphamide (prepared in saline, 150 mg/kg, i.p.) and disulfiram (prepared in 0.8% Tween-80 in saline, 125 mg/kg, p.o., one hour after each dose of cyclophosphamide) once daily for one day. The right axilla region of each mouse was cleaned with 70% ethanol prior to cell inoculation. Each animal was injected subcutaneously with $2.5 \times 10^6$ A431 cells and $2.5 \times 10^6$ PBMC (200 µl cell mixture in 50% matrigel) in the right front flank via a 26-gauge needle 24 hours after the second dose of cyclophosphamide.

Starting from day 0 after cell inoculation, animals were randomly divided into four groups with 10-11 mice per group. The groups consisted of a control group (no drug treatment), 15 mg/kg of Compound 1, 10 mg/kg of pembrolizumab, and the combination of Compound 1 and pembrolizumab (15 mg/kg and 10 mg/kg, respectively). Treatments were administered in a volume of 10 mL/kg body weight, assessed immediately before dosing and the volume dosed was adjusted accordingly. Compound 1 was administered by oral gavage (p.o.) twice daily (BID) and pembrolizumab was administered by intraperitoneal (i.p.) injection once weekly (QW). After implantation, primary tumor volume was measured in two dimensions using a calliper.

Individual body weight was recorded twice weekly, with mice being monitored daily for clinical signs of toxicity for the duration of the study. Mice were euthanized using carbon dioxide when their tumor volume reached 2,500 mm³, the tumor was ulcerated, or body weight loss exceeded 20%.

Tumor volume was calculated using the formula: $V=0.5 \times (a \times b^2)$ where a and b are the long and short diameters of the tumor, respectively.

Result

Figure 6:
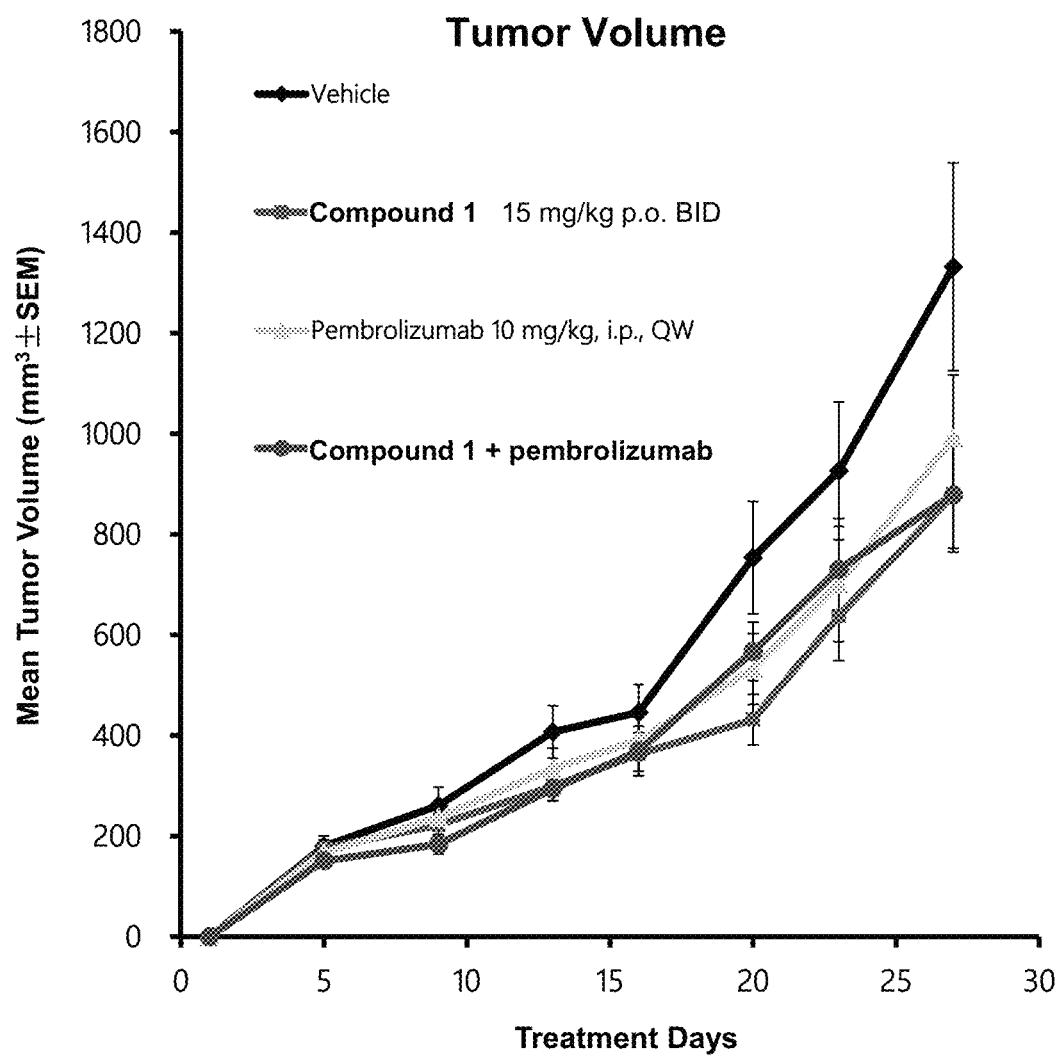
FIG. 6 shows the combination effects of Compound 1 and anti-PD-1 mAb (pembrolizumab) on tumor volume in human A431 epidermoid carcinoma allogeneic model.

In vivo efficacy of Compound 1 and pembrolizumab was examined in human A431 epidermoid carcinoma allogeneic model. Neither Compound 1 nor pembrolizumab showed anti-tumor effect in this model. As shown in FIG. 6, the combination of these two agents showed no combo effect.

Example 7A Selectivity for BTK Against ITK of BTK Inhibitor

Method:

Biochemical IC50 Determination of BTK and ITK

Compound 1 and Ibrutinib were tested for inhibition of BTK kinase in assays based on the time-resolved fluorescence-resonance energy transfer (TR-FRET) methodology. Briefly, the assays were carried out in 384-well low volume black plates in a reaction mixture containing BTK kinase, 5 µM ATP, 204 peptide substrate and 0-10 µM compound in buffer containing 50 mM Tris pH7.4, 10 mM MgCl$_2$, 2 mM MnCl$_2$, 0.1 mM EDTA, 1 mM DTT, 0.005% Tween-20, 20 nM SEB and 0.01% BSA. The kinase was incubated with compound for 60 minutes at room temperature and the reaction was initiated by the addition of ATP and peptide substrate. After reaction at room temperature for 60 minutes, an equal volume of stop/detection solution was added. Plates were sealed and incubated at room temperature for 1 hour, and the TR-FRET signals were recorded on a PHERAstar FS plate reader (BMG Labtech).

The protocol of ITK assay is similar to BTK assay except for the following modification: 304 ATP and 204 TK substrate were used in the kinase reaction.

ITK p-PLCγ1 Cellular Assay

Once activated by T cell receptor (TCR) aggregation, ITK directly phosphorylates PLCγ1 residue Tyr783 and subsequently actives NF-κB pathway, leading to increased production of Interleukin 2 (IL-2). Jurkat cells were treated with indicated concentration of ibrutinib or Compound 1 for 2 hrs. After treatment, cells were exposed to 10 mM of hydrogen peroxide for 10 min. PLCγ1, p-PLCγ1 (Y783) were detected by western blot analysis. IC50 is calculated using Quantity One and Prism 5 software.

ITK IL-2 Production Cellular Assay

HuT-78 cells and Hek293/OS8V cells were co-cultured in medium with indicated concentration of ibrutinib or Compound 1 for 20 hr. Potency of ibrutinib and Compound 1 were calculated basing on the medium IL-2 level.

BTK Occupation Cellular Assay

Z-138 cells were treated with increasing concentration of Compound 1 for 2 hours. The cell lysate were load to ELISA plate pre-immobilized with detection probe. After overnight incubation, plate was washed with PBST for 3 times and probe conjugated BTK protein was detected by a BTK antibody. The potency of compounds was calculated basing on the inhibition of ratio between signal intensity at OD450 nm. IC50 values were calculated with GraphPad Prism software using the sigmoidal dose-response function.

Results:

In the biochemical assay, selectivity of Compound 1 for BTK was 187-fold against ITK, whereas selectivity of Ibrutinib for BTK was 17-fold against ITK, indicating that Compound 1 was more selective than ibrutinib for inhibition of BTK vs. ITK.

In the PLCγ1 phosphorylation assay (Jurkat cell) and IL-2 production assay (HuT-78 cell), Compound 1 was shown to be 44-fold and 10-fold less effective than ibrutinib in inhibiting H$_2$O$_2$ induced PLCγ1 phosphorylation and IL-2 production, suggesting that Compound 1 is much weaker in ITK inhibition than ibrutinib.

TABLE 1

Compound 1 is highly selective for BTK against ITK

| Targets | Assays | IC$_{50}$ (nM) Ibrutinib | Compound 1 |
|---|---|---|---|
| BTK | BTK cell based Occupation Assay | 2.3 | 2.2 |
|  | BTK Biochemical Assay | 0.18 | 0.3 |
| ITK | p-PLCγ1 Cellular Assay | 77 | 3477 |
|  | IL-2 production Cellular Assay | 260 | 2536 |
|  | ITK Biochemical Assay | 3 | 56 |

Example 7B Effect of BTK Inhibitor on Anti-CD20 mAb Induced ADCC Effect

Method

Mino cells were cultured in RPMI1640 complete medium supplemented with 10% (v/v) fetal bovine serum, and 100 μg/mL of penicillin and streptomycin. NK92MI/CD16V cell line, overexpressing CD16 and FcRγ chain, was established from parental cell line NK92MI. The cells were maintained in MEM alpha supplemented with 0.2 mM inositol; 0.1 mM 2-mercaptoethanol; 0.02 mM folic acid; 1×NEAA; adjust to a final concentration of 20% (v/v) fetal bovine serum and 100 μg/mL of penicillin and streptomycin.

Mino cells ($2\times10^4$ cells/well) as the target cells (T) were plated into 96-well plate in triplicates. Cells were treated with vehicle or various concentrations of BTK inhibitors for one hour, followed by co-seeding with NK92MI cells ($4\times10^4$ cells/well, as the effector cells (E)) and co-treatment with vehicle or obinutuzumab (2 ug/well) for additional 24 hrs. After incubation, the cell-free supernatants of each well were collected, and the levels of human IFN-γ were measured using Human IFN-γ ELISA Ready-SET-Go kit.

Result

Figure 7:
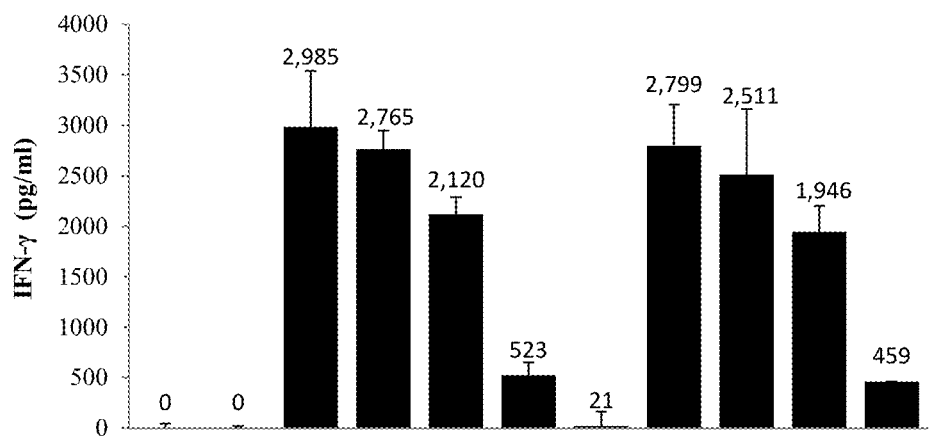
FIG. 7 shows the effect of BTK inhibitor (including Compound 1 and ibrutinib) on anti-CD20 mAb (obinutuzumab) induced ADCC effect.

Obinutuzumab-induced ADCC was assessed by IFN-γ secretion in co-culture of NK cells and Mino cells (FIG. 7). Ibrutinib inhibited IFN-γ secretion in a dose-depended manner. At 1 μM, ibrutinib strongly inhibited IFN-γ secretion. In contrast, Compound 1 was much less effective in this assay. At high dose tested (10 μM), it had similar inhibition effect on IFN-γ secretion as ibrutinib at 1 μM. The result suggest that Compound 1 is at least 10-fold weaker than ibrutinib in inhibiting obinutuzumab-induced ADCC. This is consistent with Compound 1 being more selective BTK inhibitor, with much weaker ITK inhibition activity than ibrutinib in both biochemical and cellular assays.

Example 8 Clinical Trial Phase Result on BTK Inhibitor Combined with Anti-CD20 Antibody The multi-center, open-label Phase 1 trial of Compound 1 with obinutuzumab in patients with B-cell malignancies is being conducted in Australia and the United States and consists of a dose-escalation phase and a dose-expansion phase in disease-specific cohorts, which include treatment naïve (TN) or relapsed/refractory (R/R) chronic lymphocytic (CLL)/small lymphocytic lymphoma (SLL) and R/R follicular lymphoma (FL). The dose-escalation component is testing Compound 1 at 320 mg once daily (QD) or 160 mg twice daily (BID) in 28-day cycles, in combination with obinutuzumab. And, obinutuzumab was administered in line with standard CLL dosing (three loading doses of 1000 mg weekly followed by 1000 mg on day one of cycles 2-6). The ongoing dose-expansion component is testing doses of Compound 1 at 160 mg BID with the same obinutuzumab schedule. As of Mar. 31, 2017, 45 patients with CLL/SLL and 17 patients with FL were enrolled in the trial.

43 patients with CLL/SLL (18 TN, 25R/R) and 15 patients with R/R FL had greater than 12 weeks of follow-up and were evaluable for efficacy. In TN CLL/SLL, after a median follow-up of 7.0 months (2.8-11.8 months), the overall response rate (ORR) was 89% with complete responses (CRs) in 22% and partial responses (PRs) in 67% of patients. Stable disease (SD) was observed in 11% of patients. In R/R CLL/SLL, at a median follow-up time of 8.0 months (3.8-14.0 months) the ORR was 92% with CRs in 16% and PRs in 76% of patients. SD was observed in 4% of patients. In R/R FL, at a median follow-up time of 6.2 months (1.2-10.7 months), the ORR was 73% with CRs in 33% and PRs in 40% of patients. Stable disease was observed in 13% of patients. One patient with R/R CLL/SLL had progressive disease (Richter's transformation), and two patients with R/R FL had progressive disease.

The multi-center, open-label Phase 1 trial of Compound 1 with obinutuzumab in patients with B-cell malignancies is being conducted in Australia and the United States and consists of a dose-escalation phase and a dose-expansion phase in disease-specific cohorts, which include treatment naïve (TN) or relapsed/refractory (R/R) chronic lymphocytic (CLL)/small lymphocytic lymphoma (SLL) and R/R follicular lymphoma (FL). The dose-escalation component is testing Compound 1 at 320 mg once daily (QD) or 160 mg twice daily (BID) in 28-day cycles, in combination with obinutuzumab. And, obinutuzumab was administered in line with standard CLL dosing (three loading doses of 1000 mg weekly followed by 1000 mg on day one of cycles 2-6). The ongoing dose-expansion component is testing doses of Compound 1 at 160 mg BID with the same obinutuzumab schedule. As of Mar. 31, 2017, 45 patients with CLL/SLL and 17 patients with FL were enrolled in the trial.

The foregoing examples and description of certain embodiments should be taken as illustrating, rather than as limiting the present invention as defined by the claims. As will be readily appreciated, numerous variations and combinations of the features set forth above can be utilized without departing from the present invention as set forth in the claims. All such variations are intended to be included within the scope of the present invention. All references cited are incorporated herein by reference in their entireties.

The invention claimed is:

1. A method for the delay of progression or treatment of a B cell cancer in a subject, comprising administering to the subject in need thereof (S)-7-(1-acryloylpiperidin-4-yl)-2-(4-phenoxyphenyl)-4,5,6,7-tetra-hydropyrazolo[1,5-a]pyrimidine-3-carboxamide, or a pharmaceutically acceptable salt thereof, at a dose of 320 mg once a day (QD) or 160 mg twice a day (BID) in 28-day cycles, in combination with obinutuzumab administered by three loading doses of 1000 mg weekly followed by 1000 mg on day one of cycles 2-6, wherein the subject is a human.

2. The method of claim 1, wherein the delay of progression or treatment of a B cell cancer in a subject is delay of progression of B cell cancer growth or inhibiting B cell cancer growth in the subject.

3. The method of claim 1, wherein the B-cell cancer is a relapsed or refractory B-cell cancer.

4. The method of claim 3, wherein the relapsed or refractory B-cell cancer is diffuse large B-cell lymphoma (DLBCL), activated B-cell diffuse large B-cell lymphoma (ABC-DLBCL), germinal center B-cell diffuse large B-cell lymphoma (GCB-DLBCL) or non-germinal center B-cell diffuse large B-cell lymphoma (non-GCB DLCBCL).

5. The method of claim 1, wherein the B-cell cancer is a metastasized B-cell cancer.

6. The method of claim 5, wherein the metastasized B-cell cancer is diffuse large B-cell lymphoma (DLBCL), activated B-cell diffuse large B-cell lymphoma (ABC-DLBCL), germinal center B-cell diffuse large B-cell lymphoma (GCB-DLBCL) or non-germinal center B-cell diffuse large B-cell lymphoma (non-GCB DLCBCL).

7. The method of claim 1, wherein the B-cell cancer is chronic lymphocytic leukemia (CLL), small lymphocytic lymphoma (SLL), non-CLL/SLL lymphoma, follicular lymphoma (FL), mantle cell lymphoma (MCL), marginal zone lymphoma (MZL), Waldenström macroglobulinemia (WM), Hairy cell leukemia (HCL), Burkitt's-like leukemia (BL), B cell prolymphocytic leukemia (B-PLL), diffuse large B cell lymphoma (DLBCL), primary central nervous system lymphoma (PCNSL), secondary central nervous system lymphoma (SCNSL) of breast or testicular origin, multiple myeloma, or a combination of two or more thereof.

8. The method of claim 7, wherein the DLBCL is activated B-cell diffuse large B-cell lymphoma (ABC-DLBCL), germinal center B-cell diffuse large B-cell lymphoma (GCB-DLBCL), non-germinal center B-cell diffuse large B-cell lymphoma (Non-GCB DLBCL), or diffuse large B-cell lymphoma (DLBCL) with undetermined subtype.

9. The method of claim 7, wherein the B-cell cancer is follicular lymphoma (FL).

10. The method of claim 9, wherein the FL is relapsed or refractory.

11. The method of claim 9, wherein the obinutuzumab is administered at a dose of 1,000 mg intravenously on days 1, 8, and 15 of cycle 1, followed by 1,000 mg intravenously on day 1 of each cycle of cycles 2 to 6; and each cycle is 28 days.

12. The method of claim 11, wherein the FL is relapsed or refractory.

13. The method of claim 9, wherein the (S)-7-(1-acryloylpiperidin-4-yl)-2-4-phenoxyphenyl)-4,5,6,7-tetra-hydropyrazolo[1,5-a]pyrimidine-3-carboxamide, or a pharmaceutically acceptable salt thereof, is administered orally, and the obinutuzumab is administered intravenously.

14. The method of claim 13, wherein the (S)-7-(1-acryloylpiperidin-4-yl)-2-4-phenoxyphenyl)-4,5,6,7-tetra-hydropyrazolo[1,5-a]pyrimidine-3-carboxamide, or a pharmaceutically acceptable salt thereof, is administered at a dose of 160 mg twice a day (BID).

15. The method of claim 14, wherein the FL is relapsed or refractory.

16. The method of claim 13, wherein the (S)-7-(1-acryloylpiperidin-4-yl)-2-4-phenoxyphenyl)-4,5,6,7-tetra-hydropyrazolo[1,5-a]pyrimidine-3-carboxamide, or a pharmaceutically acceptable salt thereof, is administered at a dose of 320 mg once a day (QD).

17. The method of claim 16, wherein the FL is relapsed or refractory.

18. The method of claim 1, wherein the (S)-7-(1-acryloylpiperidin-4-yl)-2-4-phenoxyphenyl)-4,5,6,7-tetra-hydropyrazolo[1,5-a]pyrimidine-3-carboxamide, or a pharmaceutically acceptable salt thereof, is administered orally, and the obinutuzumab is administered intravenously.

19. The method of claim 11, wherein the (S)-7-(1-acryloylpiperidin-4-yl)-2-4-phenoxyphenyl)-4,5,6,7-tetra-hydropyrazolo[1,5-a]pyrimidine-3-carboxamide, or a pharmaceutically acceptable salt thereof, is administered orally.

* * * * *

UNITED STATES PATENT AND TRADEMARK OFFICE
CERTIFICATE OF CORRECTION

| | | |
|---|---|---|
| PATENT NO. | : 11,701,357 B2 | Page 1 of 1 |
| APPLICATION NO. | : 16/326467 | |
| DATED | : July 18, 2023 | |
| INVENTOR(S) | : Nan Hu et al. | |

It is certified that error appears in the above-identified patent and that said Letters Patent is hereby corrected as shown below:

On the Title Page

Item (54) and in the Specification Column 1, Lines 1-3, please delete "TREATMENT OF B CELL CANCERS USING A COMBINATION COMPRISING BTK INHIBITORS" and replace with --TREATMENT OF B CELL CANCERS USING A COMBINATION COMPRISING BTK INHIBITORS AND OBINUTUZUMAB--.

In the Claims

Claim 13, Column 107, Line 27, please replace "2-4-phenoxyphenyl)" with --2-(4-phenoxyphenyl)--.

Claim 14, Column 108, Line 5, please replace "2-4-phenoxyphenyl)" with --2-(4-phenoxyphenyl)--.

Claim 16, Column 108, Line 12, please replace "2-4-phenoxyphenyl)" with --2-(4-phenoxyphenyl)--.

Claim 18, Column 108, Line 19, please replace "2-4-phenoxyphenyl)" with --2-(4-phenoxyphenyl)--.

Claim 19, Column 108, Line 24, please replace "2-4-phenoxyphenyl)" with --2-(4-phenoxyphenyl)--.

Signed and Sealed this
Thirty-first Day of October, 2023

Katherine Kelly Vidal
*Director of the United States Patent and Trademark Office*

SEQUENCE LISTING

```
<160> NUMBER OF SEQ ID NOS: 90

<210> SEQ ID NO 1
<211> LENGTH: 444
<212> TYPE: DNA
<213> ORGANISM: Homo sapiens
```

<400> SEQUENCE: 1

```
ccaggatggt tcttagactc cccagacagg ccctggaacc cccccacctt ctccccagcc    60
ctgctcgtgg tgaccgaagg ggacaacgcc accttcacct gcagcttctc caacacatcg   120
gagagcttcg tgctaaactg gtaccgcatg agcccagca accagacgga caagctggcc   180
gccttccccg aggaccgcag ccagcccggc caggactgcc gcttccgtgt cacacaactg   240
cccaacgggc gtgacttcca catgagcgtg gtcagggccc ggcgcaatga cagcggcacc   300
tacctctgtg gggccatctc cctggccccc aaggcgcaga tcaaagagag cctgcgggca   360
gagctcaggg tgacagagag aagggcagaa gtgcccacag cccaccccag ccctcaccc   420 aggccagccg gccagttcca aacc                                          444
```

<210> SEQ ID NO 2
<211> LENGTH: 148
<212> TYPE: PRT
<213> ORGANISM: Homo sapiens

<400> SEQUENCE: 2

```
Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
            20                  25                  30

Thr Cys Ser Phe Ser Asn Thr Ser Glu Ser Phe Val Leu Asn Trp Tyr
        35                  40                  45

Arg Met Ser Pro Ser Asn Gln Thr Asp Lys Leu Ala Ala Phe Pro Glu
    50                  55                  60

Asp Arg Ser Gln Pro Gly Gln Asp Cys Arg Phe Arg Val Thr Gln Leu
65                  70                  75                  80

Pro Asn Gly Arg Asp Phe His Met Ser Val Val Arg Ala Arg Arg Asn
                85                  90                  95

Asp Ser Gly Thr Tyr Leu Cys Gly Ala Ile Ser Leu Ala Pro Lys Ala
            100                 105                 110

Gln Ile Lys Glu Ser Leu Arg Ala Glu Leu Arg Val Thr Glu Arg Arg
        115                 120                 125

Ala Glu Val Pro Thr Ala His Pro Ser Pro Ser Pro Arg Pro Ala Gly
    130                 135                 140

Gln Phe Gln Thr
145
```

<210> SEQ ID NO 3
<211> LENGTH: 354
<212> TYPE: DNA
<213> ORGANISM: Mus musculus

<400> SEQUENCE: 3

```
caggtgcagc tgaaggagtc aggacctggc ctggtggcgc cctcaaagaa cctgtccatc    60
acttgcactg tctctgggtt ttcattaacc agctatggtg tacactggat cgccagcct   120 ccaggaaagg gactggaatg gctgggagta atatgggccg gtggaagcac aaattataat   180
tcggctctca gtccagact gagcatcagc aaagacaact ccaggagcca agttttctta   240
agaatgaaca gtctgcaaac tgatgacaca gccatgtact actgtgccag agcctatggt   300
aactactggt acatcgatgt ctggggcgca gggaccacgg tcaccgtctc ctca         354
```

<210> SEQ ID NO 4
<211> LENGTH: 118

```
<212> TYPE: PRT
<213> ORGANISM: Mus musculus

<400> SEQUENCE: 4

Gln Val Gln Leu Lys Glu Ser Gly Pro Gly Leu Val Ala Pro Ser Lys
1               5                   10                  15

Asn Leu Ser Ile Thr Cys Thr Val Ser Gly Phe Ser Leu Thr Ser Tyr
            20                  25                  30

Gly Val His Trp Ile Arg Gln Pro Pro Gly Lys Gly Leu Glu Trp Leu
        35                  40                  45

Gly Val Ile Trp Ala Gly Gly Ser Thr Asn Tyr Asn Ser Ala Leu Met
    50                  55                  60

Ser Arg Leu Ser Ile Ser Lys Asp Asn Ser Arg Ser Gln Val Phe Leu
65                  70                  75                  80

Arg Met Asn Ser Leu Gln Thr Asp Asp Thr Ala Met Tyr Tyr Cys Ala
                85                  90                  95

Arg Ala Tyr Gly Asn Tyr Trp Tyr Ile Asp Val Trp Gly Ala Gly Thr
            100                 105                 110

Thr Val Thr Val Ser Ser
        115

<210> SEQ ID NO 5
<211> LENGTH: 321
<212> TYPE: DNA
<213> ORGANISM: Mus musculus

<400> SEQUENCE: 5
gacattgtga tgacccagac tcccaaattc ctgcttgtat cagcaggaga cagggttacc      60
ataacctgca aggccagtca gagtgtgagt aatgatgtag cttggtacca acagaagcca     120
gggcagtctc ctaaactgct gataaactat gcatttcatc gcttcactgg agtccctgat     180
cgtttcactg gcagtggata tgggacggat ttcattttca ccatcagcac tgtgcaggct     240
gaagacctgg cagtttattt ctgtcaccag gcttatagtt ctccgtacac gttcggaggg     300
gggaccaagc tggaaatgaa a                                              321

<210> SEQ ID NO 6
<211> LENGTH: 107
<212> TYPE: PRT
<213> ORGANISM: Mus musculus

<400> SEQUENCE: 6

Asp Ile Val Met Thr Gln Thr Pro Lys Phe Leu Leu Val Ser Ala Gly
1               5                   10                  15

Asp Arg Val Thr Ile Thr Cys Lys Ala Ser Gln Ser Val Ser Asn Asp
            20                  25                  30

Val Ala Trp Tyr Gln Gln Lys Pro Gly Gln Ser Pro Lys Leu Leu Ile
        35                  40                  45

Asn Tyr Ala Phe His Arg Phe Thr Gly Val Pro Asp Arg Phe Thr Gly
    50                  55                  60

Ser Gly Tyr Gly Thr Asp Phe Ile Phe Thr Ile Ser Thr Val Gln Ala
65                  70                  75                  80

Glu Asp Leu Ala Val Tyr Phe Cys His Gln Ala Tyr Ser Ser Pro Tyr
                85                  90                  95

Thr Phe Gly Gly Gly Thr Lys Leu Glu Met Lys
            100                 105
```

<210> SEQ ID NO 7
<211> LENGTH: 342
<212> TYPE: DNA
<213> ORGANISM: Mus musculus

<400> SEQUENCE: 7

```
cagatccagt tggtgcagtc tggacctgag ctgaagaagc ctggagagac agtcaagatc      60
tcctgcaagg cttctgggta taccttcaca aactatggaa tgaactgggt gaagcaggct     120
ccaggaaagg gtttaaagtg gatgggctgg ataaacaata ataatggaga gccaacatat     180
gctgaagagt tcaagggacg gtttgccttc tctttggaaa cctctgccag cactgcctat     240
ttgcagatca acaacctcaa aaatgaggac acggctacat atttctgtgc aagagatgtt     300
atggactatt ggggtcaagg aacctcagtc accgtctcct ca                       342
```

<210> SEQ ID NO 8
<211> LENGTH: 114
<212> TYPE: PRT
<213> ORGANISM: Mus musculus

<400> SEQUENCE: 8

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asn Tyr
            20                  25                  30

Gly Met Asn Trp Val Lys Gln Ala Pro Gly Lys Gly Leu Lys Trp Met
        35                  40                  45

Gly Trp Ile Asn Asn Asn Asn Gly Glu Pro Thr Tyr Ala Glu Glu Phe
    50                  55                  60

Lys Gly Arg Phe Ala Phe Ser Leu Glu Thr Ser Ala Ser Thr Ala Tyr
65                  70                  75                  80

Leu Gln Ile Asn Asn Leu Lys Asn Glu Asp Thr Ala Thr Tyr Phe Cys
                85                  90                  95

Ala Arg Asp Val Met Asp Tyr Trp Gly Gln Gly Thr Ser Val Thr Val
            100                 105                 110

Ser Ser

<210> SEQ ID NO 9
<211> LENGTH: 330
<212> TYPE: DNA
<213> ORGANISM: Mus musculus

<400> SEQUENCE: 9

```
gacattgtgc tgacccaatc tccagcttct ttggctgtgt ctctagggca gagggccacc      60
atatcctgca gagccagtga aagtgttgat aattatggct atagttttat gcactggtac     120
cagcagaaac aggacagcc accccaactc ctcatctatc gtgcatccaa cctagaatct     180
gggatccctg ccaggttcag tggcagtggg tctaggacag gcttcaccct caccattaat     240
cctgtggagg ctgatgatgt tgcaacctat tactgtcagc aaagtaaaga atatccgacg     300
ttcggtggag gcaccaagct ggaagtcaaa                                      330
```

<210> SEQ ID NO 10
<211> LENGTH: 110
<212> TYPE: PRT
<213> ORGANISM: Mus musculus

<400> SEQUENCE: 10

Asp Ile Val Leu Thr Gln Ser Pro Ala Ser Leu Ala Val Ser Leu Gly

```
            1               5                  10                 15
         Gln Arg Ala Thr Ile Ser Cys Arg Ala Ser Glu Ser Val Asp Asn Tyr
                        20                  25                 30
         Gly Tyr Ser Phe Met His Trp Tyr Gln Gln Lys Pro Gly Gln Pro Pro
                    35                  40                 45
         Gln Leu Leu Ile Tyr Arg Ala Ser Asn Leu Glu Ser Gly Ile Pro Ala
                50                  55                 60
         Arg Phe Ser Gly Ser Gly Ser Arg Thr Gly Phe Thr Leu Thr Ile Asn
         65                  70                  75                 80
         Pro Val Glu Ala Asp Asp Val Ala Thr Tyr Tyr Cys Gln Gln Ser Lys
                         85                  90                 95
         Glu Tyr Pro Thr Phe Gly Gly Gly Thr Lys Leu Glu Val Lys
                    100                 105                110

<210> SEQ ID NO 11
<211> LENGTH: 10
<212> TYPE: PRT
<213> ORGANISM: Mus musculus

<400> SEQUENCE: 11

Gly Phe Ser Leu Thr Ser Tyr Gly Val His
1               5                  10

<210> SEQ ID NO 12
<211> LENGTH: 16
<212> TYPE: PRT
<213> ORGANISM: Mus musculus

<400> SEQUENCE: 12

Val Ile Trp Ala Gly Gly Ser Thr Asn Tyr Asn Ser Ala Leu Met Ser
1               5                   10                  15

<210> SEQ ID NO 13
<211> LENGTH: 12
<212> TYPE: PRT
<213> ORGANISM: Mus musculus

<400> SEQUENCE: 13

Ala Arg Ala Tyr Gly Asn Tyr Trp Tyr Ile Asp Val
1               5                   10

<210> SEQ ID NO 14
<211> LENGTH: 11
<212> TYPE: PRT
<213> ORGANISM: Mus musculus

<400> SEQUENCE: 14

Lys Ala Ser Gln Ser Val Ser Asn Asp Val Ala
1               5                   10

<210> SEQ ID NO 15
<211> LENGTH: 7
<212> TYPE: PRT
<213> ORGANISM: Mus musculus

<400> SEQUENCE: 15

Tyr Ala Phe His Arg Phe Thr
1               5

<210> SEQ ID NO 16
<211> LENGTH: 9
<212> TYPE: PRT
```

```
<213> ORGANISM: Mus musculus

<400> SEQUENCE: 16

His Gln Ala Tyr Ser Ser Pro Tyr Thr
1               5

<210> SEQ ID NO 17
<211> LENGTH: 10
<212> TYPE: PRT
<213> ORGANISM: Mus musculus

<400> SEQUENCE: 17

Gly Tyr Thr Phe Thr Asn Tyr Gly Met Asn
1               5                   10

<210> SEQ ID NO 18
<211> LENGTH: 17
<212> TYPE: PRT
<213> ORGANISM: Mus musculus

<400> SEQUENCE: 18

Trp Ile Asn Asn Asn Gly Glu Pro Thr Tyr Ala Glu Glu Phe Lys
1               5                   10                  15

Gly

<210> SEQ ID NO 19
<211> LENGTH: 7
<212> TYPE: PRT
<213> ORGANISM: Mus musculus

<400> SEQUENCE: 19

Ala Arg Asp Val Met Asp Tyr
1               5

<210> SEQ ID NO 20
<211> LENGTH: 15
<212> TYPE: PRT
<213> ORGANISM: Mus musculus

<400> SEQUENCE: 20

Arg Ala Ser Glu Ser Val Asp Asn Tyr Gly Tyr Ser Phe Met His
1               5                   10                  15

<210> SEQ ID NO 21
<211> LENGTH: 7
<212> TYPE: PRT
<213> ORGANISM: Mus musculus

<400> SEQUENCE: 21

Arg Ala Ser Asn Leu Glu Ser
1               5

<210> SEQ ID NO 22
<211> LENGTH: 8
<212> TYPE: PRT
<213> ORGANISM: Mus musculus

<400> SEQUENCE: 22

Gln Gln Ser Lys Glu Tyr Pro Thr
1               5

<210> SEQ ID NO 23
<211> LENGTH: 354
<212> TYPE: DNA
```

<213> ORGANISM: Artificial Sequence
<220> FEATURE:
<223> OTHER INFORMATION: 317-4B6 cDNA-Vh

<400> SEQUENCE: 23

```
caggtgcagc tgcaggagtc gggaccagga ctggtgaagc cttcggagac cctgtccctc      60
acctgcactg tctctgggtt ttcattaacc agctatggtg tacactggat ccggcagccc     120
ccagggaagg gactggagtg gatcggggtc atatacgccg atggaagcac aaattataat     180
ccctccctca agagtcgagt gaccatatca aagacacct ccaagaacca ggtttccctg      240
aagctgagct ctgtgaccgc tgcggacacg gccgtgtatt actgtgcgag agcctatggt     300
aactactggt acatcgatgt ctggggccaa gggaccacgg tcaccgtctc ctca           354
```

<210> SEQ ID NO 24
<211> LENGTH: 118
<212> TYPE: PRT
<213> ORGANISM: Artificial Sequence
<220> FEATURE:
<223> OTHER INFORMATION: 317-4B6 pro-Vh

<400> SEQUENCE: 24

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Ser Tyr
            20                  25                  30

Gly Val His Trp Ile Arg Gln Pro Pro Gly Lys Gly Leu Glu Trp Ile
        35                  40                  45

Gly Val Ile Tyr Ala Asp Gly Ser Thr Asn Tyr Asn Pro Ser Leu Lys
    50                  55                  60

Ser Arg Val Thr Ile Ser Lys Asp Thr Ser Lys Asn Gln Val Ser Leu
65                  70                  75                  80

Lys Leu Ser Ser Val Thr Ala Ala Asp Thr Ala Val Tyr Tyr Cys Ala
                85                  90                  95

Arg Ala Tyr Gly Asn Tyr Trp Tyr Ile Asp Val Trp Gly Gln Gly Thr
            100                 105                 110

Thr Val Thr Val Ser Ser
        115
```

<210> SEQ ID NO 25
<211> LENGTH: 321
<212> TYPE: DNA
<213> ORGANISM: Artificial Sequence
<220> FEATURE:
<223> OTHER INFORMATION: 317-4B6 cDNA-Vk

<400> SEQUENCE: 25

```
gacatcgtga tgacccagtc tccagactcc ctggctgtgt ctctgggcga gagggccacc      60
atcaactgca gtccagcga gagtgtgagt aatgatgtag cttggtacca gcagaaacca     120
ggacagcctc ctaagctgct cattaactat gcatttcatc gcttcactgg ggtccctgac     180
cgattcagtg gcagcgggta tgggacagat ttcactctca ccatcagcag cctgcaggct     240
gaagatgtgg cagtttatta ctgtcaccag gcttatagtt ctccgtacac gtttggccag     300
gggaccaagc tggagatcaa a                                                321
```

<210> SEQ ID NO 26
<211> LENGTH: 107
<212> TYPE: PRT
<213> ORGANISM: Artificial Sequence
<220> FEATURE:
<223> OTHER INFORMATION: 317-4B6 pro-Vk

<400> SEQUENCE: 26

Asp Ile Val Met Thr Gln Ser Pro Asp Ser Leu Ala Val Ser Leu Gly
1               5                   10                  15

Glu Arg Ala Thr Ile Asn Cys Lys Ser Ser Glu Ser Val Ser Asn Asp
            20                  25                  30

Val Ala Trp Tyr Gln Gln Lys Pro Gly Gln Pro Pro Lys Leu Leu Ile
        35                  40                  45

Asn Tyr Ala Phe His Arg Phe Thr Gly Val Pro Asp Arg Phe Ser Gly
    50                  55                  60

Ser Gly Tyr Gly Thr Asp Phe Thr Leu Thr Ile Ser Ser Leu Gln Ala
65                  70                  75                  80

Glu Asp Val Ala Val Tyr Tyr Cys His Gln Ala Tyr Ser Ser Pro Tyr
                85                  90                  95

Thr Phe Gly Gln Gly Thr Lys Leu Glu Ile Lys
            100                 105

<210> SEQ ID NO 27
<211> LENGTH: 342
<212> TYPE: DNA
<213> ORGANISM: Artificial Sequence
<220> FEATURE:
<223> OTHER INFORMATION: 326-4A3 cDNA-Vh

<400> SEQUENCE: 27
caggtgcagc tggtgcagag cggcagcgag ctgaagaagc ccggcgccag cgtgaaggtg     60
agctgcaagg ccagcggcta caccttcacc aactacggca tgaactgggt gagacaggcc    120
cccggccagg gcctgaagtg gatgggctgg atcaacaaca acaacgccga gcccacctac    180
gcccaggact tcagaggcag attcgtgttc agcctggaca ccagcgccag caccgcctac    240
ctgcagatca gcagcctgaa gaccgaggac accgccgtgt actactgcgc cagagacgtg    300
atggactact ggggccaggg caccctggtg accgtgagca gc                       342

<210> SEQ ID NO 28
<211> LENGTH: 114
<212> TYPE: PRT
<213> ORGANISM: Artificial Sequence
<220> FEATURE:
<223> OTHER INFORMATION: 326-4A3 pro-Vh

<400> SEQUENCE: 28

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asn Tyr
            20                  25                  30

Gly Met Asn Trp Val Arg Gln Ala Pro Gly Gln Gly Leu Lys Trp Met
        35                  40                  45

Gly Trp Ile Asn Asn Asn Asn Ala Glu Pro Thr Tyr Ala Gln Asp Phe
    50                  55                  60

Arg Gly Arg Phe Val Phe Ser Leu Asp Thr Ser Ala Ser Thr Ala Tyr
65                  70                  75                  80

Leu Gln Ile Ser Ser Leu Lys Thr Glu Asp Thr Ala Val Tyr Tyr Cys
                85                  90                  95

Ala Arg Asp Val Met Asp Tyr Trp Gly Gln Gly Thr Leu Val Thr Val
            100                 105                 110

Ser Ser

<210> SEQ ID NO 29
<211> LENGTH: 330
<212> TYPE: DNA
<213> ORGANISM: Artificial Sequence
<220> FEATURE:
<223> OTHER INFORMATION: 326-4A3 cDNA-Vk

<400> SEQUENCE: 29

```
gacattgtgc tgacccagtc tccagcctcc ttggccgtgt ctccaggaca gagggccacc    60
atcacctgca gagccagtga aagtgttgat aattatggct atagttttat gcactggtat   120
cagcagaaac caggacaacc tcctaaactc ctgatttacc gtgcatccaa cctagaatct   180
ggggtcccag ccaggttcag cggcagtggg tctgggaccg atttcaccct cacaattaat   240
cctgtggaag ctgaggatac tgcaaattat tactgtcagc aaagtaaaga atatccgacg   300
ttcggcggag ggaccaaggt ggagatcaaa                                     330
```

<210> SEQ ID NO 30
<211> LENGTH: 110
<212> TYPE: PRT
<213> ORGANISM: Artificial Sequence
<220> FEATURE:
<223> OTHER INFORMATION: 326-4A3 pro-Vk

<400> SEQUENCE: 30

```
Asp Ile Val Leu Thr Gln Ser Pro Ala Ser Leu Ala Val Ser Pro Gly
1               5                   10                  15

Gln Arg Ala Thr Ile Thr Cys Arg Ala Ser Glu Ser Val Asp Asn Tyr
            20                  25                  30

Gly Tyr Ser Phe Met His Trp Tyr Gln Gln Lys Pro Gly Gln Pro Pro
        35                  40                  45

Lys Leu Leu Ile Tyr Arg Ala Ser Asn Leu Glu Ser Gly Val Pro Ala
    50                  55                  60

Arg Phe Ser Gly Ser Gly Ser Gly Thr Asp Phe Thr Leu Thr Ile Asn
65                  70                  75                  80

Pro Val Glu Ala Glu Asp Thr Ala Asn Tyr Tyr Cys Gln Gln Ser Lys
                85                  90                  95

Glu Tyr Pro Thr Phe Gly Gly Gly Thr Lys Val Glu Ile Lys
            100                 105                 110
```

<210> SEQ ID NO 31
<211> LENGTH: 10
<212> TYPE: PRT
<213> ORGANISM: Mus musculus

<400> SEQUENCE: 31

```
Gly Phe Ser Leu Thr Ser Tyr Gly Val His
1               5                   10
```

<210> SEQ ID NO 32
<211> LENGTH: 16
<212> TYPE: PRT
<213> ORGANISM: Artificial Sequence
<220> FEATURE:
<223> OTHER INFORMATION: 317-4B6 H-CDR2 or CDR-H2

<400> SEQUENCE: 32

```
Val Ile Tyr Ala Asp Gly Ser Thr Asn Tyr Asn Pro Ser Leu Lys Ser
1               5                   10                  15
```

```
<210> SEQ ID NO 33
<211> LENGTH: 12
<212> TYPE: PRT
<213> ORGANISM: Mus musculus

<400> SEQUENCE: 33

Ala Arg Ala Tyr Gly Asn Tyr Trp Tyr Ile Asp Val
1               5                   10

<210> SEQ ID NO 34
<211> LENGTH: 11
<212> TYPE: PRT
<213> ORGANISM: Artificial Sequence
<220> FEATURE:
<223> OTHER INFORMATION: 317-4B6 L-CDR1 or CDR-L1

<400> SEQUENCE: 34

Lys Ser Ser Glu Ser Val Ser Asn Asp Val Ala
1               5                   10

<210> SEQ ID NO 35
<211> LENGTH: 7
<212> TYPE: PRT
<213> ORGANISM: Mus musculus

<400> SEQUENCE: 35

Tyr Ala Phe His Arg Phe Thr
1               5

<210> SEQ ID NO 36
<211> LENGTH: 9
<212> TYPE: PRT
<213> ORGANISM: Mus musculus

<400> SEQUENCE: 36

His Gln Ala Tyr Ser Ser Pro Tyr Thr
1               5

<210> SEQ ID NO 37
<211> LENGTH: 10
<212> TYPE: PRT
<213> ORGANISM: Mus musculus

<400> SEQUENCE: 37

Gly Tyr Thr Phe Thr Asn Tyr Gly Met Asn
1               5                   10

<210> SEQ ID NO 38
<211> LENGTH: 17
<212> TYPE: PRT
<213> ORGANISM: Artificial Sequence
<220> FEATURE:
<223> OTHER INFORMATION: 326-4A3 H-CDR2 or CDR-H2

<400> SEQUENCE: 38

Trp Ile Asn Asn Asn Asn Ala Glu Pro Thr Tyr Ala Gln Asp Phe Arg
1               5                   10                  15
Gly

<210> SEQ ID NO 39
<211> LENGTH: 7
<212> TYPE: PRT
<213> ORGANISM: Mus musculus

<400> SEQUENCE: 39
```

Ala Arg Asp Val Met Asp Tyr
1               5

<210> SEQ ID NO 40
<211> LENGTH: 15
<212> TYPE: PRT
<213> ORGANISM: Mus musculus

<400> SEQUENCE: 40

Arg Ala Ser Glu Ser Val Asp Asn Tyr Gly Tyr Ser Phe Met His
1               5                   10                  15

<210> SEQ ID NO 41
<211> LENGTH: 7
<212> TYPE: PRT
<213> ORGANISM: Mus musculus

<400> SEQUENCE: 41

Arg Ala Ser Asn Leu Glu Ser
1               5

<210> SEQ ID NO 42
<211> LENGTH: 8
<212> TYPE: PRT
<213> ORGANISM: Mus musculus

<400> SEQUENCE: 42

Gln Gln Ser Lys Glu Tyr Pro Thr
1               5

<210> SEQ ID NO 43
<211> LENGTH: 118
<212> TYPE: PRT
<213> ORGANISM: Artificial Sequence
<220> FEATURE:
<223> OTHER INFORMATION: 317-4B2 pro-Vh

<400> SEQUENCE: 43

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Ser Tyr
                20                  25                  30

Gly Val His Trp Ile Arg Gln Pro Pro Gly Lys Gly Leu Glu Trp Ile
            35                  40                  45

Gly Val Ile Tyr Ala Gly Gly Ser Thr Asn Tyr Asn Pro Ser Leu Lys
        50                  55                  60

Ser Arg Val Thr Ile Ser Lys Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Ala Tyr Gly Asn Tyr Trp Tyr Ile Asp Val Trp Gly Gln Gly Thr
                100                 105                 110

Thr Val Thr Val Ser Ser
            115

<210> SEQ ID NO 44
<211> LENGTH: 107
<212> TYPE: PRT
<213> ORGANISM: Artificial Sequence
<220> FEATURE:
<223> OTHER INFORMATION: 317-4B2 pro-Vk

<400> SEQUENCE: 44

Asp Ile Val Met Thr Gln Ser Pro Asp Ser Leu Ala Val Ser Leu Gly
1               5                   10                  15

Glu Arg Ala Thr Ile Asn Cys Lys Ser Ser Glu Ser Val Ser Asn Asp
            20                  25                  30

Val Ala Trp Tyr Gln Gln Lys Pro Gly Gln Pro Pro Lys Leu Leu Ile
        35                  40                  45

Asn Tyr Ala Phe His Arg Phe Thr Gly Val Pro Asp Arg Phe Ser Gly
50                  55                  60

Ser Gly Tyr Gly Thr Asp Phe Thr Leu Thr Ile Ser Ser Leu Gln Ala
65                  70                  75                  80

Glu Asp Val Ala Val Tyr Tyr Cys His Gln Ala Tyr Ser Ser Pro Tyr
                85                  90                  95

Thr Phe Gly Gln Gly Thr Lys Leu Glu Ile Lys
            100                 105

<210> SEQ ID NO 45
<211> LENGTH: 118
<212> TYPE: PRT
<213> ORGANISM: Artificial Sequence
<220> FEATURE:
<223> OTHER INFORMATION: 317-4B5 pro-Vh

<400> SEQUENCE: 45

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Ser Tyr
            20                  25                  30

Gly Val His Trp Ile Arg Gln Pro Pro Gly Lys Gly Leu Glu Trp Ile
        35                  40                  45

Gly Val Ile Tyr Ala Gly Gly Ser Thr Asn Tyr Asn Pro Ser Leu Lys
50                  55                  60

Ser Arg Val Thr Ile Ser Lys Asp Thr Ser Lys Asn Gln Val Ser Leu
65                  70                  75                  80

Lys Leu Ser Ser Val Thr Ala Ala Asp Thr Ala Val Tyr Tyr Cys Ala
                85                  90                  95

Arg Ala Tyr Gly Asn Tyr Trp Tyr Ile Asp Val Trp Gly Gln Gly Thr
            100                 105                 110

Thr Val Thr Val Ser Ser
        115

<210> SEQ ID NO 46
<211> LENGTH: 107
<212> TYPE: PRT
<213> ORGANISM: Artificial Sequence
<220> FEATURE:
<223> OTHER INFORMATION: 317-4B5 pro-Vk

<400> SEQUENCE: 46

Asp Ile Val Met Thr Gln Ser Pro Asp Ser Leu Ala Val Ser Leu Gly
1               5                   10                  15

Glu Arg Ala Thr Ile Asn Cys Lys Ser Ser Glu Ser Val Ser Asn Asp
            20                  25                  30

Val Ala Trp Tyr Gln Gln Lys Pro Gly Gln Pro Pro Lys Leu Leu Ile
        35                  40                  45

Asn Tyr Ala Phe His Arg Phe Thr Gly Val Pro Asp Arg Phe Ser Gly
50                  55                  60

Ser Gly Tyr Gly Thr Asp Phe Thr Leu Thr Ile Ser Ser Leu Gln Ala
65                  70                  75                  80

Glu Asp Val Ala Val Tyr Tyr Cys His Gln Ala Tyr Ser Ser Pro Tyr
                85                  90                  95

Thr Phe Gly Gln Gly Thr Lys Leu Glu Ile Lys
            100                 105

<210> SEQ ID NO 47
<211> LENGTH: 354
<212> TYPE: DNA
<213> ORGANISM: Artificial Sequence
<220> FEATURE:
<223> OTHER INFORMATION: 317-1 cDNA-Vh

<400> SEQUENCE: 47
caggtgcagc tgcaggagtc gggaccagga ctggtgaagc cttcggagac cctgtccctc      60
acctgcactg tctctgggtt ttcattaacc agctatggtg tacactggat ccggcagccc    120
ccagggaagg gactggagtg gctgggggtc atatgggccg gtggaagcac aaattataat    180
ccctccctca agagtcgact gaccatatca aagacaact ccaagagcca ggtttccctg     240
aagatgagct ctgtgaccgc tgcggacacg gccgtgtatt actgtgcgag agcctatggt    300
aactactggt acatcgatgt ctggggccaa gggaccacgg tcaccgtctc ctca          354

<210> SEQ ID NO 48
<211> LENGTH: 118
<212> TYPE: PRT
<213> ORGANISM: Artificial Sequence
<220> FEATURE:
<223> OTHER INFORMATION: 317-1 pro-Vh

<400> SEQUENCE: 48

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Ser Tyr
            20                  25                  30

Gly Val His Trp Ile Arg Gln Pro Pro Gly Lys Gly Leu Glu Trp Leu
        35                  40                  45

Gly Val Ile Trp Ala Gly Gly Ser Thr Asn Tyr Asn Pro Ser Leu Lys
    50                  55                  60

Ser Arg Leu Thr Ile Ser Lys Asp Asn Ser Lys Ser Gln Val Ser Leu
65                  70                  75                  80

Lys Met Ser Ser Val Thr Ala Ala Asp Thr Ala Val Tyr Tyr Cys Ala
                85                  90                  95

Arg Ala Tyr Gly Asn Tyr Trp Tyr Ile Asp Val Trp Gly Gln Gly Thr
            100                 105                 110

Thr Val Thr Val Ser Ser
        115

<210> SEQ ID NO 49
<211> LENGTH: 321
<212> TYPE: DNA
<213> ORGANISM: Artificial Sequence
<220> FEATURE:
<223> OTHER INFORMATION: 317-1 cDNA-Vk

<400> SEQUENCE: 49
gacatcgtga tgacccagtc tccagactcc ctggctgtgt ctctgggcga gagggccacc      60
atcaactgca aggccagcca gagtgtgagt aatgatgtag cttggtacca gcagaaacca    120

```
ggacagcctc ctaagctgct cattaactat gcatttcatc gcttcactgg ggtccctgac    180
cgattcagtg gcagcgggta tgggacagat ttcactctca ccatcagcag cctgcaggct    240
gaagatgtgg cagtttatta ctgtcaccag gcttatagtt ctccgtacac gtttggcggg    300
gggaccaagc tggagatcaa a                                              321
```

```
<210> SEQ ID NO 50
<211> LENGTH: 107
<212> TYPE: PRT
<213> ORGANISM: Artificial Sequence
<220> FEATURE:
<223> OTHER INFORMATION: 317-1 pro-Vk

<400> SEQUENCE: 50

Asp Ile Val Met Thr Gln Ser Pro Asp Ser Leu Ala Val Ser Leu Gly
1               5                   10                  15

Glu Arg Ala Thr Ile Asn Cys Lys Ala Ser Gln Ser Val Ser Asn Asp
                20                  25                  30

Val Ala Trp Tyr Gln Gln Lys Pro Gly Gln Pro Pro Lys Leu Leu Ile
            35                  40                  45

Asn Tyr Ala Phe His Arg Phe Thr Gly Val Pro Asp Arg Phe Ser Gly
        50                  55                  60

Ser Gly Tyr Gly Thr Asp Phe Thr Leu Thr Ile Ser Ser Leu Gln Ala
65                  70                  75                  80

Glu Asp Val Ala Val Tyr Tyr Cys His Gln Ala Tyr Ser Ser Pro Tyr
                85                  90                  95

Thr Phe Gly Gly Gly Thr Lys Leu Glu Ile Lys
            100                 105

<210> SEQ ID NO 51
<211> LENGTH: 114
<212> TYPE: PRT
<213> ORGANISM: Artificial Sequence
<220> FEATURE:
<223> OTHER INFORMATION: 326-3B1 pro-Vh

<400> SEQUENCE: 51

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asn Tyr
                20                  25                  30

Gly Met Asn Trp Val Arg Gln Ala Pro Gly Gln Gly Leu Lys Trp Met
            35                  40                  45

Gly Trp Ile Asn Asn Asn Gly Glu Pro Thr Tyr Ala Gln Asp Phe
        50                  55                  60

Arg Gly Arg Phe Val Phe Ser Leu Asp Thr Ser Ala Ser Thr Ala Tyr
65                  70                  75                  80

Leu Gln Ile Ser Ser Leu Lys Thr Glu Asp Thr Ala Val Tyr Tyr Cys
                85                  90                  95

Ala Arg Asp Val Met Asp Tyr Trp Gly Gln Gly Thr Leu Val Thr Val
            100                 105                 110

Ser Ser

<210> SEQ ID NO 52
<211> LENGTH: 110
<212> TYPE: PRT
<213> ORGANISM: Artificial Sequence
<220> FEATURE:
<223> OTHER INFORMATION: 326-3B1 pro-Vk
```

<400> SEQUENCE: 52

Asp Ile Val Leu Thr Gln Ser Pro Ala Ser Leu Ala Val Ser Pro Gly
1               5                   10                  15

Gln Arg Ala Thr Ile Thr Cys Arg Ala Ser Glu Ser Val Asp Asn Tyr
            20                  25                  30

Gly Tyr Ser Phe Met His Trp Tyr Gln Gln Lys Pro Gly Gln Pro Pro
        35                  40                  45

Lys Leu Leu Ile Tyr Arg Ala Ser Asn Leu Glu Ser Gly Val Pro Ala
    50                  55                  60

Arg Phe Ser Gly Ser Gly Ser Arg Thr Asp Phe Thr Leu Thr Ile Asn
65                  70                  75                  80

Pro Val Glu Ala Asn Asp Thr Ala Asn Tyr Tyr Cys Gln Gln Ser Lys
                85                  90                  95

Glu Tyr Pro Thr Phe Gly Gly Gly Thr Lys Val Glu Ile Lys
            100                 105                 110

<210> SEQ ID NO 53
<211> LENGTH: 114
<212> TYPE: PRT
<213> ORGANISM: Artificial Sequence
<220> FEATURE:
<223> OTHER INFORMATION: 326-3G1 pro-Vh

<400> SEQUENCE: 53

Gln Val Gln Leu Val Gln Ser Gly Pro Glu Leu Lys Lys Pro Gly Ala
1               5                   10                  15

Ser Val Lys Val Ser Cys Lys Ala Ser Gly Tyr Thr Phe Thr Asn Tyr
            20                  25                  30

Gly Met Asn Trp Val Arg Gln Ala Pro Gly Gln Gly Leu Lys Trp Met
        35                  40                  45

Gly Trp Ile Asn Asn Asn Asn Gly Glu Pro Thr Tyr Ala Gln Asp Phe
    50                  55                  60

Arg Gly Arg Phe Val Phe Ser Leu Asp Thr Ser Ala Ser Thr Ala Tyr
65                  70                  75                  80

Leu Gln Ile Ser Ser Leu Lys Thr Glu Asp Thr Ala Val Tyr Tyr Cys
                85                  90                  95

Ala Arg Asp Val Met Asp Tyr Trp Gly Gln Gly Thr Leu Val Thr Val
            100                 105                 110

Ser Ser

<210> SEQ ID NO 54
<211> LENGTH: 110
<212> TYPE: PRT
<213> ORGANISM: Artificial Sequence
<220> FEATURE:
<223> OTHER INFORMATION: 326-3G1 pro-Vk

<400> SEQUENCE: 54

Asp Ile Val Leu Thr Gln Ser Pro Ala Ser Leu Ala Val Ser Pro Gly
1               5                   10                  15

Gln Arg Ala Thr Ile Thr Cys Arg Ala Ser Glu Ser Val Asp Asn Tyr
            20                  25                  30

Gly Tyr Ser Phe Met His Trp Tyr Gln Gln Lys Pro Gly Gln Pro Pro
        35                  40                  45

Lys Leu Leu Ile Tyr Arg Ala Ser Asn Leu Glu Ser Gly Val Pro Ala
    50                  55                  60

Arg Phe Ser Gly Ser Gly Ser Arg Thr Asp Phe Thr Leu Thr Ile Asn
65                  70                  75                  80

Pro Val Glu Ala Asn Asp Thr Ala Asn Tyr Tyr Cys Gln Gln Ser Lys
                85                  90                  95

Glu Tyr Pro Thr Phe Gly Gly Gly Thr Lys Val Glu Ile Lys
            100                 105                 110

<210> SEQ ID NO 55
<211> LENGTH: 342
<212> TYPE: DNA
<213> ORGANISM: Artificial Sequence
<220> FEATURE:
<223> OTHER INFORMATION: 326-1 cDNA-Vh

<400> SEQUENCE: 55
caggtgcagc tggtgcagag cggcagcgag ctgaagaagc ccggcgccag cgtgaaggtg      60
agctgcaagg ccagcggcta caccttcacc aactacggca tgaactgggt gagacaggcc     120
cccggccagg gcctggagtg gatgggctgg atcaacaaca acaacggcga gcccacctac     180
gcccagggct tcagaggcag attcgtgttc agcctggaca ccagcgccag caccgcctac     240
ctgcagatca gcagcctgaa gaccgaggac accgccgtgt acttctgcgc cagagacgtg     300
atggactact ggggccaggg caccaccgtg accgtgagca gc                        342

<210> SEQ ID NO 56
<211> LENGTH: 114
<212> TYPE: PRT
<213> ORGANISM: Artificial Sequence
<220> FEATURE:
<223> OTHER INFORMATION: 326-1 pro-Vh

<400> SEQUENCE: 56

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asn Tyr
                20                  25                  30

Gly Met Asn Trp Val Arg Gln Ala Pro Gly Gln Gly Leu Glu Trp Met
            35                  40                  45

Gly Trp Ile Asn Asn Asn Asn Gly Glu Pro Thr Tyr Ala Gln Gly Phe
        50                  55                  60

Arg Gly Arg Phe Val Phe Ser Leu Asp Thr Ser Ala Ser Thr Ala Tyr
65                  70                  75                  80

Leu Gln Ile Ser Ser Leu Lys Thr Glu Asp Thr Ala Val Tyr Phe Cys
                85                  90                  95

Ala Arg Asp Val Met Asp Tyr Trp Gly Gln Gly Thr Thr Val Thr Val
            100                 105                 110

Ser Ser

<210> SEQ ID NO 57
<211> LENGTH: 330
<212> TYPE: DNA
<213> ORGANISM: Artificial Sequence
<220> FEATURE:
<223> OTHER INFORMATION: 326-1 cDNA-Vk

<400> SEQUENCE: 57
gacattgtgc tgacccagtc tccagcctcc ttggccgtgt ctccaggaca gagggccacc      60
atcacctgca gagccagtga aagtgttgat aattatggca tagtttttat gcactggtat     120
cagcagaaac caggacaacc tcctaaactc ctgatttacc gtgcatccaa cctagaatct     180

```
ggggtcccag ccaggttcag cggcagtggg tctaggaccg atttcacccct cacaattaat    240 cctgtggaag ctaatgatac tgcaaattat tactgtcagc aaagtaaaga atatccgacg    300
ttcggcggag ggaccaaggt ggagatcaaa                                      330
```

<210> SEQ ID NO 58
<211> LENGTH: 110
<212> TYPE: PRT
<213> ORGANISM: Artificial Sequence
<220> FEATURE:
<223> OTHER INFORMATION: 326-1 pro-Vk

<400> SEQUENCE: 58

```
Asp Ile Val Leu Thr Gln Ser Pro Ala Ser Leu Ala Val Ser Pro Gly
1               5                   10                  15

Gln Arg Ala Thr Ile Thr Cys Arg Ala Ser Glu Ser Val Asp Asn Tyr
            20                  25                  30

Gly Tyr Ser Phe Met His Trp Tyr Gln Gln Lys Pro Gly Gln Pro Pro
        35                  40                  45

Lys Leu Leu Ile Tyr Arg Ala Ser Asn Leu Glu Ser Gly Val Pro Ala
    50                  55                  60

Arg Phe Ser Gly Ser Gly Ser Arg Thr Asp Phe Thr Leu Thr Ile Asn
65                  70                  75                  80

Pro Val Glu Ala Asn Asp Thr Ala Asn Tyr Tyr Cys Gln Gln Ser Lys
                85                  90                  95

Glu Tyr Pro Thr Phe Gly Gly Gly Thr Lys Val Glu Ile Lys
            100                 105                 110
```

<210> SEQ ID NO 59
<211> LENGTH: 16
<212> TYPE: PRT
<213> ORGANISM: Artificial Sequence
<220> FEATURE:
<223> OTHER INFORMATION: 317-1 H-CDR2 or CDR-H2

<400> SEQUENCE: 59

```
Val Ile Trp Ala Gly Gly Ser Thr Asn Tyr Asn Pro Ser Leu Lys Ser
1               5                   10                  15
```

<210> SEQ ID NO 60
<211> LENGTH: 16
<212> TYPE: PRT
<213> ORGANISM: Artificial Sequence
<220> FEATURE:
<223> OTHER INFORMATION: 317-4B2 H-CDR2 or CDR-H2

<400> SEQUENCE: 60

```
Val Ile Tyr Ala Gly Gly Ser Thr Asn Tyr Asn Pro Ser Leu Lys Ser
1               5                   10                  15
```

<210> SEQ ID NO 61
<211> LENGTH: 11
<212> TYPE: PRT
<213> ORGANISM: Artificial Sequence
<220> FEATURE:
<223> OTHER INFORMATION: 317-4B2 L-CDR1 or CDR-L1

<400> SEQUENCE: 61

```
Lys Ser Ser Glu Ser Val Ser Asn Asp Val Ala
1               5                   10
```

<210> SEQ ID NO 62

```
<211> LENGTH: 17
<212> TYPE: PRT
<213> ORGANISM: Artificial Sequence
<220> FEATURE:
<223> OTHER INFORMATION: 326-1 H-CDR2 or CDR-H2

<400> SEQUENCE: 62

Trp Ile Asn Asn Asn Asn Gly Glu Pro Thr Tyr Ala Gln Gly Phe Arg
1               5                   10                  15

Gly

<210> SEQ ID NO 63
<211> LENGTH: 17
<212> TYPE: PRT
<213> ORGANISM: Artificial Sequence
<220> FEATURE:
<223> OTHER INFORMATION: 326-3G1 H-CDR2 or CDR-H2

<400> SEQUENCE: 63

Trp Ile Asn Asn Asn Asn Gly Glu Pro Thr Tyr Ala Gln Asp Phe Arg
1               5                   10                  15

Gly

<210> SEQ ID NO 64
<211> LENGTH: 118
<212> TYPE: PRT
<213> ORGANISM: Artificial Sequence
<220> FEATURE:
<223> OTHER INFORMATION: 317-3A1 pro-Vh

<400> SEQUENCE: 64

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Ser Tyr
            20                  25                  30

Gly Val His Trp Ile Arg Gln Pro Pro Gly Lys Gly Leu Glu Trp Ile
        35                  40                  45

Gly Val Ile Trp Ala Gly Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Ala Tyr Gly Asn Tyr Trp Tyr Ile Asp Val Trp Gly Gln Gly Thr
            100                 105                 110

Thr Val Thr Val Ser Ser
        115

<210> SEQ ID NO 65
<211> LENGTH: 118
<212> TYPE: PRT
<213> ORGANISM: Artificial Sequence
<220> FEATURE:
<223> OTHER INFORMATION: 317-3C1 pro-Vh

<400> SEQUENCE: 65

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Ser Tyr
            20                  25                  30

Gly Val His Trp Ile Arg Gln Pro Pro Gly Lys Gly Leu Glu Trp Leu
```

```
                35                  40                  45

Gly Val Ile Trp Ala Gly Gly Ser Thr Asn Tyr Asn Pro Ser Leu Lys
            50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Ala Tyr Gly Asn Tyr Trp Tyr Ile Asp Val Trp Gly Gln Gly Thr
            100                 105                 110

Thr Val Thr Val Ser Ser
        115

<210> SEQ ID NO 66
<211> LENGTH: 118
<212> TYPE: PRT
<213> ORGANISM: Artificial Sequence
<220> FEATURE:
<223> OTHER INFORMATION: 317-3E1 pro-Vh

<400> SEQUENCE: 66

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Ser Tyr
            20                  25                  30

Gly Val His Trp Ile Arg Gln Pro Pro Gly Lys Gly Leu Glu Trp Ile
        35                  40                  45

Gly Val Ile Trp Ala Gly Gly Ser Thr Asn Tyr Asn Pro Ser Leu Lys
    50                  55                  60

Ser Arg Val Thr Ile Ser Val Asp Thr Ser Lys Ser Gln Phe Ser Leu
65                  70                  75                  80

Lys Leu Ser Ser Val Thr Ala Ala Asp Thr Ala Val Tyr Tyr Cys Ala
                85                  90                  95

Arg Ala Tyr Gly Asn Tyr Trp Tyr Ile Asp Val Trp Gly Gln Gly Thr
            100                 105                 110

Thr Val Thr Val Ser Ser
        115

<210> SEQ ID NO 67
<211> LENGTH: 118
<212> TYPE: PRT
<213> ORGANISM: Artificial Sequence
<220> FEATURE:
<223> OTHER INFORMATION: 317-3F1 pro-Vh

<400> SEQUENCE: 67

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Ser Tyr
            20                  25                  30

Gly Val His Trp Ile Arg Gln Pro Pro Gly Lys Gly Leu Glu Trp Ile
        35                  40                  45

Gly Val Ile Trp Ala Gly Gly Ser Thr Asn Tyr Asn Pro Ser Leu Lys
    50                  55                  60

Ser Arg Val Thr Ile Ser Val Asp Thr Ser Lys Asn Gln Val Ser Leu
65                  70                  75                  80

Lys Leu Ser Ser Val Thr Ala Ala Asp Thr Ala Val Tyr Tyr Cys Ala
                85                  90                  95
```

Arg Ala Tyr Gly Asn Tyr Trp Tyr Ile Asp Val Trp Gly Gln Gly Thr
            100                 105                 110

Thr Val Thr Val Ser Ser
        115

<210> SEQ ID NO 68
<211> LENGTH: 118
<212> TYPE: PRT
<213> ORGANISM: Artificial Sequence
<220> FEATURE:
<223> OTHER INFORMATION: 317-3G1 pro-Vh

<400> SEQUENCE: 68

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Ser Tyr
            20                  25                  30

Gly Val His Trp Ile Arg Gln Pro Pro Gly Lys Gly Leu Glu Trp Ile
        35                  40                  45

Gly Val Ile Trp Ala Gly Gly Ser Thr Asn Tyr Asn Pro Ser Leu Lys
    50                  55                  60

Ser Arg Val Thr Ile Ser Val Asp Thr Ser Lys Ser Gln Val Ser Leu
65                  70                  75                  80

Lys Leu Ser Ser Val Thr Ala Ala Asp Thr Ala Val Tyr Tyr Cys Ala
                85                  90                  95

Arg Ala Tyr Gly Asn Tyr Trp Tyr Ile Asp Val Trp Gly Gln Gly Thr
            100                 105                 110

Thr Val Thr Val Ser Ser
        115

<210> SEQ ID NO 69
<211> LENGTH: 118
<212> TYPE: PRT
<213> ORGANISM: Artificial Sequence
<220> FEATURE:
<223> OTHER INFORMATION: 317-3H1 pro-Vh

<400> SEQUENCE: 69

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Ser Tyr
            20                  25                  30

Gly Val His Trp Ile Arg Gln Pro Pro Gly Lys Gly Leu Glu Trp Ile
        35                  40                  45

Gly Val Ile Trp Ala Gly Gly Ser Thr Asn Tyr Asn Pro Ser Leu Lys
    50                  55                  60

Ser Arg Val Thr Ile Ser Lys Asp Thr Ser Lys Ser Gln Val Ser Leu
65                  70                  75                  80

Lys Leu Ser Ser Val Thr Ala Ala Asp Thr Ala Val Tyr Tyr Cys Ala
                85                  90                  95

Arg Ala Tyr Gly Asn Tyr Trp Tyr Ile Asp Val Trp Gly Gln Gly Thr
            100                 105                 110

Thr Val Thr Val Ser Ser
        115

<210> SEQ ID NO 70
<211> LENGTH: 118
<212> TYPE: PRT
<213> ORGANISM: Artificial Sequence

```
<220> FEATURE:
<223> OTHER INFORMATION: 317-3I1 pro-Vh

<400> SEQUENCE: 70

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Ser Tyr
            20                  25                  30

Gly Val His Trp Ile Arg Gln Pro Pro Gly Lys Gly Leu Glu Trp Ile
        35                  40                  45

Gly Val Ile Trp Ala Gly Gly Ser Thr Asn Tyr Asn Pro Ser Leu Lys
    50                  55                  60

Ser Arg Val Thr Ile Ser Lys Asp Thr Ser Lys Asn Gln Val Ser Leu
65                  70                  75                  80

Lys Leu Ser Ser Val Thr Ala Ala Asp Thr Ala Val Tyr Tyr Cys Ala
                85                  90                  95

Arg Ala Tyr Gly Asn Tyr Trp Tyr Ile Asp Val Trp Gly Gln Gly Thr
            100                 105                 110

Thr Val Thr Val Ser Ser
        115

<210> SEQ ID NO 71
<211> LENGTH: 118
<212> TYPE: PRT
<213> ORGANISM: Artificial Sequence
<220> FEATURE:
<223> OTHER INFORMATION: 317-4B1 pro-Vh

<400> SEQUENCE: 71

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Ser Tyr
            20                  25                  30

Gly Val His Trp Ile Arg Gln Pro Pro Gly Lys Gly Leu Glu Trp Ile
        35                  40                  45

Gly Val Ile Trp Ala Gly Gly Ser Thr Asn Tyr Asn Pro Ser Leu Lys
    50                  55                  60

Ser Arg Val Thr Ile Ser Lys Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Ala Tyr Gly Asn Tyr Trp Tyr Ile Asp Val Trp Gly Gln Gly Thr
            100                 105                 110

Thr Val Thr Val Ser Ser
        115

<210> SEQ ID NO 72
<211> LENGTH: 118
<212> TYPE: PRT
<213> ORGANISM: Artificial Sequence
<220> FEATURE:
<223> OTHER INFORMATION: 317-4B3 pro-Vh

<400> SEQUENCE: 72

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Ser Tyr
            20                  25                  30
```

Gly Val His Trp Ile Arg Gln Pro Gly Lys Gly Leu Glu Trp Ile
         35                  40                  45

Gly Val Ile Asn Ala Gly Gly Ser Thr Asn Tyr Asn Pro Ser Leu Lys
 50                      55                  60

Ser Arg Val Thr Ile Ser Lys Asp Thr Ser Lys Asn Gln Phe Ser Leu
 65                  70                  75                  80

Lys Leu Ser Ser Val Thr Ala Ala Asp Thr Ala Val Tyr Tyr Cys Ala
                 85                  90                  95

Arg Ala Tyr Gly Asn Tyr Trp Tyr Ile Asp Val Trp Gly Gln Gly Thr
             100                 105                 110

Thr Val Thr Val Ser Ser
             115

<210> SEQ ID NO 73
<211> LENGTH: 118
<212> TYPE: PRT
<213> ORGANISM: Artificial Sequence
<220> FEATURE:
<223> OTHER INFORMATION: 317-4B4 pro-Vh

<400> SEQUENCE: 73

Gln Val Gln Leu Gln Glu Ser Gly Pro Gly Leu Val Lys Pro Ser Glu
 1               5                  10                  15

Thr Leu Ser Leu Thr Cys Thr Val Ser Gly Phe Ser Leu Thr Ser Tyr
             20                  25                  30

Gly Val His Trp Ile Arg Gln Pro Gly Lys Gly Leu Glu Trp Ile
         35                  40                  45

Gly Val Ile Trp Ala Gly Gly Ser Thr Asn Tyr Asn Pro Ser Leu Lys
 50                      55                  60

Ser Arg Val Thr Ile Ser Lys Asp Thr Ser Lys Asn Gln Phe Ser Leu
 65                  70                  75                  80

Lys Leu Ser Ser Val Thr Ala Ala Asp Thr Ala Val Tyr Tyr Cys Ala
                 85                  90                  95

Arg Ala Tyr Gly Asn Tyr Pro Tyr Ile Asp Val Trp Gly Gln Gly Thr
             100                 105                 110

Thr Val Thr Val Ser Ser
             115

<210> SEQ ID NO 74
<211> LENGTH: 107
<212> TYPE: PRT
<213> ORGANISM: Artificial Sequence
<220> FEATURE:
<223> OTHER INFORMATION: 317-4A2 pro-Vk

<400> SEQUENCE: 74

Asp Ile Val Met Thr Gln Ser Pro Asp Ser Leu Ala Val Ser Leu Gly
 1               5                  10                  15

Glu Arg Ala Thr Ile Asn Cys Lys Ser Ser Gln Ser Val Ser Asn Asp
             20                  25                  30

Val Ala Trp Tyr Gln Gln Lys Pro Gly Gln Pro Pro Lys Leu Leu Ile
             35                  40                  45

Asn Tyr Ala Phe His Arg Phe Thr Gly Val Pro Asp Arg Phe Ser Gly
             50                  55                  60

Ser Gly Tyr Gly Thr Asp Phe Thr Leu Thr Ile Ser Ser Leu Gln Ala
 65                  70                  75                  80

Glu Asp Val Ala Val Tyr Tyr Cys His Gln Ala Tyr Ser Ser Pro Tyr
                 85                  90                  95

Thr Phe Gly Gln Gly Thr Lys Leu Glu Ile Lys
            100                 105

<210> SEQ ID NO 75
<211> LENGTH: 114
<212> TYPE: PRT
<213> ORGANISM: Artificial Sequence
<220> FEATURE:
<223> OTHER INFORMATION: 326-3A1 pro-Vh

<400> SEQUENCE: 75

Gln Val Gln Leu Val Gln Ser Gly Pro Glu Leu Lys Lys Pro Gly Ala
1               5                   10                  15

Ser Val Lys Val Ser Cys Lys Ala Ser Gly Tyr Thr Phe Thr Asn Tyr
            20                  25                  30

Gly Met Asn Trp Val Arg Gln Ala Pro Gly Gln Gly Leu Glu Trp Met
        35                  40                  45

Gly Trp Ile Asn Asn Asn Gly Glu Pro Thr Tyr Ala Gln Gly Phe
    50                  55                  60

Arg Gly Arg Phe Val Phe Ser Leu Asp Thr Ser Ala Ser Thr Ala Tyr
65                  70                  75                  80

Leu Gln Ile Ser Ser Leu Lys Thr Glu Asp Thr Ala Val Tyr Tyr Cys
                85                  90                  95

Ala Arg Asp Val Met Asp Tyr Trp Gly Gln Gly Thr Leu Val Thr Val
            100                 105                 110

Ser Ser

<210> SEQ ID NO 76
<211> LENGTH: 114
<212> TYPE: PRT
<213> ORGANISM: Artificial Sequence
<220> FEATURE:
<223> OTHER INFORMATION: 326-3C1 pro-Vh

<400> SEQUENCE: 76

Gln Val Gln Leu Val Gln Ser Gly Pro Glu Leu Lys Lys Pro Gly Ala
1               5                   10                  15

Ser Val Lys Val Ser Cys Lys Ala Ser Gly Tyr Thr Phe Thr Asn Tyr
            20                  25                  30

Gly Met Asn Trp Val Arg Gln Ala Pro Gly Gln Gly Leu Lys Trp Met
        35                  40                  45

Gly Trp Ile Asn Asn Asn Gly Glu Pro Thr Tyr Ala Gln Asp Phe
    50                  55                  60

Arg Gly Arg Phe Val Phe Ser Leu Asp Thr Ser Ala Ser Thr Ala Tyr
65                  70                  75                  80

Leu Gln Ile Ser Ser Leu Lys Thr Glu Asp Thr Ala Val Tyr Tyr Cys
                85                  90                  95

Ala Arg Asp Val Met Asp Tyr Trp Gly Gln Gly Thr Thr Val Thr Val
            100                 105                 110

Ser Ser

<210> SEQ ID NO 77
<211> LENGTH: 114
<212> TYPE: PRT
<213> ORGANISM: Artificial Sequence
<220> FEATURE:
<223> OTHER INFORMATION: 326-3D1 pro-Vh

<400> SEQUENCE: 77

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asn Tyr
            20                  25                  30

Gly Met Asn Trp Val Arg Gln Ala Pro Gly Gln Gly Leu Glu Trp Met
        35                  40                  45

Gly Trp Ile Asn Asn Asn Gly Glu Pro Thr Tyr Ala Gln Gly Phe
50                  55                  60

Arg Gly Arg Phe Val Phe Ser Leu Asp Thr Ser Ala Ser Thr Ala Tyr
65                  70                  75                  80

Leu Gln Ile Ser Ser Leu Lys Thr Glu Asp Thr Ala Val Tyr Tyr Cys
                85                  90                  95

Ala Arg Asp Val Met Asp Tyr Trp Gly Gln Gly Thr Leu Val Thr Val
            100                 105                 110

Ser Ser

<210> SEQ ID NO 78
<211> LENGTH: 114
<212> TYPE: PRT
<213> ORGANISM: Artificial Sequence
<220> FEATURE:
<223> OTHER INFORMATION: 326-3E1 pro-Vh

<400> SEQUENCE: 78

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asn Tyr
            20                  25                  30

Gly Met Asn Trp Val Arg Gln Ala Pro Gly Gln Gly Leu Lys Trp Met
        35                  40                  45

Gly Trp Ile Asn Asn Asn Gly Glu Pro Thr Tyr Ala Gln Asp Phe
50                  55                  60

Arg Gly Arg Phe Val Phe Ser Leu Asp Thr Ser Ala Ser Thr Ala Tyr
65                  70                  75                  80

Leu Gln Ile Ser Ser Leu Lys Thr Glu Asp Thr Ala Val Tyr Tyr Cys
                85                  90                  95

Ala Arg Asp Val Met Asp Tyr Trp Gly Gln Gly Thr Thr Val Thr Val
            100                 105                 110

Ser Ser

<210> SEQ ID NO 79
<211> LENGTH: 114
<212> TYPE: PRT
<213> ORGANISM: Artificial Sequence
<220> FEATURE:
<223> OTHER INFORMATION: 326-3F1 pro-Vh

<400> SEQUENCE: 79

Gln Val Gln Leu Val Gln Ser Gly Pro Glu Leu Lys Lys Pro Gly Ala
1               5                   10                  15

Ser Val Lys Val Ser Cys Lys Ala Ser Gly Tyr Thr Phe Thr Asn Tyr
            20                  25                  30

Gly Met Asn Trp Val Arg Gln Ala Pro Gly Gln Gly Leu Glu Trp Met
        35                  40                  45

Gly Trp Ile Asn Asn Asn Gly Glu Pro Thr Tyr Ala Gln Gly Phe
50                  55                  60

```
Arg Gly Arg Phe Val Phe Ser Leu Asp Thr Ser Ala Ser Thr Ala Tyr
 65                  70                  75                  80

Leu Gln Ile Ser Ser Leu Lys Thr Glu Asp Thr Ala Val Tyr Tyr Cys
                 85                  90                  95

Ala Arg Asp Val Met Asp Tyr Trp Gly Gln Gly Thr Thr Val Thr Val
            100                 105                 110

Ser Ser

<210> SEQ ID NO 80
<211> LENGTH: 114
<212> TYPE: PRT
<213> ORGANISM: Artificial Sequence
<220> FEATURE:
<223> OTHER INFORMATION: 326-3B N55D pro-Vh

<400> SEQUENCE: 80

Gln Val Gln Leu Val Gln Ser Gly Ser Glu Leu Lys Lys Pro Gly Ala
 1               5                  10                  15

Ser Val Lys Val Ser Cys Lys Ala Ser Gly Tyr Thr Phe Thr Asn Tyr
            20                  25                  30

Gly Met Asn Trp Val Arg Gln Ala Pro Gly Gln Gly Leu Lys Trp Met
        35                  40                  45

Gly Trp Ile Asn Asn Asn Asp Gly Glu Pro Thr Tyr Ala Gln Asp Phe
 50                  55                  60

Arg Gly Arg Phe Val Phe Ser Leu Asp Thr Ser Ala Ser Thr Ala Tyr
 65                  70                  75                  80

Leu Gln Ile Ser Ser Leu Lys Thr Glu Asp Thr Ala Val Tyr Tyr Cys
                 85                  90                  95

Ala Arg Asp Val Met Asp Tyr Trp Gly Gln Gly Thr Leu Val Thr Val
            100                 105                 110

Ser Ser

<210> SEQ ID NO 81
<211> LENGTH: 110
<212> TYPE: PRT
<213> ORGANISM: Artificial Sequence
<220> FEATURE:
<223> OTHER INFORMATION: 326-4A1 pro-Vk

<400> SEQUENCE: 81

Asp Ile Val Leu Thr Gln Ser Pro Ala Ser Leu Ala Val Ser Pro Gly
 1               5                  10                  15

Gln Arg Ala Thr Ile Thr Cys Arg Ala Ser Glu Ser Val Asp Asn Tyr
            20                  25                  30

Gly Tyr Ser Phe Met His Trp Tyr Gln Gln Lys Pro Gly Gln Pro Pro
        35                  40                  45

Lys Leu Leu Ile Tyr Arg Ala Ser Asn Leu Glu Ser Gly Val Pro Ala
 50                  55                  60

Arg Phe Ser Gly Ser Gly Ser Arg Thr Asp Phe Thr Leu Thr Ile Asn
 65                  70                  75                  80

Pro Val Glu Ala Glu Asp Thr Ala Asn Tyr Tyr Cys Gln Gln Ser Lys
                 85                  90                  95

Glu Tyr Pro Thr Phe Gly Gly Thr Lys Val Glu Ile Lys
            100                 105                 110

<210> SEQ ID NO 82
<211> LENGTH: 110
<212> TYPE: PRT
```

<213> ORGANISM: Artificial Sequence
<220> FEATURE:
<223> OTHER INFORMATION: 326-4A2 pro-Vk

<400> SEQUENCE: 82

```
Asp Ile Val Leu Thr Gln Ser Pro Ala Ser Leu Ala Val Ser Pro Gly
1               5                   10                  15

Gln Arg Ala Thr Ile Thr Cys Arg Ala Ser Glu Ser Val Asp Asn Tyr
            20                  25                  30

Gly Tyr Ser Phe Met His Trp Tyr Gln Gln Lys Pro Gly Gln Pro Pro
        35                  40                  45

Lys Leu Leu Ile Tyr Arg Ala Ser Asn Leu Glu Ser Gly Val Pro Ala
    50                  55                  60

Arg Phe Ser Gly Ser Gly Ser Gly Thr Asp Phe Thr Leu Thr Ile Asn
65                  70                  75                  80

Pro Val Glu Ala Asn Asp Thr Ala Asn Tyr Tyr Cys Gln Gln Ser Lys
                85                  90                  95

Glu Tyr Pro Thr Phe Gly Gly Gly Thr Lys Val Glu Ile Lys
            100                 105                 110
```

<210> SEQ ID NO 83
<211> LENGTH: 327
<212> TYPE: PRT
<213> ORGANISM: Artificial Sequence
<220> FEATURE:
<223> OTHER INFORMATION: huIgG4mt1 pro

<400> SEQUENCE: 83

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Glu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220
```

```
Glu Pro Gln Val Tyr Thr Leu Pro Pro Ser Gln Glu Met Thr Lys
225                 230                 235                 240

Asn Gln Val Ser Leu Thr Cys Leu Val Lys Gly Phe Tyr Pro Ser Asp
            245                 250                 255

Ile Ala Val Glu Trp Glu Ser Asn Gly Gln Pro Glu Asn Asn Tyr Lys
        260                 265                 270

Thr Thr Pro Pro Val Leu Asp Ser Asp Gly Ser Phe Phe Leu Tyr Ser
    275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 84
<211> LENGTH: 327
<212> TYPE: PRT
<213> ORGANISM: Artificial Sequence
<220> FEATURE:
<223> OTHER INFORMATION: huIgG4mt2 pro

<400> SEQUENCE: 84

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Pro Val Ala Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Met Thr Lys
225                 230                 235                 240

Asn Gln Val Ser Leu Thr Cys Leu Val Lys Gly Phe Tyr Pro Ser Asp
            245                 250                 255
```

```
Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
            275                 280                 285

Arg Leu Thr Val Asp Lys Ser Arg Trp Gln Glu Gly Asn Val Phe Ser
        290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 85
<211> LENGTH: 327
<212> TYPE: PRT
<213> ORGANISM: Artificial Sequence
<220> FEATURE:
<223> OTHER INFORMATION: huIgG4mt6 pro

<400> SEQUENCE: 85

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Pro Val Ala Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Ala Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285
```

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
            325

<210> SEQ ID NO 86
<211> LENGTH: 327
<212> TYPE: PRT
<213> ORGANISM: Artificial Sequence
<220> FEATURE:
<223> OTHER INFORMATION: huIgG4mt8 pro

<400> SEQUENCE: 86

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Pro Val Ala Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
130                 135                 140

Thr Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
            325

<210> SEQ ID NO 87
<211> LENGTH: 327
<212> TYPE: PRT
<213> ORGANISM: Artificial Sequence
<220> FEATURE:
<223> OTHER INFORMATION: huIgG4mt9 pro

<400> SEQUENCE: 87

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Pro Val Ala Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Ala Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Lys Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
            325

<210> SEQ ID NO 88
<211> LENGTH: 327

```
<212> TYPE: PRT
<213> ORGANISM: Artificial Sequence
<220> FEATURE:
<223> OTHER INFORMATION: huIgG4mt10 pro

<400> SEQUENCE: 88

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
                100                 105                 110

Pro Val Ala Gly Gly Pro Ser Val Phe Leu Phe Pro Pro Lys Pro Lys
            115                 120                 125

Asp Thr Leu Met Ile Ser Arg Thr Pro Glu Val Thr Cys Val Val Val
        130                 135                 140

Ala Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Val His Gln Asp
                180                 185                 190

Trp Leu Asn Gly Lys Glu Tyr Lys Cys Lys Val Ser Asn Lys Gly Leu
            195                 200                 205

Pro Ser Ser Ile Glu Lys Thr Ile Ser Lys Ala Lys Gly Gln Pro Arg
210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
            275                 280                 285

Lys Leu Thr Val Asp Lys Ser Arg Trp Gln Glu Gly Asn Val Phe Ser
        290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 89
<211> LENGTH: 367
<212> TYPE: PRT
<213> ORGANISM: Artificial Sequence
<220> FEATURE:
<223> OTHER INFORMATION: OS8 pro

<400> SEQUENCE: 89
```

Met Glu Arg His Trp Ile Phe Leu Leu Leu Leu Ser Val Thr Ala Gly
1               5                   10                  15

Val His Ser Gln Val Gln Leu Gln Gln Ser Gly Ala Glu Leu Ala Arg
            20                  25                  30

Pro Gly Ala Ser Val Lys Met Ser Cys Lys Ala Ser Gly Tyr Thr Phe
        35                  40                  45

Thr Arg Tyr Thr Met His Trp Val Lys Gln Arg Pro Gly Gln Gly Leu
    50                  55                  60

Glu Trp Ile Gly Tyr Ile Asn Pro Ser Arg Gly Tyr Thr Asn Tyr Asn
65                  70                  75                  80

Gln Lys Phe Lys Asp Lys Ala Thr Leu Thr Thr Asp Lys Ser Ser Ser
                85                  90                  95

Thr Ala Tyr Met Gln Leu Ser Ser Leu Thr Ser Glu Asp Ser Ala Val
            100                 105                 110

Tyr Tyr Cys Ala Arg Tyr Tyr Asp Asp His Tyr Cys Leu Asp Tyr Trp
        115                 120                 125

Gly Gln Gly Thr Thr Leu Thr Val Ser Ser Gly Gly Gly Gly Ser Gly
    130                 135                 140

Gly Gly Gly Ser Gly Gly Gly Gly Ser Gln Ile Val Leu Thr Gln Ser
145                 150                 155                 160

Pro Ala Ile Met Ser Ala Ser Pro Gly Glu Lys Val Thr Met Thr Cys
                165                 170                 175

Ser Ala Ser Ser Ser Val Ser Tyr Met Asn Trp Tyr Gln Gln Lys Ser
            180                 185                 190

Gly Thr Ser Pro Lys Arg Trp Ile Tyr Asp Thr Ser Lys Leu Ala Ser
        195                 200                 205

Gly Val Pro Ala His Phe Arg Gly Ser Gly Ser Gly Thr Ser Tyr Ser
    210                 215                 220

Leu Thr Ile Ser Gly Met Glu Ala Glu Asp Ala Ala Thr Tyr Tyr Cys
225                 230                 235                 240

Gln Gln Trp Ser Ser Asn Pro Phe Thr Phe Gly Ser Gly Thr Lys Leu
                245                 250                 255

Glu Ile Asn Ser Ser Val Val Pro Val Leu Gln Lys Val Asn Ser Thr
            260                 265                 270

Thr Thr Lys Pro Val Leu Arg Thr Pro Ser Pro Val His Pro Thr Gly
        275                 280                 285

Thr Ser Gln Pro Gln Arg Pro Glu Asp Cys Arg Pro Arg Gly Ser Val
    290                 295                 300

Lys Gly Thr Gly Leu Asp Phe Ala Cys Asp Ile Tyr Ile Trp Ala Pro
305                 310                 315                 320

Leu Ala Gly Ile Cys Val Ala Leu Leu Leu Ser Leu Ile Ile Thr Leu
                325                 330                 335

Ile Cys Tyr His Arg Ser Arg Lys Arg Val Cys Lys Cys Pro Arg Pro
            340                 345                 350

Leu Val Arg Gln Glu Gly Lys Pro Arg Pro Ser Glu Lys Ile Val
        355                 360                 365

<210> SEQ ID NO 90
<211> LENGTH: 304
<212> TYPE: PRT
<213> ORGANISM: Artificial Sequence
<220> FEATURE:
<223> OTHER INFORMATION: P3Z pro

<400> SEQUENCE: 90

```
Met Gln Ile Pro Gln Ala Pro Trp Pro Val Val Trp Ala Val Leu Gln
1               5                   10                  15

Leu Gly Trp Arg Pro Gly Trp Phe Leu Asp Ser Pro Asp Arg Pro Trp
                20              25                  30

Asn Pro Pro Thr Phe Ser Pro Ala Leu Leu Val Val Thr Glu Gly Asp
            35              40                  45

Asn Ala Thr Phe Thr Cys Ser Phe Ser Asn Thr Ser Glu Ser Phe Val
50                      55                  60

Leu Asn Trp Tyr Arg Met Ser Pro Ser Asn Gln Thr Asp Lys Leu Ala
65                  70              75                      80

Ala Phe Pro Glu Asp Arg Ser Gln Pro Gly Gln Asp Cys Arg Phe Arg
                85                  90                  95

Val Thr Gln Leu Pro Asn Gly Arg Asp Phe His Met Ser Val Val Arg
                100             105                 110

Ala Arg Arg Asn Asp Ser Gly Thr Tyr Leu Cys Gly Ala Ile Ser Leu
            115             120             125

Ala Pro Lys Ala Gln Ile Lys Glu Ser Leu Arg Ala Glu Leu Arg Val
        130             135             140

Thr Glu Arg Arg Ala Glu Val Pro Thr Ala His Pro Ser Pro Ser Pro
145                 150             155                 160

Arg Pro Ala Gly Gln Phe Gln Thr Leu Val Val Gly Val Val Gly Gly
                165             170             175

Leu Leu Gly Ser Leu Val Leu Leu Val Trp Val Leu Ala Val Ile Arg
            180             185             190

Val Lys Phe Ser Arg Ser Ala Asp Ala Pro Ala Tyr Gln Gln Gly Gln
        195             200             205

Asn Gln Leu Tyr Asn Glu Leu Asn Leu Gly Arg Arg Glu Glu Tyr Asp
    210             215             220

Val Leu Asp Lys Arg Arg Gly Arg Asp Pro Glu Met Gly Gly Lys Pro
225             230             235             240

Gln Arg Arg Lys Asn Pro Gln Glu Gly Leu Tyr Asn Glu Leu Gln Lys
            245             250             255

Asp Lys Met Ala Glu Ala Tyr Ser Glu Ile Gly Met Lys Gly Glu Arg
            260             265             270

Arg Arg Gly Lys Gly His Asp Gly Leu Tyr Gln Gly Leu Ser Thr Ala
            275             280             285

Thr Lys Asp Thr Tyr Asp Ala Leu His Met Gln Ala Leu Pro Pro Arg
    290             295             300
```